United States Patent
Kim et al.

(10) Patent No.: US 8,874,216 B2
(45) Date of Patent: Oct. 28, 2014

(54) APPARATUS AND METHODS FOR MINIMALLY INVASIVE OBESITY TREATMENT

(75) Inventors: Daniel H. Kim, Houston, TX (US); David J. Robeson, Dublin, CA (US)

(73) Assignee: GEP Technology, Inc., Pleasanton, CA (US)

( * ) Notice: Subject to any disclaimer, the term of this patent is extended or adjusted under 35 U.S.C. 154(b) by 1293 days.

(21) Appl. No.: 11/934,584

(22) Filed: Nov. 2, 2007

(65) Prior Publication Data

US 2008/0195092 A1    Aug. 14, 2008

Related U.S. Application Data

(60) Provisional application No. 60/864,345, filed on Nov. 3, 2006.

(51) Int. Cl.
*A61N 1/00* (2006.01)
*A61F 5/00* (2006.01)
*A61N 1/36* (2006.01)
*A61N 1/05* (2006.01)

(52) U.S. Cl.
CPC . *A61F 5/003* (2013.01); *A61N 1/00* (2013.01); *A61F 5/0056* (2013.01); *A61N 1/0517* (2013.01); *A61N 1/36007* (2013.01)
USPC .......................................................... 607/40

(58) Field of Classification Search
CPC ............. A61N 1/00; A61N 1/02; A61N 1/04; A61N 1/05; A61N 1/372; A61N 1/375
See application file for complete search history.

(56) References Cited

U.S. PATENT DOCUMENTS

| | | | |
|---|---|---|---|
| 4,052,978 | A | 10/1977 | Eugenio |
| 4,917,092 | A | 4/1990 | Todd et al. |
| 5,147,294 | A | 9/1992 | Smith et al. |
| 5,263,480 | A | 11/1993 | Wernicke et al. |
| RE34,502 | E | 1/1994 | Webster, Jr. |
| 5,454,840 | A | 10/1995 | Krakovsky et al. |
| 5,522,854 | A | 6/1996 | Ideker et al. |
| 5,725,471 | A | 3/1998 | Davey et al. |
| 5,753,651 | A | 5/1998 | dePadova |
| 5,897,505 | A | 4/1999 | Feinberg et al. |
| 6,086,525 | A | 7/2000 | Davey et al. |
| 6,301,492 | B1 | 10/2001 | Zonenshayn |
| 6,334,442 | B1 | 1/2002 | Altamura |
| 6,348,423 | B1 | 2/2002 | Griffiths et al. |
| 6,356,787 | B1 | 3/2002 | Rezai et al. |

(Continued)

OTHER PUBLICATIONS

Al-Motabagani, M.A.H.—"An Anatomical Study of the Phrenoesophageal Ligament," IndMedica—Journal of the Anatomical Society of India, vol. 51, No. 1 (Jan. 2002-Jun. 2002), 7 pages.

(Continued)

*Primary Examiner* — Eric D. Bertram
*Assistant Examiner* — Elizabeth K So
(74) *Attorney, Agent, or Firm* — Patterson & Sheridan, L.L.P.

(57) ABSTRACT

Systems, apparatus, and methods for the treatment of obesity and/or gastro-esophageal reflux disease (GERD). An embodiment includes an implantable device having an adjustable curved portion configured for exerting a suitable mechanical force on one or more tissues or organs targeted for treatment. Embodiments of the device neuromodulate nerve tissue to effect treatment of obesity and/or GERD. Another embodiment includes an intraluminal guide for guiding placement of the implantable device in the patient.

13 Claims, 39 Drawing Sheets

(56) References Cited

U.S. PATENT DOCUMENTS

| | | | |
|---|---|---|---|
| 6,432,040 B1 * | 8/2002 | Meah | 600/37 |
| 6,438,423 B1 | 8/2002 | Rezai et al. | |
| 6,470,892 B1 | 10/2002 | Forsell | |
| 6,500,110 B1 | 12/2002 | Davey et al. | |
| 6,587,719 B1 | 7/2003 | Barrett et al. | |
| 6,609,025 B2 | 8/2003 | Barrett et al. | |
| 6,611,715 B1 | 8/2003 | Boveja | |
| 6,701,185 B2 | 3/2004 | Burnett et al. | |
| 6,721,603 B2 | 4/2004 | Zabara et al. | |
| 6,758,219 B2 | 7/2004 | Sapala et al. | |
| 6,759,063 B2 | 7/2004 | Almada | |
| 6,879,859 B1 | 4/2005 | Boveja | |
| 6,885,888 B2 | 4/2005 | Rezai | |
| 6,928,320 B2 | 8/2005 | King | |
| 6,937,896 B1 | 8/2005 | Kroll | |
| 6,950,707 B2 | 9/2005 | Whitehurst | |
| 7,077,821 B2 | 7/2006 | Durgin | |
| 7,167,750 B2 | 1/2007 | Knudson et al. | |
| 7,184,828 B2 | 2/2007 | Hill et al. | |
| 7,200,443 B2 | 4/2007 | Faul | |
| 7,236,822 B2 | 6/2007 | Dobak, III | |
| 7,239,912 B2 | 7/2007 | Dobak, III | |
| 7,263,405 B2 | 8/2007 | Boveja et al. | |
| 7,266,410 B2 | 9/2007 | Chen | |
| 7,299,091 B2 | 11/2007 | Barrett et al. | |
| 7,310,557 B2 | 12/2007 | Maschino et al. | |
| 7,337,005 B2 | 2/2008 | Kim et al. | |
| 7,340,306 B2 | 3/2008 | Barrett et al. | |
| 7,477,945 B2 | 1/2009 | Rezai et al. | |
| 7,483,746 B2 | 1/2009 | Lee et al. | |
| 7,489,969 B2 | 2/2009 | Knudson et al. | |
| 7,494,661 B2 | 2/2009 | Sanders | |
| 7,499,752 B2 | 3/2009 | Maschino et al. | |
| 7,529,582 B1 | 5/2009 | DiLorenzo | |
| 7,699,770 B2 * | 4/2010 | Hassler et al. | 600/37 |
| 2003/0018367 A1 | 1/2003 | DiLorenzo | |
| 2003/0054015 A1 | 3/2003 | Haze et al. | |
| 2003/0144708 A1 | 7/2003 | Starkebaum | |
| 2003/0144709 A1 | 7/2003 | Zabara et al. | |
| 2003/0158583 A1 | 8/2003 | Burnett et al. | |
| 2003/0181958 A1 | 9/2003 | Dobak | |
| 2004/0024428 A1 | 2/2004 | Barrett et al. | |
| 2004/0039427 A1 | 2/2004 | Barrett et al. | |
| 2004/0111118 A1 | 6/2004 | Hill et al. | |
| 2004/0162594 A1 | 8/2004 | King | |
| 2004/0193229 A1 | 9/2004 | Starkebaum et al. | |
| 2004/0230255 A1 | 11/2004 | Dobak | |
| 2004/0236381 A1 | 11/2004 | Dinsmoor et al. | |
| 2004/0236382 A1 | 11/2004 | Dinsmoor et al. | |
| 2004/0248188 A1 | 12/2004 | Sanders | |
| 2005/0003976 A1 | 1/2005 | Haze et al. | |
| 2005/0021092 A1 | 1/2005 | Yun et al. | |
| 2005/0021101 A1 | 1/2005 | Chen et al. | |
| 2005/0049655 A1 | 3/2005 | Boveja et al. | |
| 2005/0065562 A1 | 3/2005 | Rezai | |
| 2005/0065573 A1 | 3/2005 | Rezai | |
| 2005/0065575 A1 | 3/2005 | Dobak | |
| 2005/0070974 A1 | 3/2005 | Knudson et al. | |
| 2005/0075678 A1 | 4/2005 | Faul | |
| 2005/0131486 A1 | 6/2005 | Boveja et al. | |
| 2005/0131487 A1 | 6/2005 | Boveja et al. | |
| 2005/0137644 A1 | 6/2005 | Boveja et al. | |
| 2005/0158264 A1 | 7/2005 | Haze et al. | |
| 2005/0222635 A1 | 10/2005 | Krakovsky | |
| 2005/0222637 A1 | 10/2005 | Chen | |
| 2005/0245986 A1 | 11/2005 | Starkebaum | |
| 2006/0004414 A1 | 1/2006 | Chen | |
| 2006/0052826 A1 | 3/2006 | Kim et al. | |
| 2006/0052827 A1 | 3/2006 | Kim et al. | |
| 2006/0052828 A1 | 3/2006 | Kim et al. | |
| 2006/0052835 A1 | 3/2006 | Kim et al. | |
| 2006/0052836 A1 | 3/2006 | Kim et al. | |
| 2006/0052837 A1 | 3/2006 | Kim et al. | |
| 2006/0052838 A1 | 3/2006 | Kim et al. | |
| 2006/0052839 A1 | 3/2006 | Kim et al. | |
| 2006/0052856 A1 | 3/2006 | Kim et al. | |
| 2006/0058376 A1 | 3/2006 | Moritani et al. | |
| 2006/0074450 A1 | 4/2006 | Boveja et al. | |
| 2006/0085046 A1 | 4/2006 | Rezai et al. | |
| 2006/0089571 A1 | 4/2006 | Gertner | |
| 2006/0095088 A1 | 5/2006 | De Ridder | |
| 2006/0111754 A1 | 5/2006 | Rezai et al. | |
| 2006/0116736 A1 | 6/2006 | DiLorenzo | |
| 2006/0116737 A1 | 6/2006 | Libbus | |
| 2006/0129028 A1 | 6/2006 | Krakousky | |
| 2006/0129201 A1 | 6/2006 | Lee et al. | |
| 2006/0155344 A1 | 7/2006 | Rezai et al. | |
| 2006/0161217 A1 | 7/2006 | Jaax et al. | |
| 2006/0167498 A1 | 7/2006 | DiLorenzo | |
| 2006/0190053 A1 | 8/2006 | Dobak | |
| 2006/0229274 A1 | 10/2006 | Hsue | |
| 2006/0247718 A1 | 11/2006 | Starkebaum | |
| 2006/0247719 A1 | 11/2006 | Maschino et al. | |
| 2006/0247721 A1 | 11/2006 | Maschino et al. | |
| 2006/0247722 A1 | 11/2006 | Maschino et al. | |
| 2006/0259077 A1 | 11/2006 | Pardo et al. | |
| 2007/0025608 A1 | 2/2007 | Armstrong | |
| 2007/0027483 A1 | 2/2007 | Maschino et al. | |
| 2007/0027486 A1 | 2/2007 | Armstrong | |
| 2007/0027497 A1 | 2/2007 | Parnis | |
| 2007/0093870 A1 | 4/2007 | Maschino | |
| 2007/0106337 A1 | 5/2007 | Errico et al. | |
| 2007/0106338 A1 | 5/2007 | Errico | |
| 2007/0106339 A1 | 5/2007 | Errico et al. | |
| 2007/0135846 A1 | 6/2007 | Knudson et al. | |
| 2007/0162084 A1 | 7/2007 | Chen et al. | |
| 2007/0162085 A1 | 7/2007 | DiLorenzo | |
| 2007/0203521 A1 | 8/2007 | Dobak et al. | |
| 2007/0203531 A9 | 8/2007 | Starkebaum | |
| 2007/0219596 A1 | 9/2007 | Dobak | |
| 2007/0225768 A1 | 9/2007 | Dobak | |
| 2008/0009913 A1 | 1/2008 | Errico et al. | |
| 2008/0033511 A1 | 2/2008 | Dobak | |
| 2008/0058878 A1 | 3/2008 | King | |
| 2008/0086182 A1 | 4/2008 | Ben-David et al. | |
| 2008/0132968 A1 | 6/2008 | Starkebaum | |
| 2008/0147137 A1 | 6/2008 | Cohen et al. | |
| 2008/0147139 A1 | 6/2008 | Barrett et al. | |
| 2008/0167695 A1 | 7/2008 | Tehrani et al. | |
| 2008/0183237 A1 | 7/2008 | Errico et al. | |
| 2008/0208266 A1 | 8/2008 | Lesser et al. | |
| 2008/0262411 A1 | 10/2008 | Dobak | |
| 2008/0269833 A1 | 10/2008 | Scott et al. | |
| 2008/0269834 A1 | 10/2008 | Byerman et al. | |
| 2008/0281372 A1 | 11/2008 | Libbus et al. | |
| 2008/0293830 A1 | 11/2008 | Katagiri et al. | |
| 2008/0319274 A1 | 12/2008 | Ballegaard et al. | |
| 2009/0118777 A1 | 5/2009 | Iki et al. | |
| 2009/0118780 A1 | 5/2009 | DiLorenzo | |

OTHER PUBLICATIONS

Texas Instruments—Endoscope, date unknown, 3 pages.
PCT Search Report, International Application No. PCT/US2007/083519, dated May 23, 2008.
Canadian Office Action for Application No. 2,668,098 dated May 11, 2010.

* cited by examiner

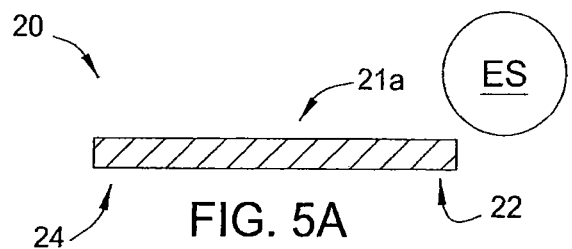
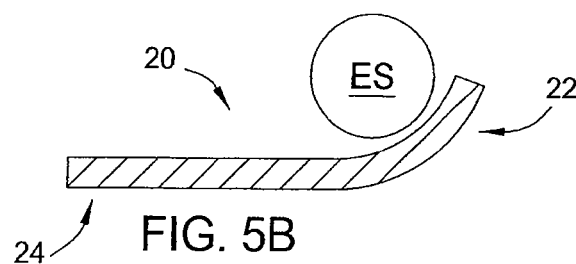
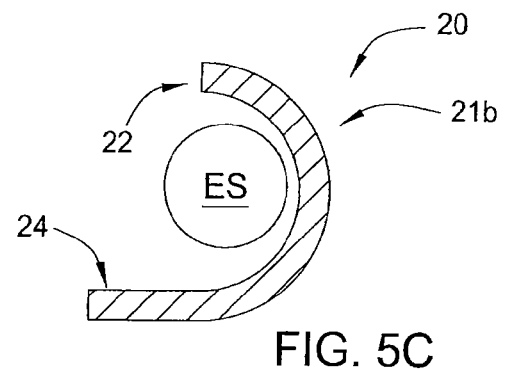
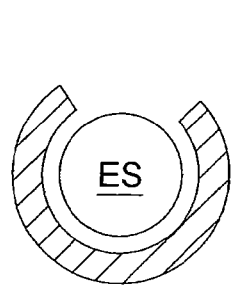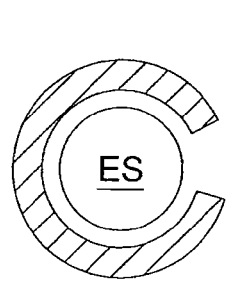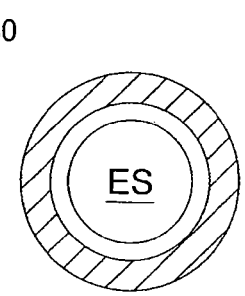
FIG. 6A     FIG. 6B     FIG. 6C

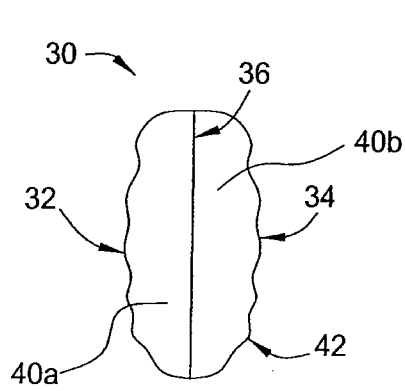
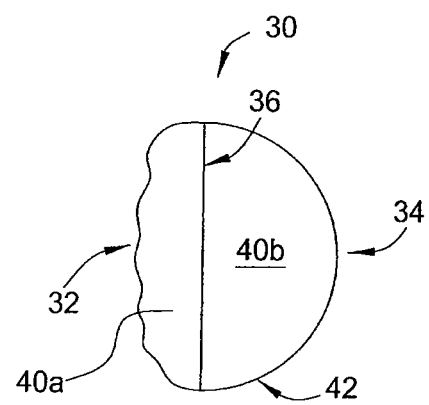
FIG. 13A          FIG. 13B
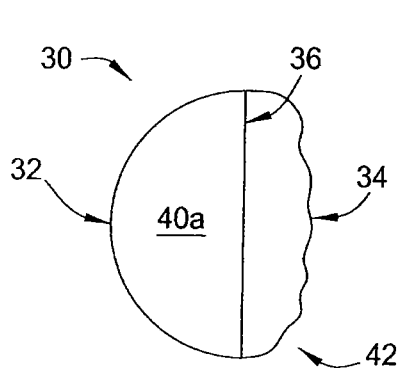
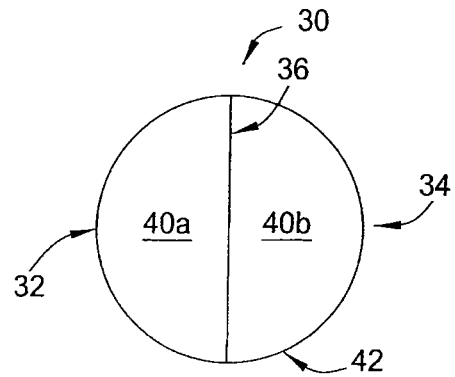
FIG. 13C          FIG. 13D

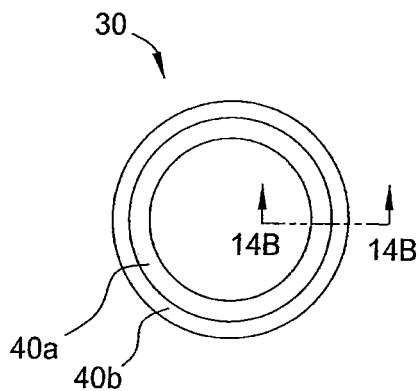
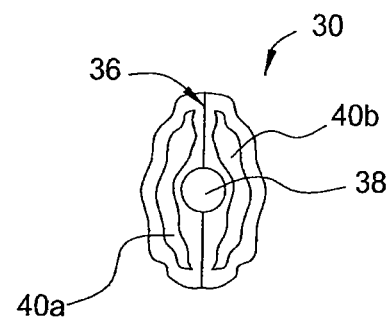
FIG. 14A  FIG. 14B
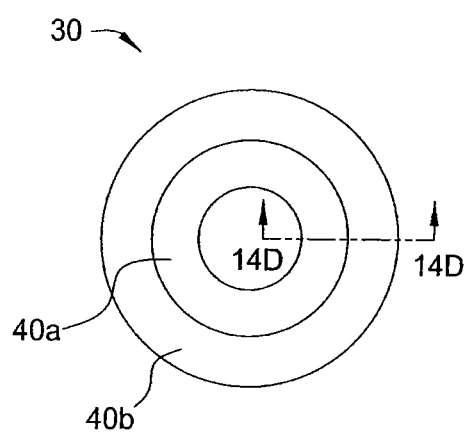
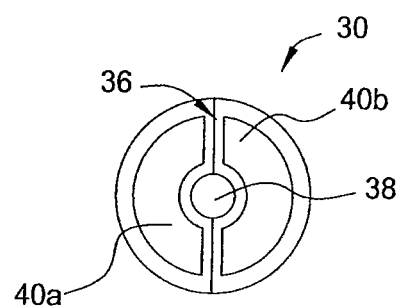
FIG. 14C  FIG. 14D

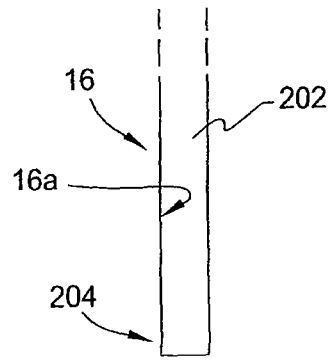
FIG. 34A
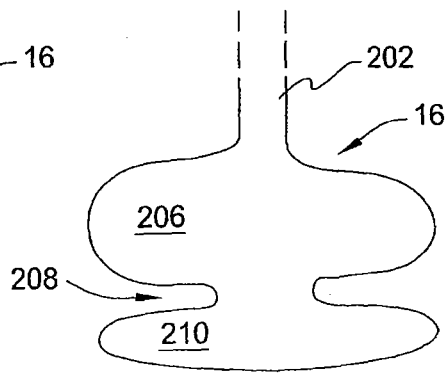
FIG. 34B
FIG. 34C
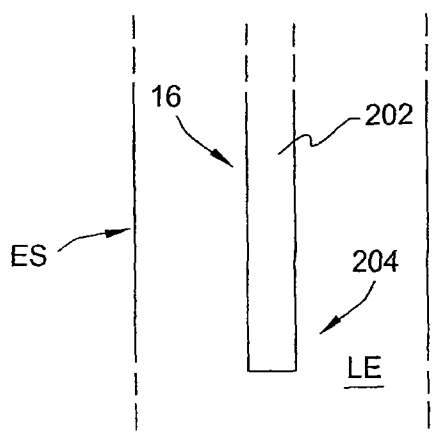
FIG. 35A
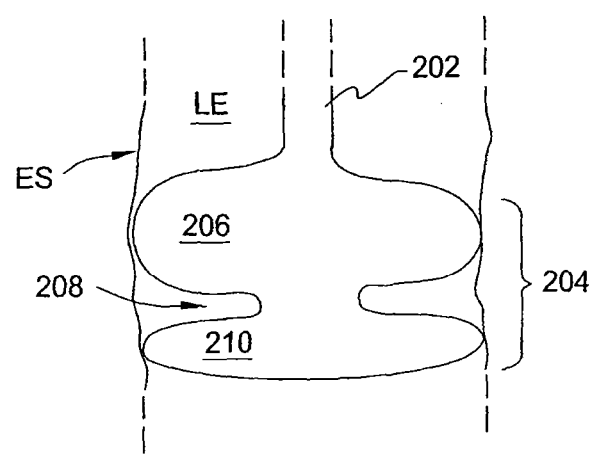
FIG. 35B

APPARATUS AND METHODS FOR MINIMALLY INVASIVE OBESITY TREATMENT

CROSS-REFERENCE TO RELATED APPLICATIONS

This application claims benefit of U.S. Provisional Patent Application Ser. No. 60/864,345, filed Nov. 3, 2006, which application is herein incorporated by reference in its entirety.

BACKGROUND OF THE INVENTION

1. Field of the Invention

The present invention generally relates to apparatus and methods for minimally invasive treatment of obesity.

2. Description of the Related Art

Obesity is a major health concern in many countries and is particularly prevalent in developed countries. Almost one-third of the adult American population is considered to be obese, while almost two-thirds of adult Americans are categorized as being obese or overweight. The number of overweight and obese Americans has continued to increase since 1960. Obesity is now an increasingly common health concern that affects many teenagers and children as well as adults.

Obesity is also a risk factor for a broad range of diseases and conditions, including diabetes, coronary artery disease, sleep apnea, gastro-esophageal reflux disease (GERD), and cancer of the breast, prostate and colon. As a result, obesity adds enormously to the costs of healthcare in the U.S. GERD is a very common condition, in which the contents of the stomach are refluxed into the esophagus. Unlike the stomach, the esophagus lacks protection from stomach acid and is prone to damage by the stomach contents. GERD is particularly common in obese individuals.

Each year, obesity causes at least 300,000 excess deaths in the U.S., and healthcare costs of American adults with obesity amount to approximately $100 billion. Furthermore, obese individuals may become victims of discrimination in employment and social settings leading to inferior lifestyle, lower socio-economic status, and possible psychological and mental health problems.

Treatment regimes for obesity have included various diets, exercise programs, and lifestyle counseling, as well as pharmaceutical compositions and surgery. Numerous surgical procedures for the treatment of obesity are known in the prior art. One surgical approach to obesity treatment is gastric bypass surgery, which leads to decreased nutrient absorption by the patient. Another approach to the treatment of obesity is the insertion of an intra-gastric balloon to mimic fullness of the stomach. A further approach is the application of a band around the stomach wall to restrict gastric volume. Yet another approach is the insertion of an intraluminal filter or valve at the gastro-esophageal junction to restrict passage of food into the stomach. Still another approach is the direct electrical stimulation of the stomach wall to decrease the normal peristaltic motility of the stomach.

The procedures outlined above have generally been of limited value, and in addition have various disadvantages. For example, insertion of an intra-gastric balloon in the stomach is invasive and may have serious side effects, e.g., by interfering with the digestion of food. Similarly, various gastric bypass procedures, in which a portion of the gastro-intestinal tract is surgically excised, have led to under-nourished or malnourished patients, and furthermore such procedures are typically highly invasive and irreversible.

Jakabsson et al. (U.S. Pat. No. 6,102,922) disclose a food intake restriction device that includes a substantially non-expansible outer wall and an expansible inner wall. Jakabsson et al. further disclose a method in which a band of the device is looped around the esophagus and stomach such that a small stomach pouch is formed by displacing an upper part of the stomach through the loop. The band is tunnelated by suturing the upper part of the stomach to the portion of the stomach situated below the band. The pouch typically greatly expands in the course of time, normally reaching up to ten times its original size after about a year.

Forsell (US 2001/0011543) discloses apparatus for controlling food flow in a patient, the apparatus including a restriction member having two separate chambers, wherein fluid is pumped from one chamber to the other chamber to change the size of a stoma opening of the restriction member.

Barrett et al. (U.S. Pat. No. 6,587,719) disclose treatment of obesity by bilateral electrical stimulation of the right and left vagal nerve at a location in the patient's thorax. Implanted bilateral nerve stimulators or, in a clinical setting external stimulator devices, provide the electrical stimulation.

As can be seen, there is a need for apparatus, systems, and methods for the safe, reliable, cost-effective, and minimally invasive treatment of obesity. There is a further need for apparatus and methods for the effective and minimally invasive treatment of GERD.

SUMMARY OF THE INVENTION

The present invention provides systems, apparatus, and methods for the effective and minimally invasive treatment of obesity. The present invention also provides apparatus and methods for the treatment of gastro-esophageal reflux disease (GERD). In an embodiment the invention provides an implantable device for treatment of the patient. The device is adjustable (e.g., expandable) in at least one dimension for exerting of a suitable mechanical force on one or more tissues or organs targeted for treatment. Expansion of the device is controllable for adjusting the mechanical force.

In various embodiments, apparatus of the invention is configured for mechanical and/or electrical neuromodulation of nerve tissue(s) strategically targeted for treatment of obesity and/or GERD. In an embodiment the invention provides an introducer element for introduction of the implantable device into the patient. The invention further provides an intraluminal guide for guiding placement of the implantable device in the patient.

In one aspect of the present invention, there is provided a device comprising at least one curved portion, wherein the device is configured for radially outward expansion of the curved portion independently of radially inward expansion of the curved portion, and the curved portion is configured for at least partially encircling the esophagus of a patient.

In another aspect of the present invention, there is provided a device for implantation within a patient via an introducer element, the device having a substantially linear conformation. The device is configured for adopting the linear conformation when the device is disposed within a shaft of the introducer element. The device is further configured for adopting a substantially arcuate conformation when the device is implanted in the patient, and the device includes an expandable curved portion formed from the arcuate conformation. The curved portion is configured for encircling the esophagus of the patient, and the curved portion has an internal diameter and an external diameter. The curved portion is configured for adjusting the external diameter independently of adjustment of the internal diameter. The curved portion includes first and second independently expandable elements, wherein the first expandable element is configured for adjusting the internal diameter independently of the external diameter, and the second expandable element is configured for adjusting the external diameter independently of the internal diameter.

According to another aspect of the present invention, an apparatus comprises a device including at least one curved portion having a radially outer surface, and a radially inner surface. The device is configured for radially outward expansion of the radially outer surface and for radially inward expansion of the radially inner surface. The curved portion is configured for at least partially encircling the esophagus of a patient, and the radially outward expansion is independent of the radially inward expansion.

In yet another aspect of the present invention, a device for treating a patient comprises at least one curved portion, wherein the device is transformable from a linear conformation to an arcuate conformation. The device is configured for at least partially encircling the esophagus of the patient, the device is configured for transforming the linear conformation to the arcuate conformation by pushing the device sub-fascially around the esophagus, and the arcuate conformation forms the curved portion.

In still another aspect of the present invention, there is provided a device comprising at least one curved portion, wherein the curved portion comprises a plurality of interconnectable segments. The curved portion is at least substantially C-shaped, O-shaped, or U-shaped, and the curved portion is configured for at least partially encircling the esophagus of a patient.

In a further aspect, the present invention provides a device including at least one curved portion having at least one expandable element for expanding the curved portion in at least one dimension, and at least one electrode disposed on the curved portion. The device is configured for at least partially encircling the esophagus of a patient, and the device is further configured for making electrical contact with a targeted nerve tissue of the patient.

According to another aspect of the present invention, there is provided apparatus for treating an obesity patient, wherein the apparatus comprises a surgically implantable device including a curved portion configured for placement around the esophagus of the patient. The curved portion includes a first end and a second end, a radially outer surface defining an external diameter, and a radially inner surface defining an internal diameter. The curved portion is cannulated to provide a bore therethrough. The apparatus further includes a filament disposed within the bore, and a collar configured for slidably accommodating a first strand and a second strand of the filament. The device is configured for adjusting the internal diameter and the external diameter of the curved portion by passage of at least one of the first strand and the second strand within the collar.

According to yet another aspect of the present invention, there is provided an intraluminal guide for treating a patient, the intraluminal guide comprising a distal end portion including a distal expansion chamber, a proximal expansion chamber, and a waist portion, wherein the waist portion disposed between the distal expansion chamber and the proximal expansion chamber. The intraluminal guide further comprises a channel in fluid communication with the distal end portion for expanding the distal expansion chamber and the proximal expansion chamber, wherein the channel extends proximally from the proximal expansion chamber. An unexpanded conformation of the distal end portion is configured for intraluminal passage within the esophagus. The distal expansion chamber and the proximal expansion chamber are configured for intraluminal expansion within the esophagus.

In another aspect of the present invention, there is provided a system comprising an introducer element including a shaft, an implantable device, and an intraluminal guide for guiding placement of the device within a patient. The introducer element is adapted for insertion of a distal end of the shaft into the thorax or abdomen of the patient. The device is adapted for passage within the shaft, and the device is configured for adopting a substantially linear conformation when the device is disposed within the shaft. The device is further configured for adopting a substantially arcuate conformation when the device is implanted in the patient. The device includes an expandable curved portion formed from the arcuate conformation, and the curved portion is configured for at least partially encircling the esophagus of the patient. The intraluminal guide includes an expandable distal end portion. An unexpanded conformation of the distal end portion is configured for intraluminal passage within the esophagus, and the distal end portion is configured for intraluminal expansion within the esophagus and for guiding placement of the device around the esophagus of the patient.

According to another aspect of the present invention, there is provided a method for treating a patient, the method comprising placing a device extraluminally with respect to the esophagus such that the device at least partially encircles the esophagus, wherein the device includes a curved portion configured for radially outward expansion thereof, and the radially outward expansion is independent of any radially inward expansion of the curved portion; and expanding the curved portion in at least one dimension, such that a surface of the curved portion exerts a mechanical force on at least one tissue or organ of the patient.

In another aspect of the present invention, there is provided a method comprising advancing a linear conformation of a device sub-fascially around the esophagus of a patient, whereby the linear conformation is transformed to an arcuate conformation; and disposing the arcuate conformation beneath the diaphragmatic fascia at the distal esophagus.

In still a further aspect of the present invention, there is provided a method comprising placing a device around the esophagus such that the device at least partially encircles the esophagus of a patient, wherein the device includes a curved portion comprising a radially outer surface and a radially inner surface. The device is configured for radially outward expansion of the radially outer surface, the device is further configured for radially inward expansion of the radially inner surface, and the radially outward expansion is independent of the radially inward expansion. The method further comprises expanding at least one of the radially outer surface and the radially inner surface sufficient to exert a mechanical force on at least one nerve tissue of the patient; and, via the mechanical force, mechanically neuromodulating the nerve tissue.

In yet another aspect of the present invention, there is provided a method comprising placing a device around the esophagus such that the device at least partially encircles the esophagus; and, via the device, mechanically neuromodulating at least one nerve tissue of the patient.

According to still another aspect of the present invention, there is provided a method comprising placing a device at the distal esophagus of a patient; via the device, mechanically blocking a first nerve tissue, wherein the first nerve tissue is blocked via exertion of a mechanical force by the device on the first nerve tissue; and via the device, mechanically stimulating a second nerve tissue, wherein the stimulating induces a sensation of satiety in the patient. The first nerve tissue innervates the stomach, and blocking the first nerve tissue decreases at least one of: i) gastric motility, ii) gastric acid production, and iii) gastric enzyme production.

In a further aspect of the present invention, there is provided a method comprising advancing a first segment of a device from a first side of a patient's body towards a first side of the patient's esophagus; advancing a second segment of the device from a second side of the patient's body towards a second side of the patient's esophagus; at least partially encircling the esophagus with at least one of the first segment and the second segment; and coupling the first and second segments.

In another aspect of the present invention, there is provided a method comprising placing a device around the esophagus of a patient such that the device at least partially encircles the esophagus of the patient. The device includes a curved portion configured for transformation between an expanded configuration and an unexpanded configuration, and at least one electrode disposed on the curved portion. The method further comprises, via the electrode, applying an electrical signal to at least one nerve tissue sufficient to electrically neuromodulate the nerve tissue.

In yet another aspect of the present invention, there is provided a method for treating obesity in a patient, the method comprising disposing a device beneath the diaphragmatic fascia of the patient; advancing the device sub-fascially towards the distal esophagus such that the device at least partially encircles the esophagus; and retaining the device in situ around the esophagus via a fascial layer of the patient.

In still another aspect of the present invention, there is provided a method for treating gastro-esophageal reflux disease comprising implanting a device beneath the diaphragmatic fascia of the patient; disposing the device sub-fascially at the distal end of the esophagus; and disposing the device extraluminally around the esophagus, wherein the device inhibits reflux from the stomach into the esophagus.

In another aspect of the present invention, there is provided a method comprising placing a device extraluminally with respect to the esophagus such that the device at least partially encircles the esophagus of the patient, wherein the device includes a curved portion configured for exerting a mechanical force on at least one tissue or organ via adjustment of a diameter of the curved portion. The curved portion is cannulated to allow passage of a filament therethrough. The device further includes a collar configured for slidably accommodating a first strand and a second strand of the filament. The device is configured for adjusting a diameter of the curved portion by passage of at least one of the first strand and the second strand within the collar. The method further comprises adjusting the diameter of the curved portion.

According to another aspect of the present invention, there is provided a method comprising passing an intraluminal guide intraluminally within the esophagus to the distal esophagus of the patient. The intraluminal guide includes an expandable distal end portion having a waist portion. The method further comprises introducing an extraluminal constriction device into the thorax or abdomen of the patient and to a location in at least close proximity to the gastro-esophageal junction; at least partially expanding the distal end portion intraluminally within the esophagus; and advancing the device extraluminally with respect to the esophagus and around the waist portion such that the device at least partially encircles the distal esophagus.

These and other features, aspects, and advantages of the present invention will become better understood with reference to the following drawings, description, and claims.

BRIEF DESCRIPTION OF THE DRAWINGS

FIGS. 5A-C schematically represent transformation of a linear conformation to an arcuate conformation of a device, according to another embodiment of the invention;

FIGS. 6A-C schematically represent substantially U-shaped, C-shaped, and O-shaped configurations, respectively, of a curved portion of a device, shown in relation to a horizontal section through the esophagus, according to three additional embodiments of the invention;

FIGS. 13A-D are sectional views also taken along the lines 12A-12A, 12B-12B, 12C-12C, and 12D-12D, respectively of FIGS. 11A-D, showing expandable elements integral with the wall of the curved portion, according to another embodiment of the invention;

FIG. 14A is a plan view of a curved portion of a device in an unexpanded configuration, according to one embodiment of the invention;

FIG. 14B is a sectional view, taken along the lines 14B-14B of FIG. 14A, showing a bore within the curved portion;

FIG. 14C is a plan view of the curved portion of FIG. 14A in an expanded configuration;

FIG. 14D is a sectional view, taken along the lines 14D-14D of FIG. 14C;

FIGS. 34A-C are side views schematically representing unexpanded, partially expanded, and expanded configurations, respectively, of an intraluminal guide, according to an embodiment of the invention;

FIGS. 35A-B schematically represent unexpanded and expanded configurations, respectively, of the intraluminal guide of FIGS. 34A-C with the guide disposed intraluminally in relation to the esophagus, according to the invention;

DETAILED DESCRIPTION OF THE INVENTION

Figure 1:
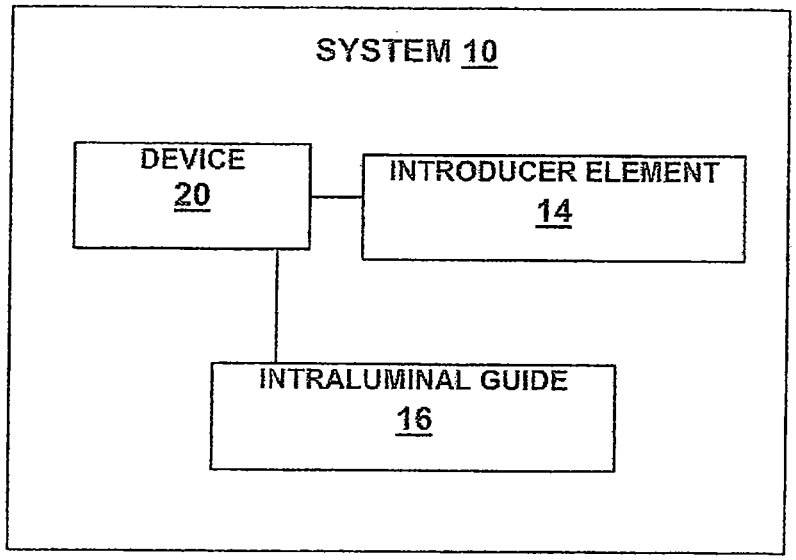
FIG. 1 is a block diagram schematically representing a system for treating a patient, according an embodiment of the invention.

The detailed description that follows is not to be taken in a limiting sense, but is made primarily for the purpose of illustrating the general principles of the various aspects of the present invention. The scope of the invention is best defined by the claims appended hereto.

Broadly, the present invention provides systems, apparatus, and methods for treating conditions related to the gastro-intestinal (GI) tract, such as obesity and gastro-esophageal reflux disease (GERD). In one aspect, the present invention provides an implantable device for treating an obesity patient. In another aspect, the present invention provides a system including an introducer element for introducing the device into the patient's body. In another aspect, the present invention provides apparatus including an intraluminal guide for guiding placement of the device within the patient.

In an embodiment, the device may be implanted sub-fascially within esophageal tissue at the distal esophagus. In an embodiment, treatment of the patient may be effected by neuromodulation of nerve tissue, for example, by mechanical or electrical neuromodulation of targeted sensory or motor nerve tissue. Neuromodulation, either by blocking or stimulating transmission of neural impulses, may be induced electrically via application of electrical signals to the nerve tissue or mechanically by exertion of a suitable mechanical force on the nerve tissue.

In contrast to prior art apparatus and methods, a device of the instant invention for the treatment of obesity may be placed extraluminally and sub-fascially at the distal esophagus of a patient. According to one aspect of the instant invention, and in further contrast to the prior art, an implantable device may be transformed from a linear conformation to an arcuate conformation as a result of sub-fascial advancement around the esophagus; in the absence of such sub-fascial placement the device will tend to remain in the linear conformation. In an embodiment, a device of the instant invention for the treatment of obesity may be embedded within esophageal tissue. In further contrast to the prior art, a device of the instant invention for the treatment of obesity may be disposed sub-fascially and extraluminally at the distal esophagus such that the device does not contact the stomach of the patient.

In further contrast to the prior art, a device of the instant invention for the treatment of obesity may comprise a plurality of interconnectable arcuate segments. In still further contrast to the prior art, a device of the instant invention for the treatment of obesity includes a curved portion configured for radial outward expansion independently of any radially inward expansion of the curved portion. In further contrast to the prior art, a device of the instant invention is configured for adopting an expanded configuration when implanted in a patient, wherein the device includes at least one electrode on an expandable curved portion of the device, and wherein expansion of the curved portion urges the electrode(s) into electrical contact with a targeted tissue of the patient. In yet further contrast to the prior art, a device of the instant invention for the treatment of obesity may be guided to a targeted location within the patient via an expandable intraluminal guide.

With reference to the drawings, FIG. 1 is a block diagram schematically representing a system 10 for treating a patient, according to one aspect of the present invention. System 10 includes a device 20, an introducer element 14, and an intraluminal guide 16. System 10 may be used for treating a patient for a condition involving the GI tract. For example, system 10 may be used for treating an obesity patient. In other embodiments, system 10 may be used for treating GERD. Device 20 may be configured for at least partially encircling the esophagus of a patient. Device 20 may be introduced into the patient via introducer element 14. For example, device 20 may be introduced, via introducer element 14, to a location in at least close proximity to the gastro-esophageal junction (GEJ) of the patient.

In an embodiment, device 20 may be advanced sub-fascially, from introducer element 14, around the distal esophagus of the patient for extraluminal placement of device 20 with respect to the esophagus. In contrast, intraluminal guide 16 may be configured for passage intraluminally within the esophagus to the distal esophagus. A distal end portion of intraluminal guide 16 may be expandable. An expanded configuration of intraluminal guide 16 may serve to guide advancement of device 20 extraluminally around the esophagus (see, e.g., FIGS. 35C and 36). Intraluminal guide 16 may include a light source for illuminating at least the distal end portion of intraluminal guide 16. An unexpanded configuration of intraluminal guide 16 may be withdrawn intraluminally from the patient after placement of device 20 around the esophagus.

Figure 2:
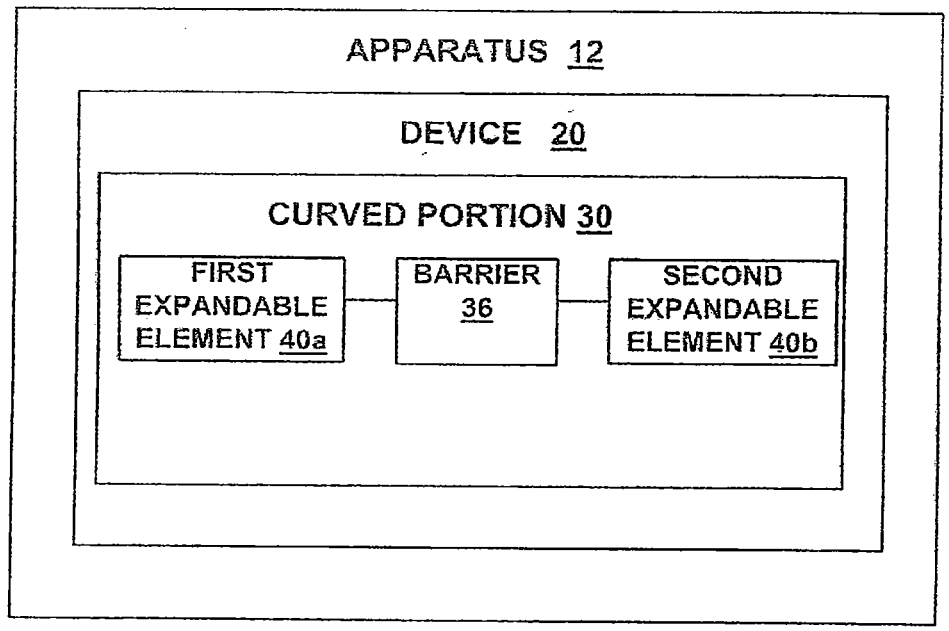
FIG. 2 is a block diagram schematically representing apparatus for treating a patient, according to another embodiment of the invention.

FIG. 2 is a block diagram schematically representing an apparatus 12 for treating a patient, according to an embodiment of the invention. Apparatus 12 includes a device 20 having a curved portion 30. Curved portion 30 includes a first expandable element 40a, a second expandable element 40b, and a barrier 36. Device 20 may be configured for transformation from a linear conformation to an arcuate conformation. Curved portion 30 may be configured for at least partially encircling the esophagus of a patient (see, e.g., FIGS. 24A-B).

In an embodiment, first expandable element 40a and second expandable element 40b may be expandable independently of each other. First expandable element 40a may be configured for radially inward expansion of curved portion 30. Second expandable element 40b may be configured for radially outward expansion of curved portion 30. Barrier 34 may be disposed between the first and second expandable elements. Typically, barrier 36 is at least substantially non-extensible, and barrier 36 may not extend radially inward or radially outward when one or both of first expandable element 40a and second expandable element 40b are expanded.

Figure 3:
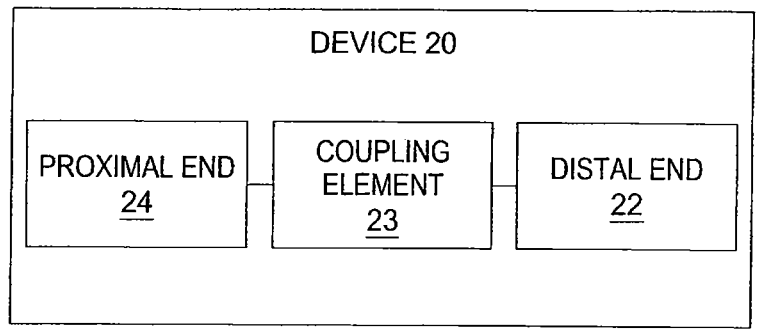
FIG. 3 is a block diagram schematically representing a device for treating a patient, according to another embodiment of the invention.

FIG. 3 is a block diagram schematically representing a device 20 for treating a patient, according to another embodiment of the invention. Device 20 includes a distal end 22, a proximal end 24, and a coupling unit 23. In an embodiment, distal end 22 and proximal end 24 may be coupled to each other via coupling unit 23. Typically, distal end 22 and proximal end 24 may be coupled to each other after placement of device 20 around the esophagus of the patient. As an example only, and not to limit the invention in any way, coupling unit 23 may comprise male and female parts, which may be arranged at distal end 22 and proximal end 24 of device 20 (see, e.g., FIGS. 4A-B).

Figure 4A:
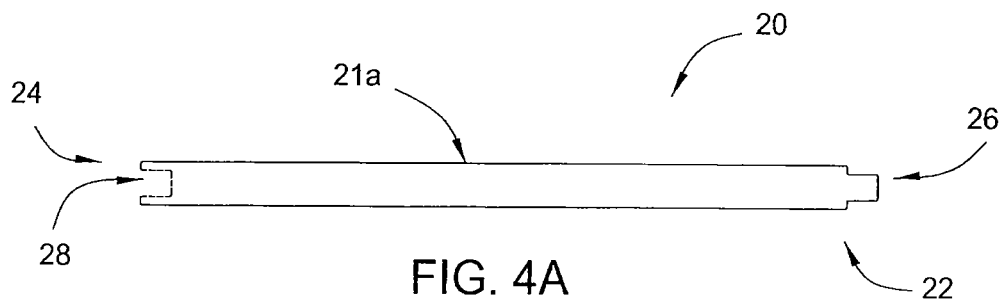
FIG. 4A schematically represents a linear conformation of a device for treating a patient, according to an embodiment of the invention.
Figure 4B:
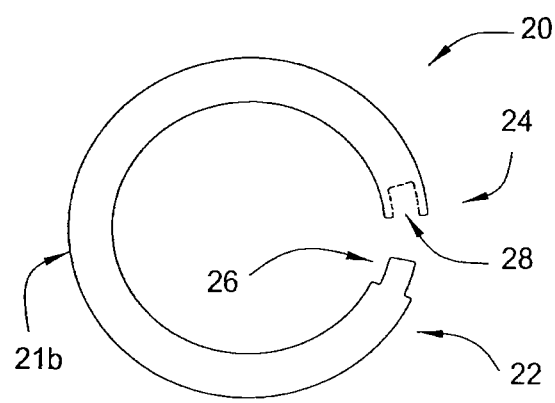
FIG. 4B schematically represents an arcuate conformation of the device of FIG. 4A.

FIG. 4A schematically represents a linear conformation 21a of a device 20 for treating a patient, according to an embodiment of the invention, and FIG. 4B schematically represents an arcuate conformation 21b of device 20 of FIG. 4A. With reference to FIGS. 4A-B, device 20 includes a male part 26 disposed at distal end 22, and a female part 28 disposed at proximal end 24, wherein in the arcuate conformation 21b, distal end 22 and proximal end 24 may be coupled to each other, as indicated in FIG. 4B. In an embodiment, the coupling of distal end 22 and proximal end 24 may provide a curved or at least substantially annular structure that may be referred to herein as curved portion 30 (see, for example, FIGS. 2, 6A-C, 11A-D, 14A-D, and 21).

Of course, numerous other mechanisms for coupling the ends of device 20 are known in the art, and the use of a particular coupling mechanism may be considered to be at least to some extent a matter of design choice. Naturally, all materials for coupling mechanisms and other apparatus according to the present invention may comprise biocompatible materials, or may be coated with such biocompatible materials. Device 20 of FIGS. 4A-B may comprise one or more of the embodiments of device 20, for example, as shown and described herein with reference to FIGS. 1-3, 8-9, 18, and 20. In addition, it is to be understood that various elements, features, and characteristics of the different embodiments may be combined in various combinations not inconsistent with the present invention as disclosed and claimed herein.

FIGS. 5A-C schematically represent transformation of a linear conformation 21a to an arcuate conformation 21b of a device 20 for treating a patient, according to another embodiment of the invention. FIG. 5A represents linear conformation 21a, having a distal end 22 and a proximal end 24, in relation to the esophagus, ES, of the patient (the esophagus is represented in FIGS. 5A-C in horizontal section). FIG. 5B shows arcing of distal end 22 during advancement around the esophagus. In an embodiment, device 20 may be advanced around the esophagus sub-fascially, for example, beneath the diaphragmatic fascia (see, e.g., FIG. 25). FIG. 5C shows device 20 adopting arcuate conformation 21b as distal end 22 is further advanced around the esophagus of the patient. The partial or complete transformation of linear conformation 21a to arcuate conformation 21b results in the formation of curved portion 30 of device 20 (see, e.g., FIGS. 6A-C, 7A-C).

FIGS. 6A-C each schematically represents a curved portion 30 of a device for treating a patient, according to three additional embodiments of the invention. Curved portion 30 of FIGS. 6A-C may be described as substantially U-shaped, C-shaped, and O-shaped, respectively. Each of the configurations of curved portion 30 is shown in relation to the esophagus, ES. The esophagus is again represented in horizontal section in FIGS. 6A-C. It can be seen that curved portion 30 may at least partially, or fully, encircle the esophagus of the patient.

Figure 7A:
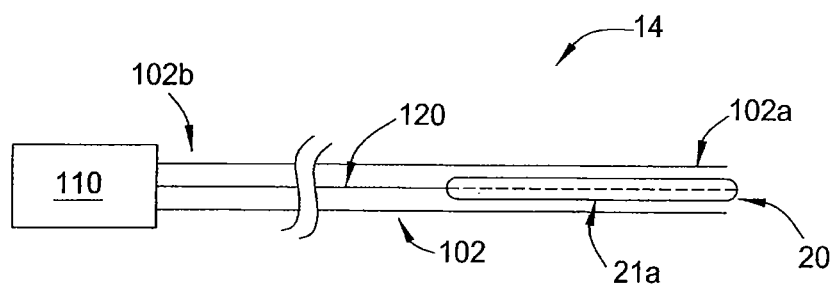
FIG. 7A schematically represents a linear conformation of a device in relation to an introducer element for introducing the device into a patient, according to one embodiment of the invention.

FIG. 7A is a schematic representation showing a linear conformation 21a of a device 20 in relation to an introducer element 14, according to one aspect of the present invention. Introducer element 14 may include a shaft 102 having a distal end 102a and a proximal end 102b. Introducer element 14 may further include a handpiece 110 at proximal end 102b. Handpiece 110 may allow manipulation of shaft 102 and provide control for various functions required by a surgeon, for example, during an endoscopic or laparoscopic procedure involving the introduction of device 20 into the patient's body. Introducer element 14 is configured for passage of linear conformation 21a within shaft 102 and into a patient. For example, shaft 102 may provide a working channel, e.g., for the passage therethrough of linear conformation 21a, whereby device 20 may be introduced into the patient and disposed at the distal esophagus. Linear conformation 21a may be passed within shaft 102 and guided within the patient's body via a guidewire 120. Shaft 102 may also provide for introduction of a light source, inflation fluid, and the like to the surgical site.

Figure 7B:
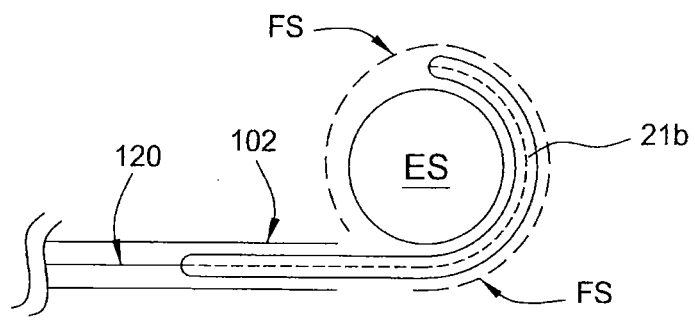
FIGS. 7B-C schematically represent stages of advancing an arcuate conformation of the device of FIG. 7A from the introducer element and around the esophagus of a patient, according to another embodiment of the invention.
Figure 7C:
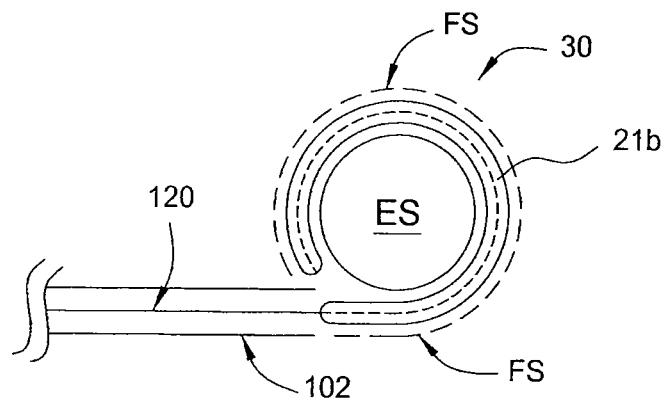

FIG. 7B shows advancement of an arcuate conformation 21b of device 20 from shaft distal end 102a of introducer element 14 and around the esophagus, ES, of the patient. According to one aspect of the instant invention, device 20 is advanced sub-fascially around the esophagus. That is to say, in an embodiment of the present invention, in a procedure for placing device 20 around the distal esophagus, device 20 may be implanted beneath the fascia, FS; and thereafter, device 20 may be advanced beneath the fascia surrounding the muscular layers of the esophagus, such that device 20 is disposed sub-fascially and extraluminally with respect to the esophagus. Prior to implantation beneath the fascia, device 20 may be advanced supra-diaphragmatically, i.e., above the diaphragm of the patient. The fascia, FS, shown in FIGS. 7B-C may be the diaphragmatic fascia or an extension thereof. Other routes or paths for placement of device 20 are also contemplated under the instant invention. Device 20 may be implanted beneath the fascia while device 20 is in linear conformation 21a. The arcuate conformation 21b of FIG. 7C may result from the advancement of linear conformation 21a around the esophagus. Arcuate conformation 21b forms curved portion 30, the latter being shown in FIG. 7C as disposed sub-fascially and extraluminally around the esophagus. According to one aspect of the present invention, device 20 may be implanted in the patient such that not even an expanded configuration of curved portion 30 (see, e.g., FIGS. 11A-D), contacts the stomach, ST, of the patient (see, e.g., FIGS. 24A-B and 28-29).

Figure 8:
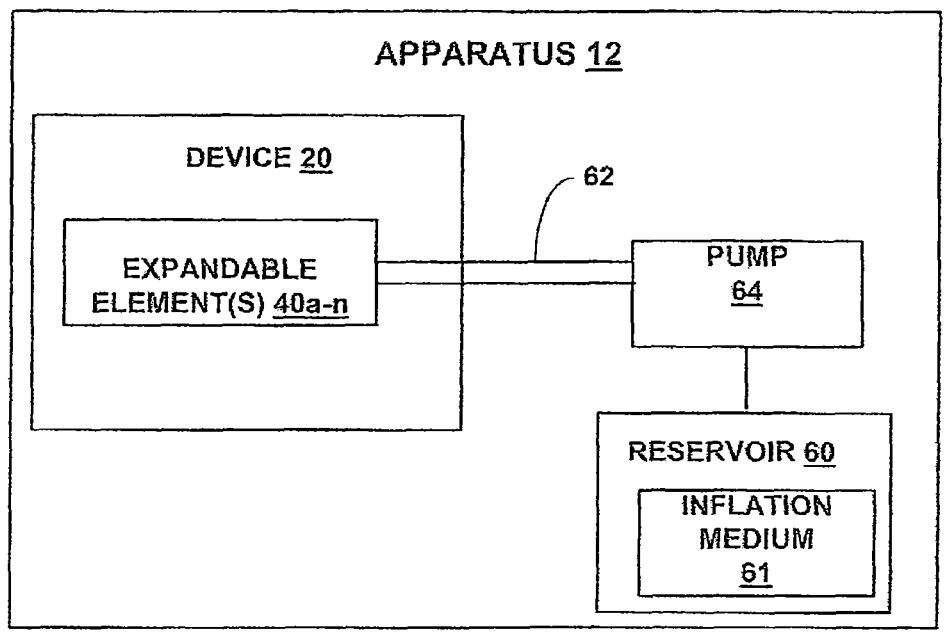
FIG. 8 is a block diagram schematically representing apparatus for treating a patient, according to another embodiment of the invention.

FIG. 8 is a block diagram schematically representing an apparatus 12 for treating a patient, according to another embodiment of the invention. In the embodiment of FIG. 8, apparatus 12 comprises a device 20 including one or more expandable elements 40*a-n*, a reservoir 60, a conduit 62, and a pump 64. Each of expandable elements 40*a-n* may comprise an inflatable member, such as a balloon. Reservoir 60 may contain a quantity of an inflation medium 61. Each of expandable elements 40*a-n* may be expanded by passing inflation medium 61 therein. Pump 64 may be in fluid communication with reservoir 60. Various implantable pumps and other mechanisms for pressurizing a fluid or similar medium are known in the art. Inflation medium 61 may be pumped from reservoir 60 to expandable elements 40*a-n* via conduit 62. As non-limiting examples, the inflation medium may comprise a fluid, such as a physiological saline, other aqueous liquids, a gel, or a gas, and the like.

Figure 9:
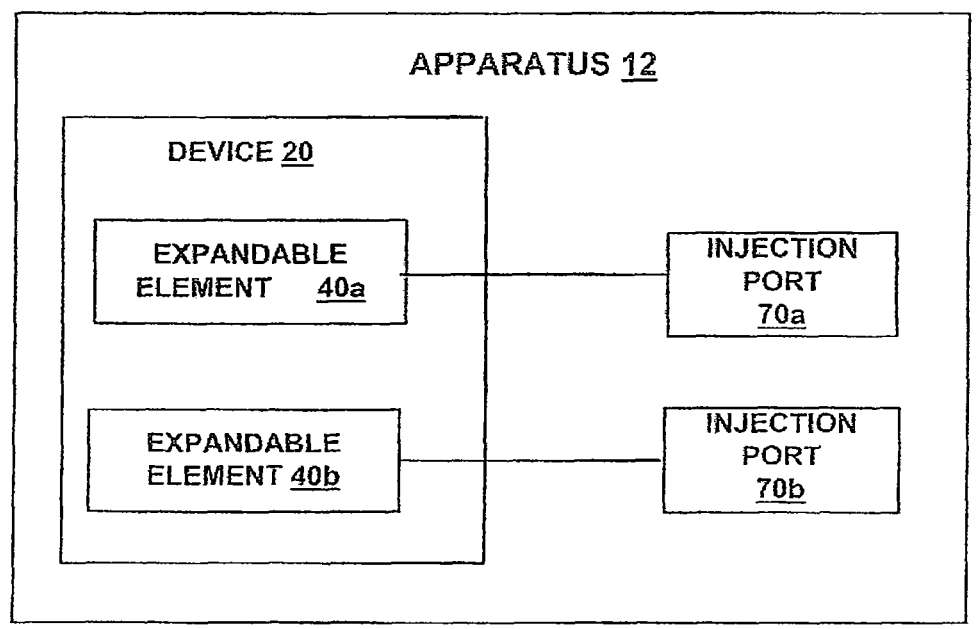
FIG. 9 is a block diagram schematically representing apparatus for treating a patient, according to another embodiment of the invention.

FIG. 9 is a block diagram schematically representing apparatus 12 for treating a patient, according to another embodiment of the invention. In the embodiment of FIG. 9, apparatus 12 comprises a device 20 including a plurality of expandable elements 40*a-n*, and a plurality of injection ports 70*a-n*. The number of injection ports 70*a-n* may correspond to the number of expandable elements 40*a-n*. In an embodiment, injection ports 70*a-n* may be implanted beneath the skin of the patient. Implantable injection ports for injection of fluids are well known in the art. Injection ports 70*a-n* may be palpated and accessed percutaneously by a surgeon or other medical personnel. Injection ports 70*a-n* may be coupled to a source of inflation medium, which may be pressurized, e.g., via a syringe or mechanical pump, for expansion of expandable elements 40*a-n*. Conversely, injection ports 70*a-n* may be accessed for removal of inflation medium and contraction of expandable elements 40*a-n*. Expansion of expandable elements 40*a-n* may exert a mechanical force on at least one tissue or organ of the patient. Such a mechanical force may be sufficient to effect treatment of the patient (see, e.g., FIGS. 30C, 31C, 45).

Figure 10:
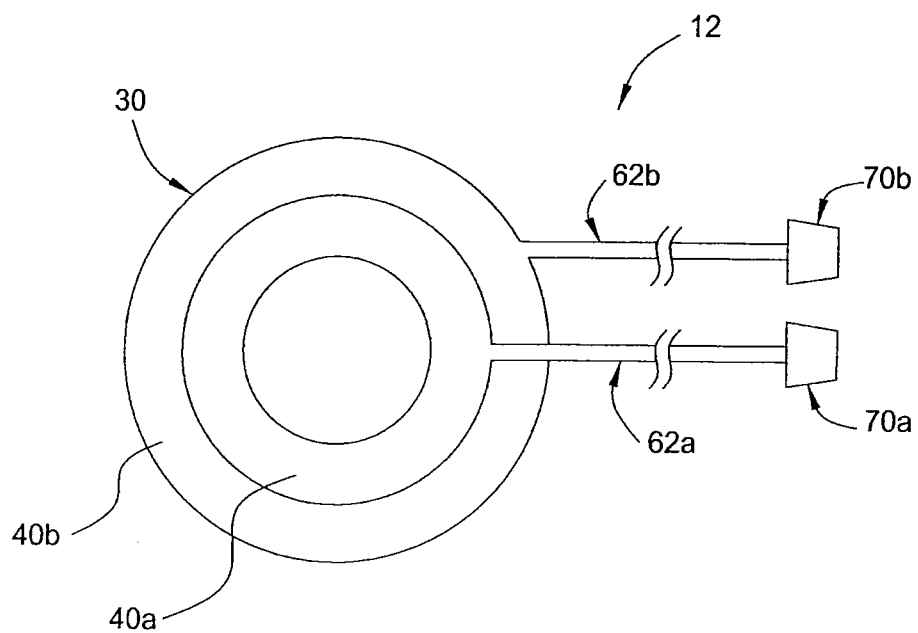
FIG. 10 schematically represents apparatus for treating a patient, according to another embodiment of the invention.

FIG. 10 schematically represents apparatus 12 for treating a patient, according to another embodiment of the invention. Apparatus 12 includes a curved portion 30, comprising a first expandable element 40*a* and a second expandable element 40*b*; first and second injection ports 70*a*, 70*b*, respectively; and first and second conduits, 62*a*, 62*b*, respectively. First and second expandable elements 40*a*, 40*b* are in fluid communication with first and second injection ports 70*a*, 70*b*, respectively, via first and second conduits, 62*a*, 62*b*, respectively. First expandable element 40*a* may have a lesser diameter and be located internal to second expandable element 40*b*. First expandable element 40*a* and second expandable element 40*b* may be substantially concentric.

Each of first and second expandable elements 40*a*, 40*b* may comprise an inflatable member, e.g., a balloon. First expandable element 40*a* may be expanded, or inflated, via passage of an inflation medium through first conduit 62*a*. Similarly, second expandable element 40*b* may be expanded, or inflated, via passage of an inflation medium through second conduit 62*b*. According to an aspect of the present invention, second expandable element 40*b* may be expanded to expand curved portion 30 radially outward in the substantial absence of any radially inward expansion of curved portion 30 (see, for example, FIGS. 11A-D). In another aspect of the present invention, first expandable element 40*a* may be expanded to expand curved portion 30 radially inward in the substantial absence of any radially outward expansion of curved portion 30.

FIGS. 11A-D each represent, in plan view, a different configuration of a curved portion 30 of a device for treating a patient, according to an embodiment of the invention. Curved portion 30 may be configured for expansion in at least one dimension. Curved portion 30 includes a first, inner expandable element 40*a* and a second, outer expandable element 40*b*. Curved portion 30 includes a radially inner surface 32 defining an internal diameter $D_I/D_I'$, and a radially outer surface 34 defining an external diameter $D_E/D_E'$. Radially outward expansion of curved portion 30 urges radially outer surface 34 radially outwards, while radially inward expansion of curved portion 30 urges radially inner surface 32 radially inwards. Thus, according to one aspect of the invention, radially inward expansion of curved portion 30 can decrease the internal diameter of curved portion 30 and at the same time exert a radially inward force on a tissue or organ of the patient's body.

Figure 11A:
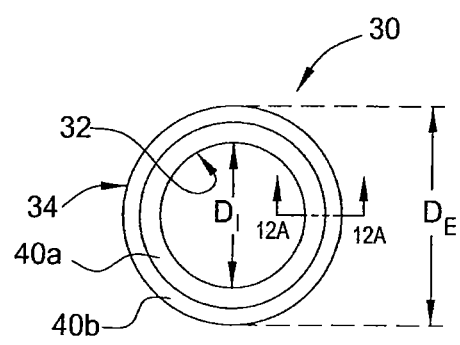
FIG. 11A is a plan view showing an unexpanded configuration of a curved portion of a device, according to an embodiment of the invention.

In the configuration of FIG. 11A, both first expandable element 40*a* and second expandable element 40*b* are unexpanded. The configuration of curved portion 30 shown in FIG. 11A may be referred to as the fully unexpanded configuration. In the configuration shown in FIG. 11A, curved portion 30 has an internal diameter $D_I$ and an external diameter $D_E$. Curved portion 30 is configured for radially outward expansion thereof independently of any radially inward expansion.

Figure 11B:
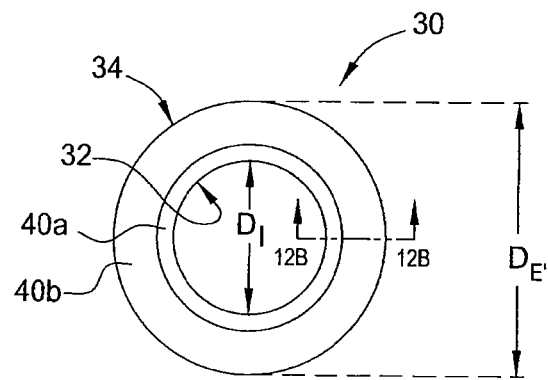
FIG. 11B shows the curved portion of FIG. 11A having an expandable element in an expanded configuration for effecting radially outward expansion of the curved portion, according to one embodiment of the invention.

FIG. 11B shows the curved portion 30 of FIG. 11A having only second expandable element 40*b* in an expanded configuration. Thus, in the configuration of FIG. 11B, first expandable element 40*a* is unexpanded. In an embodiment, the fully unexpanded configuration of FIG. 11A may be converted to the configuration of FIG. 11B by passage of a suitable inflation medium into second expandable element 40*b*, for example, as described hereinabove with respect to FIG. 9. Such passage of a suitable inflation medium into second expandable element 40*b* effects radially outward expansion of curved portion 30, whereby the external diameter of curved portion 30 increases from $D_E$ to $D_E'$. It is worthy of note, however, that according to one aspect of the invention, radially outward expansion of curved portion 30 shown in FIG. 11B may occur in the absence, or substantially in the absence, of radially inward expansion of curved portion 30. For example, following radially outward expansion of curved portion 30 via expansion of second expandable element 40*b*, in FIG. 11B, the internal diameter, $D_I$, may be at least substantially the same as that in the fully unexpanded configuration of FIG. 11A.

Figure 11C:
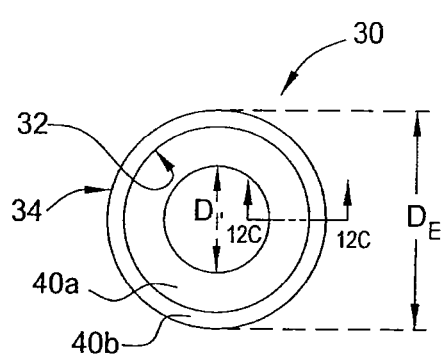
FIG. 11C schematically represents the curved portion of FIG. 11A having an expandable element in an expanded configuration for effecting radially inward expansion of the curved portion, according to one embodiment of the invention.

FIG. 11C shows the curved portion 30 of FIG. 11A having only first expandable element 40*a* in an expanded configuration; second expandable element 40*b* is unexpanded. In an embodiment, the fully unexpanded configuration of FIG. 11A may be converted to the configuration of FIG. 11C by passage of a suitable inflation medium into first expandable element 40*a*, for example as described hereinabove. Such passage of a suitable inflation medium into first expandable element 40*a* effects radially inward expansion of curved portion 30, whereby the internal diameter of curved portion 30 decreases from $D_I$ to $D_I'$. Once again, it is worthy of note that according to one aspect of the invention, radially inward expansion of curved portion 30 shown in FIG. 11C may occur in the absence, or substantially in the absence, of radially outward expansion of curved portion 30. For example, following radially inward expansion of curved portion 30 via expansion of first expandable element 40*a*, in FIG. 11C, the external diameter, $D_E$, may be at least substantially the same as that in the fully unexpanded configuration of FIG. 11A.

Figure 11D:
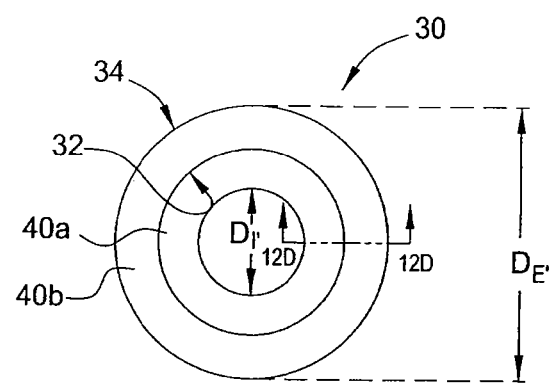
FIG. 11D schematically represents the curved portion of FIG. 11A having two expandable elements in an expanded configuration for effecting both radially inward expansion and radially outward expansion of the curved portion, according to one embodiment of the invention.
Figure 12A:
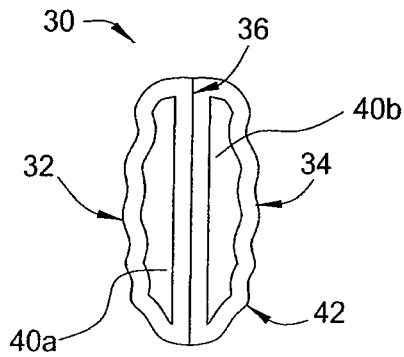
FIGS. 12A-D are sectional views taken along the lines 12A-12A, 12B-12B, 12C-12C, and 12D-12D, respectively of FIGS. 11A-D, showing expandable elements separate from a wall of the curved portion, according to one embodiment of the invention.
Figure 12B:
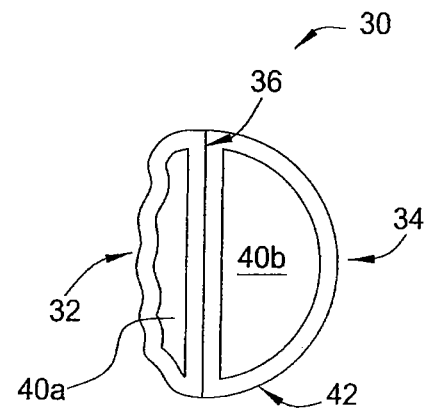
Figure 12C:
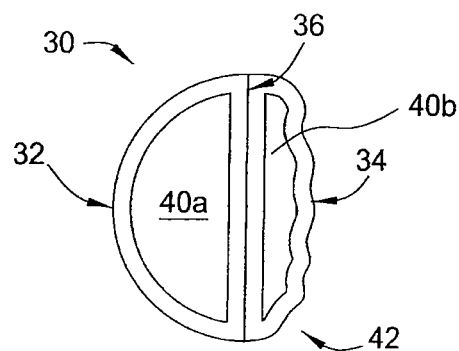
Figure 12D:
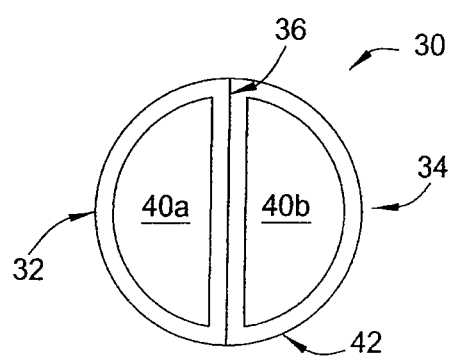

FIG. 11D shows the curved portion 30 of FIG. 11A having both first expandable element 40a and second expandable element 40b in an expanded configuration. The configuration of curved portion 30 shown in FIG. 11D may be referred to as the fully expanded configuration. In an embodiment, the fully unexpanded configuration of FIG. 11A, may be converted to the fully expanded configuration of FIG. 11D by passage of a suitable inflation medium into both first expandable element 40a and second expandable element 40b. Such passage of a suitable inflation medium into first expandable element 40a and second expandable element 40b effects radially inward expansion and radially outward expansion of curved portion 30, whereby the internal diameter of curved portion 30 decreases from $D_I$ to $D_I'$, and the external diameter of curved portion 30 increases from $D_E$ to $D_E'$.

Thus, according to an embodiment of the present invention, curved portion 30 may be expanded radially outward, while curved portion 30 is implanted in a patient's body, independently of any radially inward expansion of curved portion 30. Furthermore, according to another embodiment of the present invention, curved portion 30 may be expanded radially inward, while curved portion 30 is implanted in a patient's body, independently of any radially outward expansion of curved portion 30. Still further, curved portion 30 may be expanded radially outward and radially inward, independently of each other and to varying extents. In an embodiment, curved portion 30 may be configured for concurrent expansion or contraction of first expandable element 40a and second expandable element 40b.

When curved portion 30 is suitably disposed or implanted within a patient, radially inward expansion and/or radially outward expansion of curved portion 30 may exert a mechanical force against at least one tissue or organ of the patient's body. As an example, radially outward expansion and/or radially inward expansion of curved portion 30 may exert a mechanical force on nerve tissue sufficient to mechanically neuromodulate the nerve tissue. As a further, example, radially inward expansion of curved portion 30 may exert a mechanical force on the esophagus sufficient to constrict the lumen of the esophagus. By varying the extent of radial outward expansion or radial inward expansion of curved portion 30, the magnitude of the mechanical force exerted on a tissue or organ can be adjusted or controlled.

FIGS. 12A-D are sectional views taken along the lines 12A-12A, 12B-12B, 12C-12C, and 12D-12D, respectively of FIGS. 11A-D, according to an embodiment of the invention. FIGS. 12A-D show a barrier 36 disposed between first and second expandable elements 40a, 40b within curved portion 30. In the embodiment of FIGS. 12A-D, first and second expandable elements 40a, 40b are separate from a wall 42 of curved portion 30. Wall 42 may completely enclose curved portion 30. Wall 42 may comprise an extensible material that may readily distend, e.g., radially inwards at radially inner surface 32 or radially outwards at radially outer surface 34. For example, each of radially inner surface 32 and radially outer surface 34 may be extensible, such that radially inner surface 32 may be extended radially inward when first expandable element 40a is expanded, and radially outer surface 34 may be extended radially outward when second expandable element 40b is expanded.

Again with reference to FIGS. 12A-D, second expandable element 40b may be expanded or contracted independently of any expansion or contraction of first expandable element 40a. Barrier 36 may be at least substantially non-extensible when one or both of first expandable element 40a and second expandable element 40b are expanded. For example, barrier 36 may allow curved portion 30 to be expanded radially outward via expansion of second expandable element 40b independently of any radially inward expansion of curved portion 30. Similarly, barrier 36 may allow curved portion 30 to be expanded radially inward via expansion of first expandable element 40a independently of any radially outward expansion of curved portion 30. As a non-limiting example, barrier 36 may comprise a resilient layer of a material which may be woven in the form of a fabric, and the like.

FIGS. 13A-D are sectional views of curved portion 30, taken along the lines 12A-12A, 12B-12B, 12C-12C, and 12D-12D, respectively of FIGS. 11A-D, according to another embodiment of the invention. The embodiment of curved portion 30 shown in FIGS. 13A-D includes an outer wall 42 and a barrier 36, the latter disposed between first and second expandable elements 40a, 40b. In the embodiment of FIGS. 13A-D, first and second expandable elements 40a, 40b are integral with wall 42. Wall 42, first and second expandable elements 40a, 40b, and barrier 36 may otherwise possess characteristics and features essentially as described hereinabove, e.g., with reference to FIGS. 12A-D.

FIGS. 14A and 14C are plan views of a curved portion 30 of a device for treating a patient in unexpanded and expanded configurations, respectively, according to another embodiment of the invention. FIG. 14B is a sectional view of the unexpanded configuration of curved portion 30, taken along the lines 14B-14B of FIG. 14A, showing a bore within curved portion 30. FIG. 14D is a sectional view of the expanded configuration of curved portion 30, taken along the lines 14D-14D of FIG. 14C. With further reference to FIGS. 14A-D, curved portion 30 includes an internal barrier 36 disposed between first and second expandable elements 40a, 40b. The embodiment of curved portion 30 shown in FIGS. 14A-D, including barrier 36, first expandable element 40a, and second expandable element 40b, may include features and characteristics as described herein for other embodiments of the invention, e.g., as described with reference to FIGS. 12A-D.

In the embodiment of FIGS. 14A-D, curved portion 30 may be cannulated to further include a bore 38. Bore 38 may be configured for receiving, and for passage therethrough, of a guidewire 120 or other filament 120', neither of which are shown in FIGS. 14A-D (see, e.g., FIGS. 7A, 19A-D). Bore 38 may be located substantially centrally within curved portion. In an embodiment, bore 38 may be integral with barrier 36.

Figure 15:
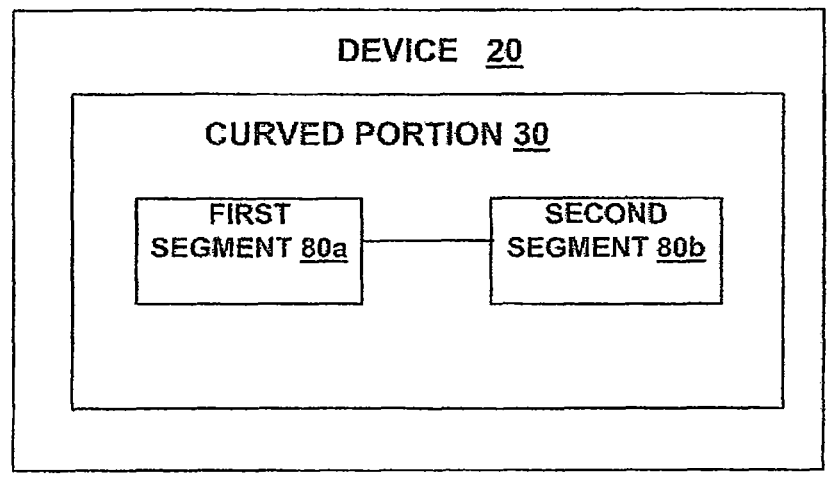
FIG. 15 is a block diagram schematically representing a device having a segmented curved portion, according to another embodiment of the invention.

FIG. 15 is a block diagram schematically representing a device 20 for treating a patient, according to another embodiment of the invention. In the embodiment of FIG. 15, device 20 includes a curved portion 30 having a plurality of segments represented as a first segment 80a and an $n^{th}$ segment 80n. Segments 80a, 80n may be coupled together to form curved portion 30, wherein curved portion 30 may be configured for at least partially encircling the esophagus of the patient. At least one of segments 80a, 80n may be arcuate, U-shaped, C-shaped, or semi-circular. Each of segments 80a, 80n may include one or more expandable elements 40a-n (see, e.g., FIGS. 8-14D and FIG. 17). In an embodiment, each of segments 80a, 80n may include a first expandable element 40a and a second expandable element 40b, and curved portion 30 may be configured for radially outward expansion independently of any radially inward expansion of curved portion 30 (see, e.g., FIGS. 11A-D).

Figure 16B:
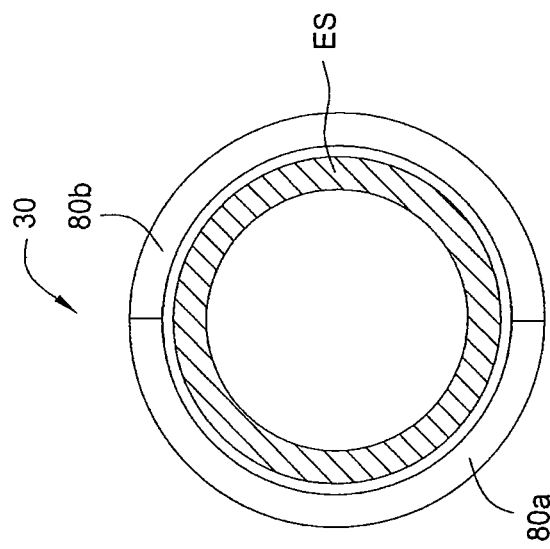
FIG. 16B schematically represents the arcuate segments of FIG. 16A coupled to form an annular curved portion.
Figure 16A:
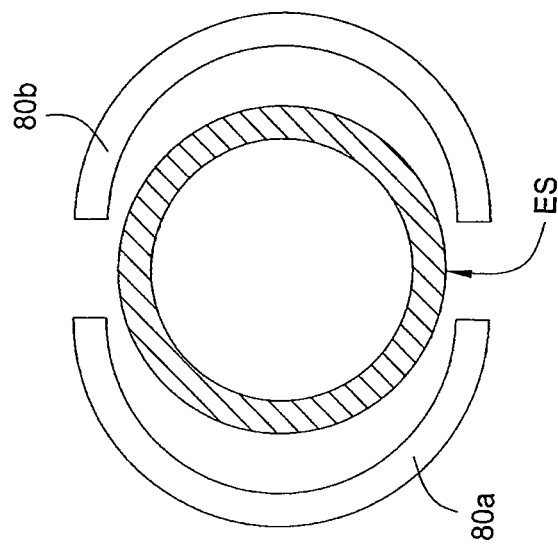
FIG. 16A schematically represents arcuate segments of a curved portion in relation to the esophagus of a patient, according to an embodiment of the invention.

FIG. 16A schematically represents a first arcuate segment 80a and a second arcuate segment 80b in relation to the esophagus, ES, of a patient, according to another embodiment of the invention. FIG. 16B shows first and second arcuate segments 80a, 80b which may be coupled together to form curved portion 30, wherein curved portion 30 may be at least substantially annular and wherein curved portion 30 at least partially encircles the esophagus. Each of first and second arcuate segments 80a, 80b may include a first expandable element 40a and a second expandable element 40b (see, e.g., FIG. 17), and curved portion 30 may be configured for radially outward expansion independently of any radially inward expansion of curved portion 30, essentially as described hereinabove. Although, FIG. 16A shows two arcuate segments 80a, 80b, other numbers of segments are also within the scope of the invention.

Figure 17:
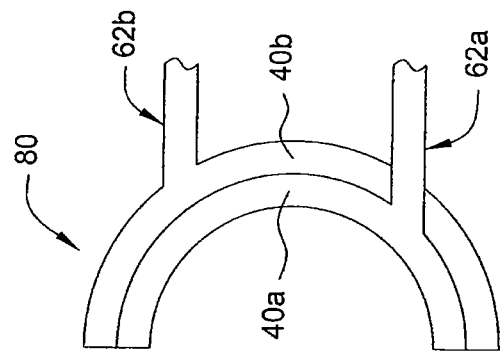
FIG. 17 schematically represents a segment of a curved portion having first and second expandable elements, according to an embodiment of the invention.

FIG. 17 schematically represents one arcuate segment 80 of a curved portion 30, according to an embodiment of the invention. Arcuate segment 80 includes first and second expandable elements 40a, 40b, respectively. First expandable element 40a may be in communication with a source of an inflation medium 61 (see, e.g., FIG. 8) via a first conduit 62a. Second expandable element 40b may be in communication with a source of inflation medium 61 via a second conduit 62b. Accordingly, segment 80 may be expanded radially outward or radially inward independently of any radially inward or radially outward expansion of segment 80 to provide for independent radially outward and radially inward expansion of curved portion 30.

Figure 18:
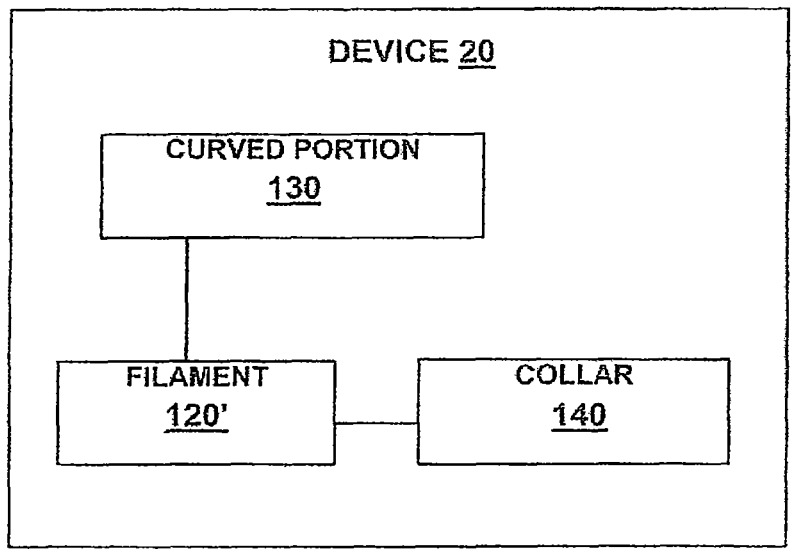
FIG. 18 is a block diagram schematically representing a device having a curved portion and a filament, according to another embodiment of the invention.

FIG. 18 is a block diagram schematically representing a device 20 for treating a patient, according to another embodiment of the invention. In the embodiment of FIG. 18, device 20 includes a curved portion 130, a filament 120', and a collar 140. In an embodiment, filament 120' may comprise a guidewire or the like. Curved portion 130 may be cannulated for passage of filament 120' therethrough and for adjusting a diameter of curved portion 130 for the effective treatment of the patient. Collar 140 may be configured for slidably receiving filament 120' and for locking filament 120' with respect to collar 140 and/or for locking filament 120' with respect to curved portion 130 (see, e.g., FIGS. 19A-D and 19F-G).

Figure 19A:
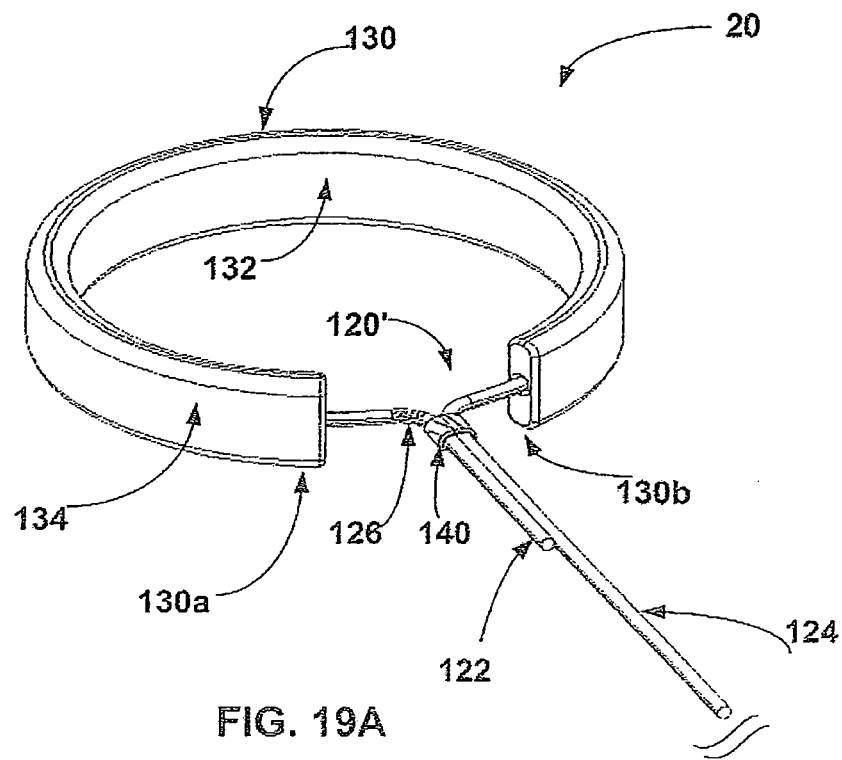
FIG. 19A is a perspective view of a device schematically representing an unexpanded or contracted configuration of a curved portion of the device in relation to a filament, according to another embodiment of the invention.
Figure 19B:
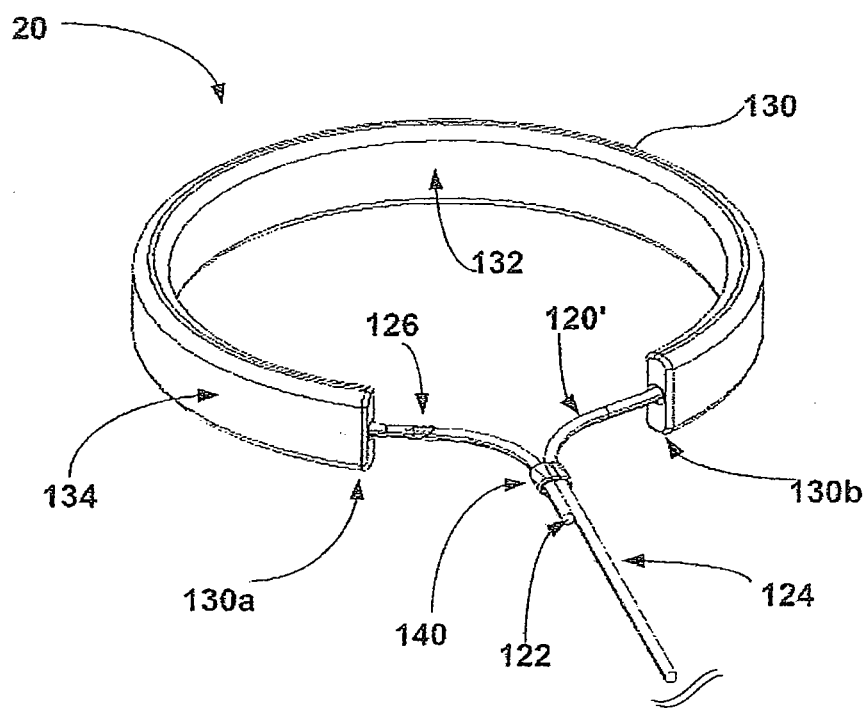
FIG. 19B is a perspective view of the device of FIG. 19A schematically representing an expanded configuration of the curved portion in relation to the filament, according to an aspect of the invention.

FIGS. 19A-B show a cannulated device 20, according to another embodiment of the invention. Device 20 includes a curved portion 130, a filament 120' and a collar 140. FIG. 19A shows an unexpanded or contracted configuration of curved portion 130 in relation to filament 120'. FIG. 19B shows an expanded configuration of curved portion 130 in relation to filament 120'. Device 20 is configured for adjustably transforming curved portion 130 between the unexpanded and expanded configurations. Curved portion 130 includes a first end 130a, a second end 130b, a radially inner surface 132, and a radially outer surface 134. Curved portion 130 may be cannulated to further include a bore 150 therethrough (see, e.g., FIG. 19E). Bore 150 may be configured for passage therethrough of filament 120'. Curved portion 130 may be adjustably transformed between the unexpanded and expanded configurations by the controlled passage of filament 120' through bore 150.

Figure 19C:
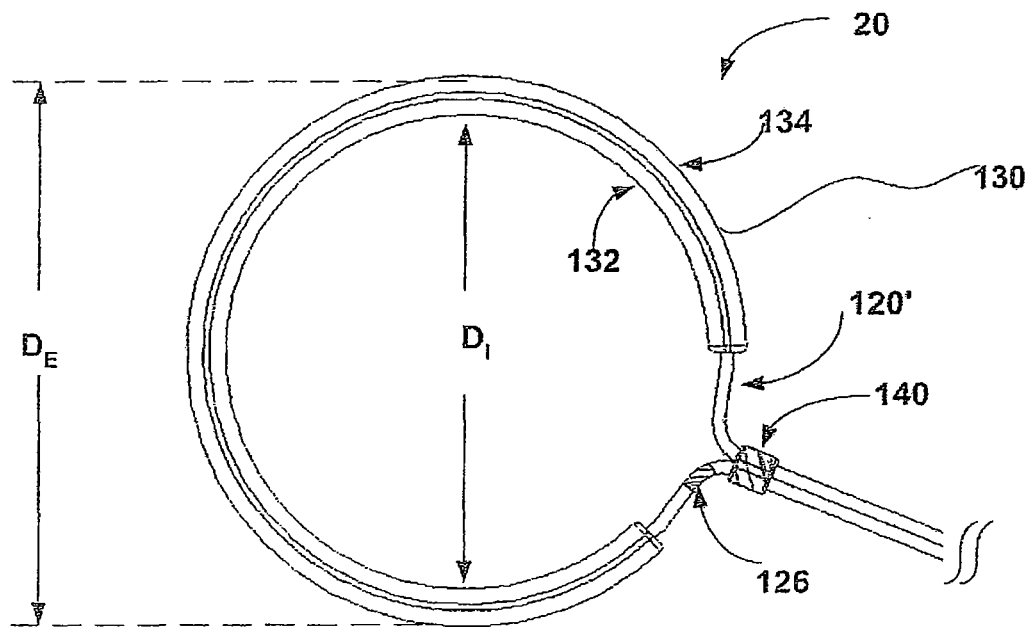
FIGS. 19C-D are plan views showing the unexpanded and expanded configurations of the curved portion of FIGS. 19A-B, respectively, in relation to the filament.
Figure 19D:
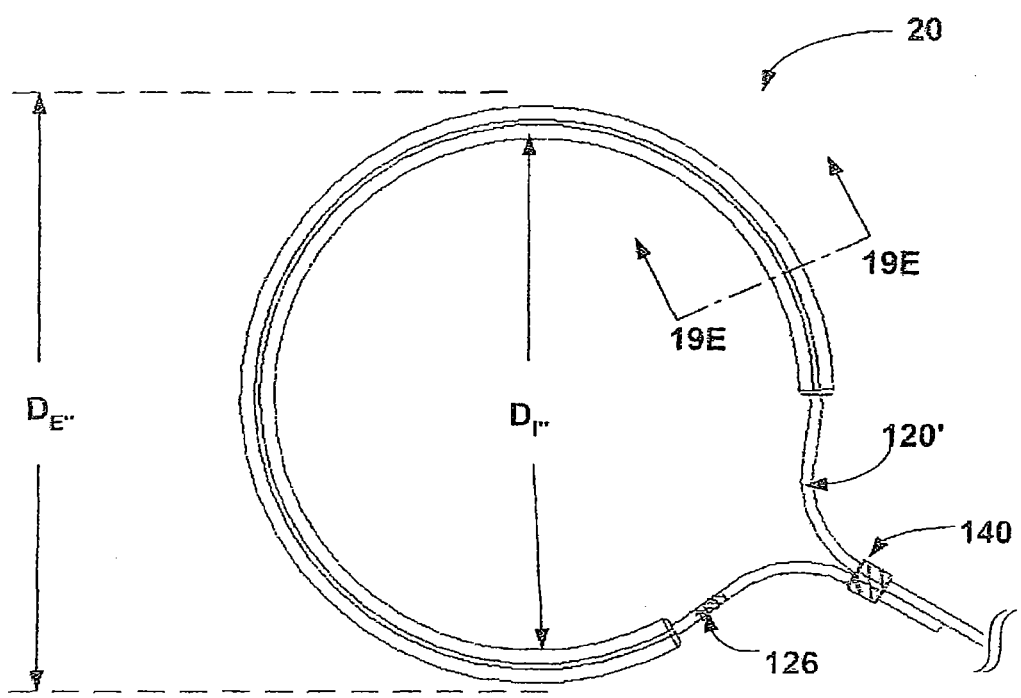

FIGS. 19C-D are plan views showing the unexpanded and expanded configurations of the curved portion 130 of FIGS. 19A-B, respectively, in relation to filament 120'. Collar 140 is in communication with curved portion 130 via filament 120'. Filament 120' extends distally from collar 140 to second end 130b of curved portion 130, through bore 150 to first end 130a of curved portion 130, and proximally from first end 130a of curved portion 130 to collar 140. Filament 120' may further extend from first end 130a proximally through and beyond collar 140.

Figure 19F:
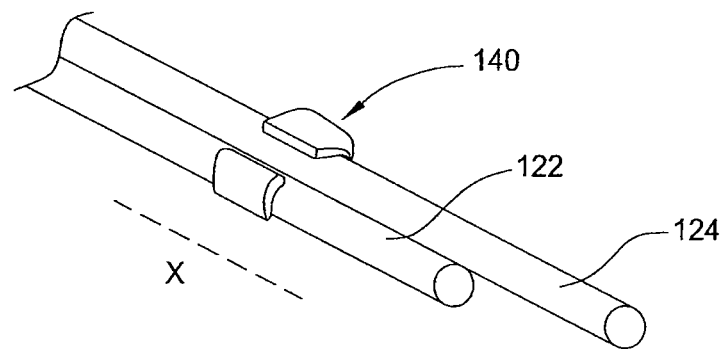
FIGS. 19F-G are perspective views schematically representing an unlocked configuration and a locked configuration, respectively, of a collar in relation to the filament, according to another embodiment of the invention.
Figure 19G:
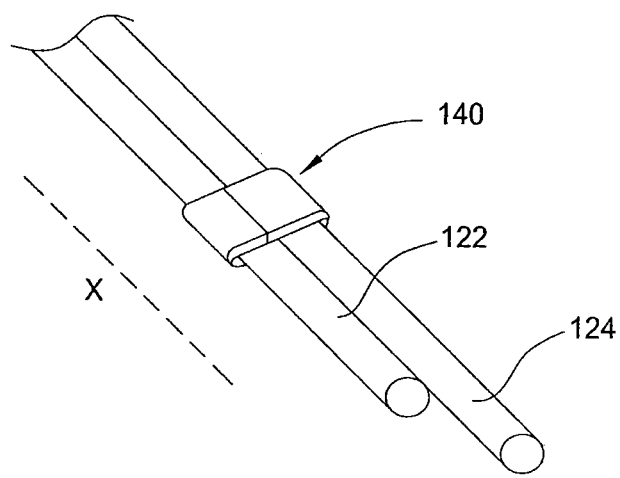
Figure 19E:
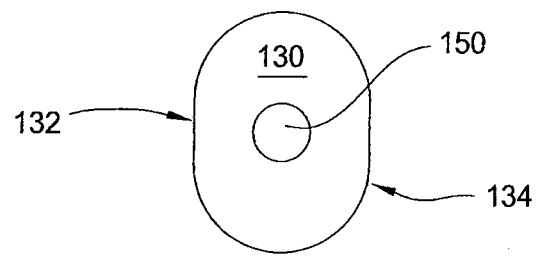
FIG. 19E is a sectional view taken along the lines 19E-19E of FIG. 19D.

FIG. 19E is a sectional view taken along the lines 19E-19E of FIG. 19D, showing curved portion 130 including radially inner surface 132, radially outer surface 134, and bore 150. In use, filament 120' may be disposed within bore 150. Filament 120' is omitted from FIG. 19E for the sake of clarity.

FIGS. 19F-G are perspective views schematically representing an unlocked configuration and a locked configuration, respectively, of collar 140 in relation to filament 120', according to another embodiment of the invention. With reference to FIGS. 19A-G, collar 140 is configured for slidably accommodating a first strand 122 and a second strand 124 of filament 120'. Device 20 is configured for adjusting an internal diameter ($D_{I'}$ $D_{I'}$) and an external diameter ($D_E/D_E''$) of curved portion 130 by passage of at least one of first strand 122 and second strand 124 within collar 140. For example, by passage of at least one of first strand 122 and second strand 124 within collar 140, curved portion 130 may be adjusted from a first internal diameter $D_I$ and a first external diameter $D_E$ to a second internal diameter $D_I''$ and a second external diameter $D_E''$.

In an embodiment, the external and internal diameter of curved portion 130 can be controlled by axial movement of filament 120' with respect to collar 140. Alternatively, the external and internal diameter of curved portion 130 can be controlled by axial movement of collar 140 with respect to filament 120'. The longitudinal axis of collar 140 is represented in FIGS. 19F-G by the broken line labeled, X. Collar 140 is adapted for locking filament 120' with respect to collar 140 such that axial movement of collar 140 with respect to filament 120' is prevented when collar 140 is in the locked configuration (FIG. 19G). In an embodiment, collar 140 is adapted for reversibly locking and unlocking filament 120'.

Figure 19H:
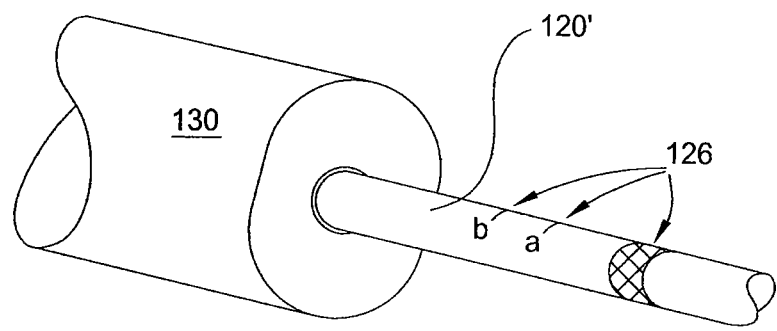
FIG. 19H is an enlarged view of the filament showing markings on the filament extending from the curved portion, according to another embodiment of the invention.

FIG. 19H is an enlarged view of filament 120' extending from curved portion 130, according to another embodiment of the invention. In the embodiment of FIG. 19H, filament 120' includes at least one marking 126. One or more of markings 126 may be configured to allow the surgeon to visualize, e.g., during a surgical procedure, a relative location of filament 120' with respect to at least one of curved portion 130 and collar 140. Markings 126 may comprise at least one gradation, e.g., in the form of a line arranged perpendicular to the axis of filament 120', and/or in the form of at least one alphanumeric character, e.g., "a", "b", "1" (the latter character is not shown in FIG. 19H). In another embodiment, one or more of the markings 126 may be in the form of a region of shading or at least one color, which may be suitably arranged and indicated at various locations on filament 120' for visualizing a relative location of filament 120' with respect to other elements.

Figure 20:
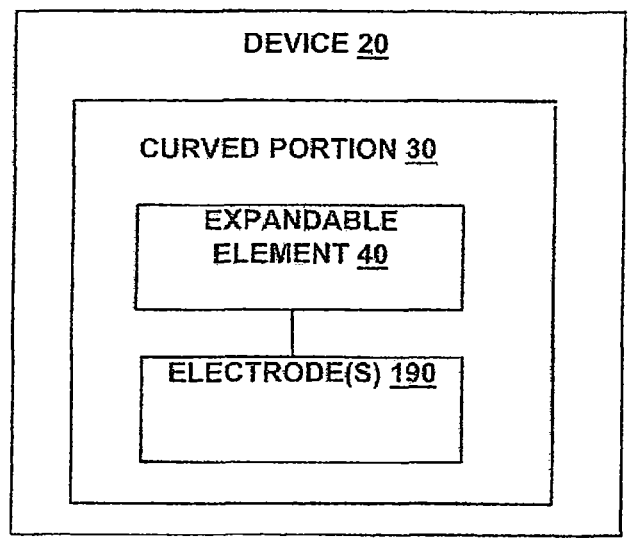
FIG. 20 is a block diagram schematically representing a device having a curved portion, an expandable element, and an electrode, according to another embodiment of the invention.

FIG. 20 is a block diagram schematically representing a device 20 for treating a patient, according to another embodiment of the invention. In the embodiment of FIG. 20, device 20 includes a curved portion 30, an expandable element 40, and an electrode 190. Curved portion 30 may be configured for expansion in at least one dimension. For example, curved portion 30 may be configured for radially outward expansion independently of any radially inward expansion of curved portion 30. Alternatively, or additionally, curved portion 30 may be configured for radially inward expansion independently of any radially outward expansion of curved portion 30. In an embodiment, curved portion 30 may be configured for concurrently, yet independently, expanding curved portion 30 radially inward and radially outward. Electrode 190 may be disposed on an external surface of curved portion 30.

Figure 21:
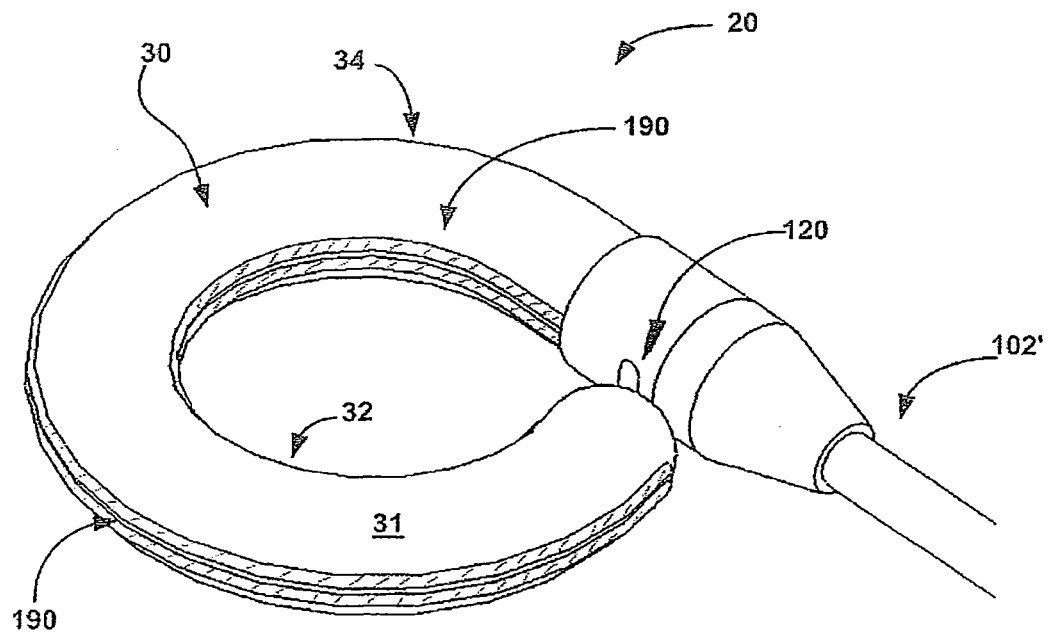
FIG. 21 is a perspective view of a device having an electrode on a curved portion of a device, according to another embodiment of the invention.

FIG. 21 is a perspective view of a device 20 for treating a patient, according to another embodiment of the invention. In the embodiment of FIG. 21, device 20 includes a curved portion 30, having an external surface 31, and a plurality of electrodes 190. Curved portion 30 may include one or more electrodes 190 disposed on both a radially inner surface 32 and a radially outer surface 34. Device 20 may further include a working channel 102' and a guidewire 120. In an embodiment, guidewire 120 may be adapted for stabilizing device 20 in the arcuate or curved configuration. In another embodiment, guidewire 120 may be configured for coupling distal and proximal ends of device 20 (see, for example, FIG. 3 and FIGS. 4A-B). Working channel 102' may be detached from curved portion 30, for example, after suitable placement or implantation of curved portion 30 within the patient's body. In an embodiment, curved portion 30 may be placed at the distal esophagus. According to one aspect of the invention, curved portion 30 may be placed sub-fascially, i.e., beneath a fascia of the patient, and curved portion 30 may be disposed in at least close proximity to the diaphragm and extraluminally with respect to the esophagus.

Curved portion 30 may be configured for adopting an expanded configuration or an unexpanded configuration. In the expanded configuration, electrode(s) 190 may protrude from external surface 31, wherein upon expansion of curved portion 30, external surface 31 increases in area and becomes taut. In the expanded configuration of curved portion 30, protrusion of electrode(s) 190 from external surface 31 may promote and/or enhance electrical contact between electrode (s) 190 and a targeted tissue of the patient. As an example only, expansion of curved portion 30 may promote electrical contact between electrodes 190 and a targeted nerve tissue of the patient (see, e.g., FIGS. 22A-B, 23A-C).

Although, the configuration of FIG. 21 shows two elongated electrodes disposed on each of a radially inner and a radially outer surface of curved portion 30, it is to be understood that the configuration shown is exemplary only, and other numbers and arrangements of electrodes are contemplated under the instant invention.

Figure 22A:
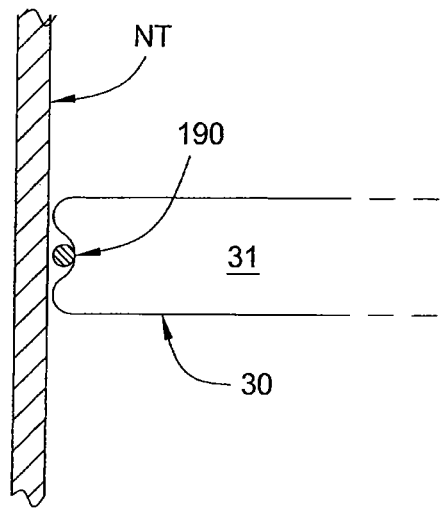
FIG. 22A schematically represents an unexpanded configuration of a curved portion showing little or no electrical contact between an electrode and nerve tissue, according to another embodiment of the invention.

FIG. 22A schematically represents an unexpanded configuration of a curved portion 30 in relation to nerve tissue, NT, according to another embodiment of the invention. Curved portion 30 includes at least one electrode 190. Electrode 190 may be disposed on an external surface 31 of curved portion 30. Curved portion 30 of FIGS. 22A-B may have various additional features and characteristics, e.g., as described with respect to FIGS. 20-21.

In the unexpanded configuration of FIG. 22A, electrode 190 makes little or no electrical contact with nerve tissue, NT. In contrast, by expansion of curved portion 30, electrode 190 is urged into electrical contact with the nerve tissue. Accordingly, the expanded configuration of curved portion 30, schematically represented at FIG. 22B, ensures electrical contact between electrode 190 and the nerve tissue. Transformation of the unexpanded configuration of curved portion 30 (FIG. 22A) to the expanded configuration (FIG. 22B) may be accomplished, for example, via radially outward or radially inward expansion of curved portion 30. As an example, such expansion may result from inflation of at least one expandable element of device 20 (see, e.g., FIG. 20). Radially outward expansion of curved portion 30 may occur independently of, or in the absence of, radially inward expansion of curved portion 30 (see, for example, FIGS. 11A-D, 12A-D). Electrical contact between electrode 190 and the nerve tissue allows one or more electrical signals to be applied to the nerve tissue, wherein the electrical signals are sufficient to electrically neuromodulate the nerve tissue. Parameters for such electrical signals, including voltage, pulse frequency, and the like, that are generally suitable for electrical modulation of nerve tissue in human patients are known in the art.

Again with reference to FIGS. 22A-B, the nerve tissue, NT, may comprise a nerve tissue targeted by a physician for treatment of the patient. As an example only, and not to limit the invention in any way, the nerve tissue may comprise a nerve tissue that innervates the stomach of the patient. In another non-limiting example, the nerve tissue may comprise a nerve tissue that innervates the diaphragm of the patient.

Figure 22B:
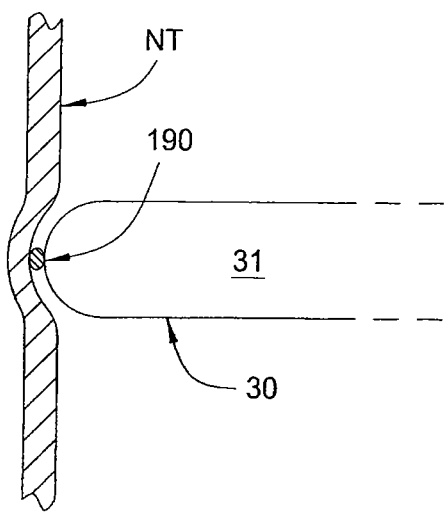
FIG. 22B schematically represents an expanded configuration of the curved portion of FIG. 22A, showing electrical contact between the electrode and the nerve tissue, according to another embodiment of the invention.
Figure 23B:
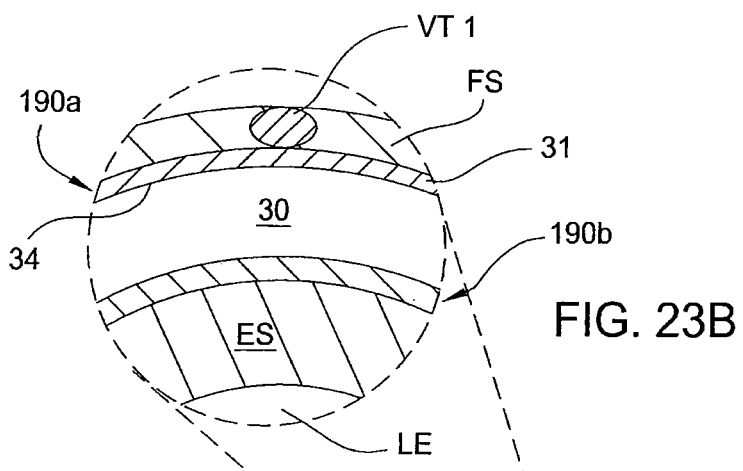
FIG. 23B is an enlarged portion of FIG. 23A showing the curved portion internal to the first vagal trunk.
Figure 23A:
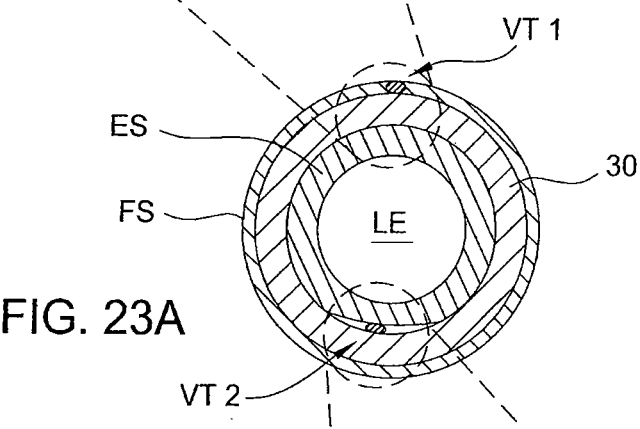
FIG. 23A is a horizontal sectional view showing a curved portion of a device disposed sub-fascially and extraluminally with respect to the esophagus, according to another embodiment of the invention.
Figure 23C:
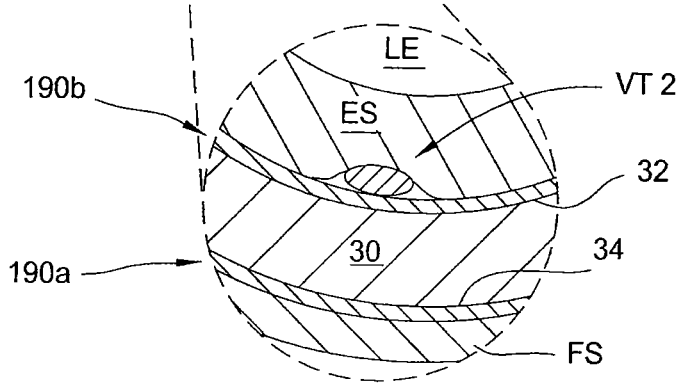
FIG. 23C is an enlarged portion of FIG. 23A showing the curved portion external to the second vagal trunk.

Although FIGS. 22A-B show electrical contact between an electrode 190 and the nerve tissue via radially outward expansion of curved portion 30, in other embodiments of the present invention electrical contact between an electrode 190 and the nerve tissue may similarly be achieved by radially inward expansion of curved portion having at least one electrode 190 mounted on a radially inner surface of curved portion 30 (see, for example, FIGS. 21, 23A, 23C).

FIG. 23A is a horizontal sectional view showing a curved portion 30 of a device disposed with respect to the esophagus, ES, according to another embodiment of the invention. Curved portion 30 may be disposed sub-fascially, i.e., embedded beneath the fascia, FS, as shown in FIG. 23A. As an example, the fascia may comprise the diaphragmatic fascia or a portion of the fascia surrounding the esophagus. As shown, curved portion 30 may also be disposed extraluminally, i.e., external to the lumen, LE, of the esophagus. Curved portion 30 may include an outer electrode 190a disposed on radially outer surface 34, and an inner electrode 190b disposed on radially inner surface 32. Curved portion 30 shown in FIGS. 23A-C may have various additional features and characteristics as described herein for other embodiments of the present invention, e.g., with respect to FIGS. 20-21.

In FIGS. 23A-C, curved portion 30 may be in an expanded configuration. The expanded configuration of curved portion 30 may provide reliable and enhanced electrical contact between at least one of outer and inner electrodes 190a, 190b and nerve tissue. Curved portion 30 may undergo radially outward and/or radially inward expansion. As observed for other embodiments of the present invention, such radially outward and radially inward expansion may occur independently of each other (see, e.g., FIGS. 11A-D).

In the embodiment of FIGS. 23A-C, targeted nerve tissue is represented as a first vagal trunk, VT1, and a second vagal trunk, VT2. FIG. 23A shows curved portion 30 internal to the first vagal trunk and external to the second vagal trunk. This representation is merely exemplary, and is not to be construed as limiting the invention in any way. In other embodiments, curved portion 30 may alternatively be disposed internal to both the first vagal trunk and the second vagal trunk, external to both the first vagal trunk and the second vagal trunk, or external to the first vagal trunk and internal to the second vagal trunk. Each of the first vagal trunk and the second vagal trunk may comprise anterior vagal trunk or the posterior vagal trunk of the patient.

FIG. 23B is an enlarged portion of FIG. 23A showing curved portion 30 disposed internal to the first vagal trunk, VT1, i.e., the first vagal trunk is external to outer electrode 190a. Radially outward expansion of curved portion 30 ensures reliable electrical contact is made between outer electrode 190a and the first vagal trunk.

FIG. 23C is an enlarged portion of FIG. 23A showing the curved portion 30 external to the second vagal trunk, VT2, i.e., the second vagal trunk is disposed internal to inner electrode 190b. Radially outward expansion of curved portion 30 ensures reliable electrical contact is made between inner electrode 190b and the second vagal trunk.

According to one aspect of the invention, curved portion 30 may be used for the reliable electrical neuromodulation of targeted nerve tissue. As shown in FIGS. 23A-C, curved portion 30 may be used for electrical neuromodulation of the anterior and/or posterior vagal trunk. In an embodiment, curved portion 30 may be used for electrically blocking the transmission of at least some neural impulses of the anterior and/or posterior vagal trunk. As a non-limiting example, such neural blocking effects a decrease in gastric motility, a decease in gastric enzyme secretion, and/or a decrease in gastric acid secretion. Such decrease in gastric motility, gastric enzyme production, and gastric acid production inhibits or slows digestion and delays stomach emptying in an obesity patient. Accordingly, an embodiment of the invention may be used for the effective treatment of obesity.

Furthermore, decrease in gastric motility, gastric enzyme production, and gastric acid production, as described in relation to the present invention hereinabove, also inhibits or prevents reflux of stomach contents into the esophagus of a GERD patient. For example, a less dynamic and less full stomach results in less reflux of stomach contents into the esophagus. Accordingly, the invention may be used for effectively treating GERD patients.

Although first and second vagal trunks are shown in FIGS. 23A-C, it is to be understood that the invention is not limited to neuromodulation or other treatment or targeting of vagal trunks; rather, the invention may be used for targeting, neuromodulation or other treatment of nerve tissue other than the anterior and posterior vagal trunks, including sympathetic or parasympathetic nerves, nerve plexuses, and nerve tissue, as well as sensory nerve tissue and motor nerve tissue, wherein the nerve tissue targeted, treated, or neuromodulated may innervate tissues and/or organs other than the stomach and the GI tract.

Figure 24A:
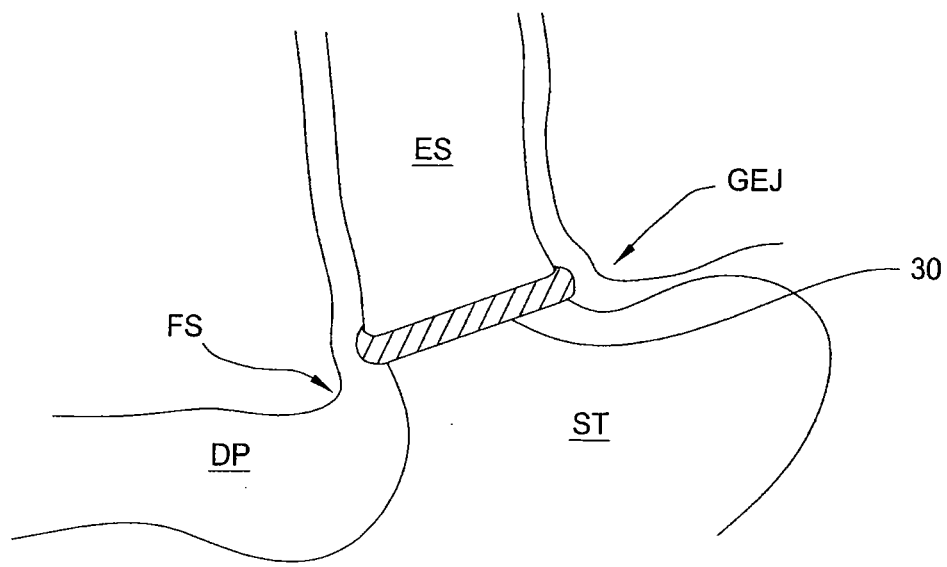
FIG. 24A schematically represents a curved portion of a device at least partially encircling the esophagus and disposed in at least close proximity to the gastro-esophageal junction, according to another embodiment of the invention.

FIG. 24A schematically represents a curved portion 30 of a device at least partially encircling the esophagus, ES, and disposed in at least close proximity to the gastro-esophageal junction, GEJ, according to an embodiment of the present invention. Curved portion 30 may be U-shaped, C-shaped, O-shaped, or at least substantially annular. Curved portion 30 may at least partially encircle the esophagus. According to one aspect of the invention, curved portion 30 may be disposed beneath a fascia, FS of the patient.

In an embodiment, curved portion 30 may be disposed at or near the diaphragm, DP, of the patient. As shown, curved portion 30 may be disposed slightly above, or somewhat superior to, the diaphragm of the patient. Although curved portion 30 is shown in FIG. 24A as disposed superior to the diaphragm, according to other embodiments of the invention, curved portion 30 may alternatively be disposed somewhat inferior to the diaphragm. According to an aspect of the present invention, curved portion 30 may be retained in situ around the distal esophagus, ES, by the fascia, FS.

Curved portion 30 as shown in FIG. 24A may be expandable in at least one dimension, e.g., radially outward and/or radially inward, and curved portion 30 may be configured for exerting a mechanical force on at least one tissue or organ of a patient. As a non-limiting example, curved portion 30 may exert a mechanical force, e.g., via radially inward or radially outward expansion, on the esophagus, ES, or on a nerve tissue that innervates the stomach or diaphragm (see, e.g., FIGS. 28, 29). Curved portion 30 may additionally include and/or possess various elements, features, and characteristics as described herein with reference to other embodiments of the invention. According to an aspect of the present invention, the device may be implanted such that no part of the device, including an expanded configuration of curved portion 30, contacts the stomach, ST, of the patient.

Figure 24B:
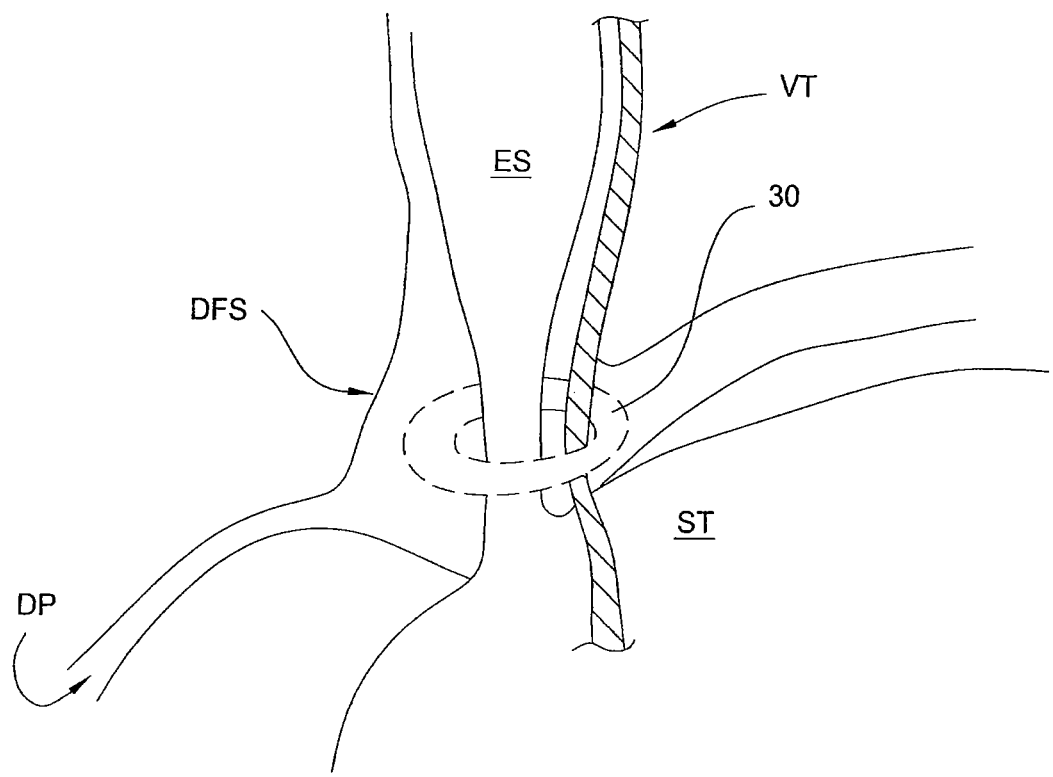
FIG. 24B is a schematic representation showing a curved portion of a device disposed sub-fascially at the distal esophagus with a vagal trunk disposed internally within the curved portion, according to another embodiment of the invention.

FIG. 24B is a schematic representation showing a curved portion 30 of a device for treating a patient, according to another embodiment of the invention. Curved portion 30 may be at least substantially annular. According to an embodiment of the invention depicted in FIG. 24B, curved portion 30 may be disposed sub-fascially at the distal end of the esophagus, ES, such that a vagal trunk, VT may be disposed internally within curved portion 30. In other embodiments, the vagal trunk may be disposed externally with respect to curved portion 30. In yet other embodiments, both the anterior and posterior vagal trunks (not shown in FIG. 24B) may be disposed internally or externally with respect to curved portion 30.

Curved portion 30 as shown in FIG. 24B may be expandable in at least one dimension, e.g., for exerting a mechanical force on at least one tissue or organ of a patient. As a non-limiting example, curved portion 30 may exert a mechanical force on vagal trunk, VT, sufficient to at least partially block the transmission of neural impulses within the vagal trunk. Such neural blocking may effect a decrease in at least one of: gastric motility, gastric enzyme secretion, and gastric acid secretion, for example, substantially as described hereinabove (e.g., with reference to FIGS. 23A-C). Accordingly, the embodiment of FIG. 24B may be used for effectively treating obesity patients. Curved portion 30 of FIG. 24B may include or possess various elements, features, and characteristics as described herein with reference to other embodiments of the invention.

Figure 25:
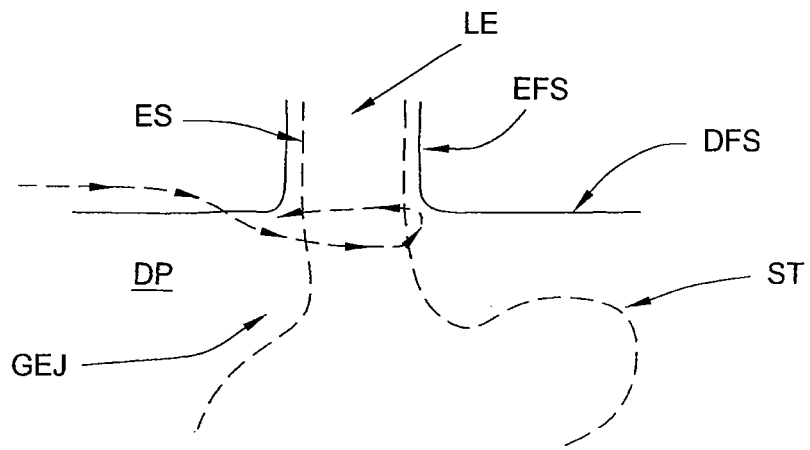
FIG. 25 schematically represents a path for advancing a device to a sub-fascial location in at least close proximity to the gastro-esophageal junction for placement of a curved portion of the device extraluminally with respect to the esophagus, according to one aspect of the invention.

FIG. 25 schematically represents a path for advancing an apparatus for treating a patient to a sub-fascial location in at least close proximity to the gastro-esophageal junction, according to one aspect of the invention. The path of advancement is represented by the arrowed line in FIG. 25 and is shown in relation to the esophagus, ES, the stomach, ST, the diaphragm, DP, the gastro-esophageal junction, GEJ, the esophageal fascia, EFS, and the diaphragmatic fascia, DFS. The esophageal fascia may be considered to be an extension of the diaphragmatic fascia or a part of the parietal fascia. The apparatus is omitted from FIG. 25 for the sake of clarity. Such apparatus may comprise a device 20 including a curved portion 30, as well as other elements and features as described with reference to various embodiments of the invention (see, e.g., FIGS. 1-24B).

With further reference to FIG. 25, as shown by the arrowed line, the path of advancement of a device 20 (not shown in FIG. 25) may extend through the thorax, i.e., superior to the diaphragm, to a location in at least close proximity to the esophageal foramen/distal esophagus, thence beneath the diaphragmatic fascia, DFS, and around the distal esophagus such that device 20 at least partially encircles the esophagus, ES. According to one aspect of the instant invention, device 20 may be advanced sub-fascially along a path of least resistance between the fascia and muscular layers of the esophagus such that device 20 at least partially encircles the esophagus. According to another aspect of the instant invention, after sub-fascial placement of device 20 extraluminally at the distal esophagus, device 20 may be retained in situ around the esophagus via the fascia (diaphragmatic or esophageal fascia).

Sub-fascial placement of a device according to an embodiment of the instant invention is further described with reference to FIG. 41. It is to be understood, however, that various paths and procedures other than those described with reference to FIGS. 25 and 41 may also be used within the scope of the instant invention. Device 20 may be placed at the gastro-esophageal junction, the esophageal-diaphragmatic junction, or the gastro-diaphragmatic junction.

Figure 26:
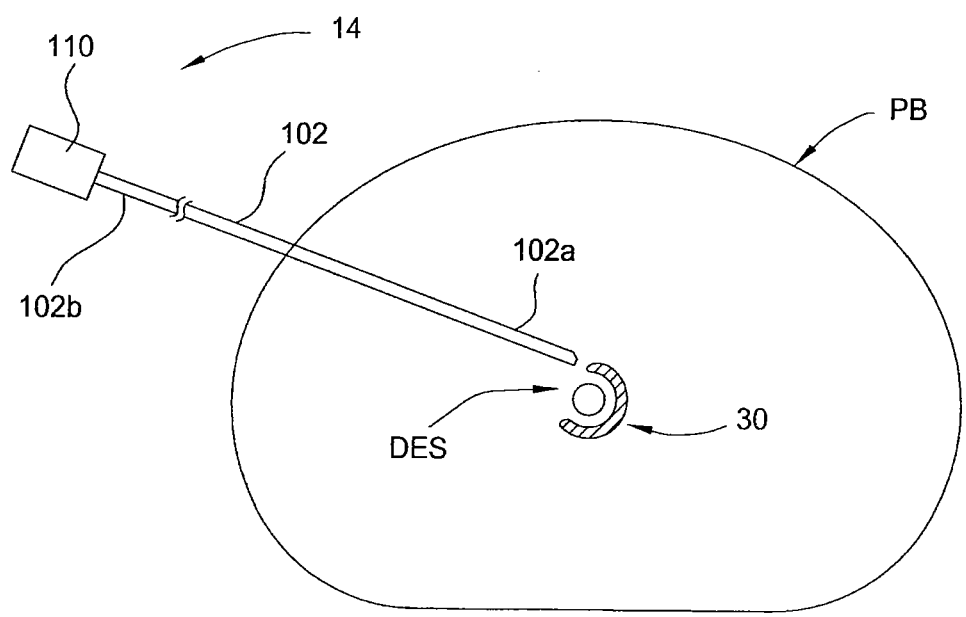
FIG. 26 schematically represents lateral placement of a curved portion of a device at the distal esophagus of a patient, according to another embodiment of the invention.

FIG. 26 schematically represents lateral placement of a curved portion 30 of a device in a patient, according to another embodiment of the invention. With reference to FIG. 26, curved portion 30 may be implanted within the patient's body, PB, via an introducer element 14 (see, e.g., FIGS. 7A-C). Introducer element 14 includes a shaft 102 which may be coupled to a handpiece 110. Handpiece 110 may be used for manipulating introducer element 14 and/or curved portion 30. A distal end 102a of shaft 102 may be introduced via a small incision into the patient's thorax. The incision may typically be less than about 15 mm in length, usually less than 12 mm, and often 10 mm or less. The entire procedure may generally be minimally invasive to the patient. In an embodiment, curved portion 30 may be advanced sub-fascially from shaft distal end 102a and around the distal esophagus, DES, of the patient, e.g., substantially as described with reference to FIG. 25.

Although, a thoracic route to placement of curved portion 30 is described with reference to FIG. 26, one of ordinary skill in the art may comprehend that a laparoscopic procedure may alternatively be performed under the invention to achieve substantially the same result, e.g., placement of curved portion 30 at the distal esophagus, DES.

Figure 27A:
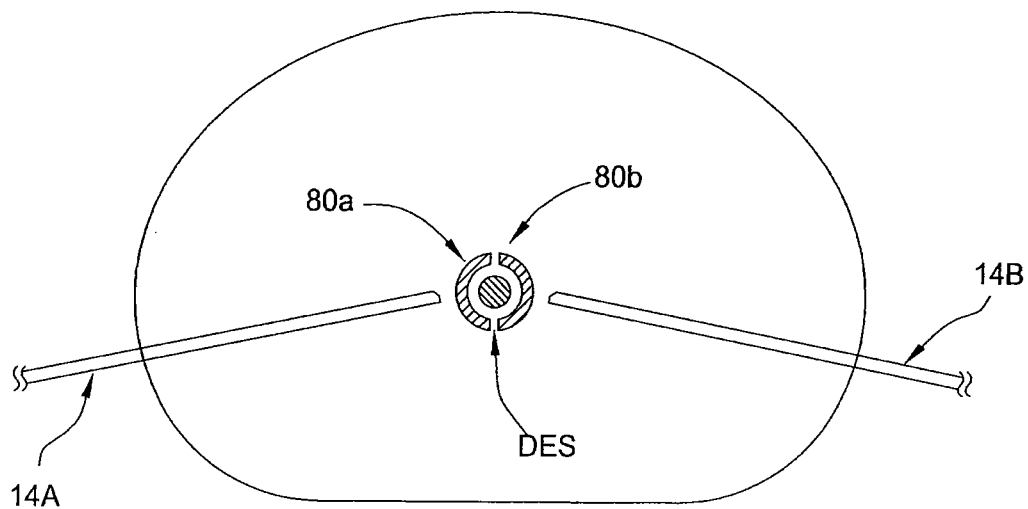
FIG. 27A schematically represents bilateral placement, at the distal esophagus, of a curved portion comprising a plurality of segments, according to another embodiment of the invention.
Figure 27B:
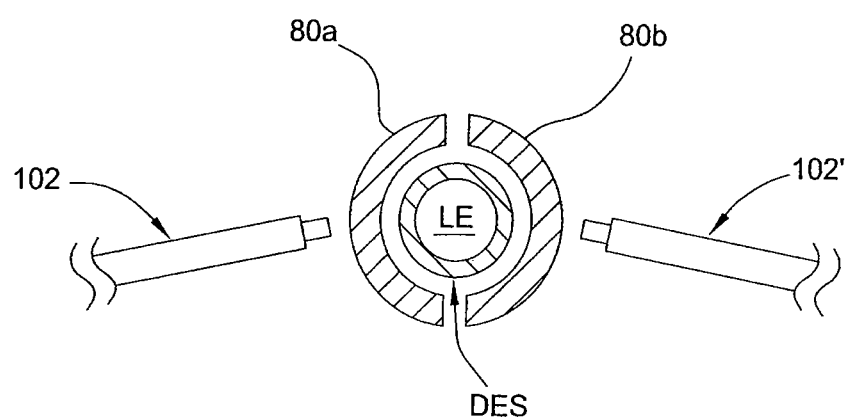
FIG. 27B is an enlarged view showing placement of the curved portion of FIG. 27A.

FIG. 27A schematically represents bilateral placement of a device for treating a patient, according to another embodiment of the invention. In the embodiment of FIG. 27A, a curved portion of the device may be formed at the distal esophagus, DES, by coupling a first arcuate segment 80a and a second arcuate segment 80b. FIG. 27B is an enlarged view showing placement of the first and second arcuate segments 80a, 80b of FIG. 27A extraluminally with respect to the esophagus, i.e., external to the lumen, LE, of the esophagus (see, e.g., FIG. 27B).

With reference to FIGS. 27A-B, first arcuate segment 80a may be introduced within the patient to a first side of the distal esophagus, DES, via a first shaft 102 of a first introducer element 14a. Second arcuate segment 80b may similarly be introduced within the patient to a second side of the distal esophagus via a second shaft 102' of a second introducer element 14b. First arcuate segment 80a and second arcuate segment 80b may be disposed such that each of first and second arcuate segments 80a, 80b at least partially encircles the esophagus. First arcuate segment 80a and second arcuate segment 80b may be coupled together to form a curved portion 30, e.g., substantially as described with reference to FIGS. 16A-B.

Each of first arcuate segment 80a and second arcuate segment 80b may be advanced to the distal esophagus, DES, substantially as described herein for other embodiments of the instant invention, e.g., with reference to FIGS. 25-26. A curved portion 30 formed from first and second arcuate segments 80a, 80b may include various elements, and may possess various features and characteristics, as described herein with reference to other embodiments of the invention (see, e.g., FIGS. 1-24).

Figure 28:
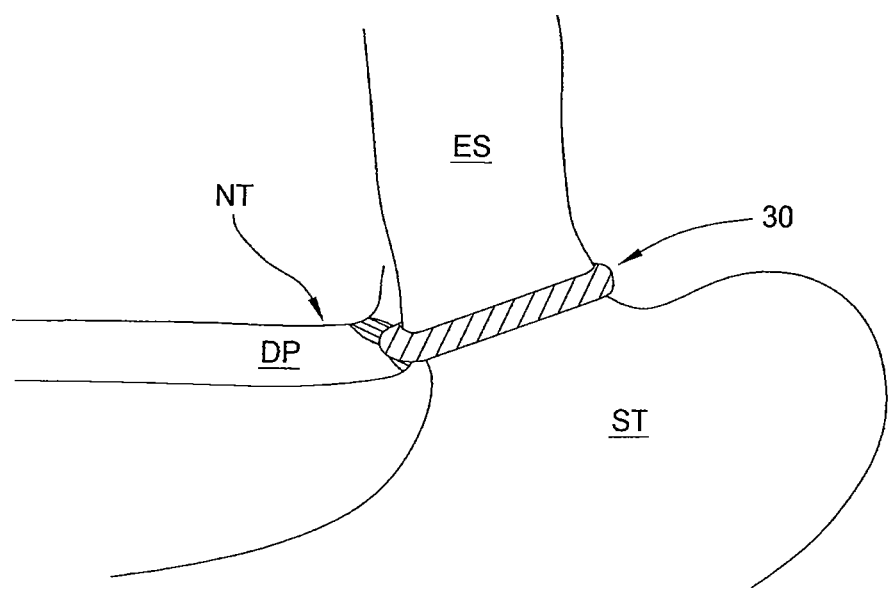
FIG. 28 is a schematic representation showing a curved portion of a device disposed in relation to nerve tissue that innervates the diaphragm of a patient, according to another embodiment of the invention.

FIG. 28 is a schematic representation showing a curved portion 30 of a device for treating a patient, according to another embodiment of the invention. As shown, curved portion 30 may be disposed at the diaphragm, DP, or in at least close proximity to the diaphragm. Curved portion 30 may have various elements and features as described herein with respect to other embodiments of the invention. As an example, curved portion 30 shown in FIG. 28 may be configured for expansion in at least one dimension via transformation from an unexpanded configuration to an expanded configuration.

With further reference to FIG. 28, curved portion 30 is shown in relation to nerve tissue, NT that innervates the diaphragm, DP, of a patient. Expansion of curved portion 30 in at least one dimension, e.g., radially outward expansion of curved portion 30, may exert a mechanical force on the nerve tissue. Such mechanical force may be sufficient to effect mechanical neuromodulation of the nerve tissue. The nerve tissue may comprise sensory nerve tissue. The mechanical force exerted by expansion of curved portion 30 may cause stimulation of the nerve tissue sufficient to mimic fullness of the patient's stomach. Stated differently, mechanical neuromodulation of the nerve tissue according to the embodiment of FIG. 28 may induce a sensation of satiety in the patient. Such a sensation of satiety or fullness may be induced by mechanical neuromodulation of the nerve tissue according to the invention, even though the patient may not have eaten recently or may have consumed only a very modest quantity of food. In an extreme case, mechanical neuromodulation of the nerve tissue by expansion of curved portion 30 may cause thoracic pain in the patient, wherein the pain may radiate from the vicinity of the diaphragm, thereby inducing in the patient the feeling of having eaten to great excess.

According to the invention, the degree of mechanical neuromodulation may be adjusted or calibrated, according to the needs of individual patients. As a non-limiting example, the amount of expansion of curved portion 30 may be adjusted according to an amount of an expansion medium introduced into an expandable element of curved portion 30. According to another non-limiting example, the degree of mechanical neuromodulation effected by curved portion 30 may be adjusted or controlled by adjustment of the diameter of curved portion 30. For example, the diameter of curved portion 30 may be adjusted by passing a filament through a bore within a cannulated curved portion 30 (see, for example, FIGS. 19A-H).

According to another embodiment of the invention, neuromodulation of nerve tissue, NT that innervates the diaphragm, DP, may alternatively be effected by the application of suitable electrical signals (e.g., an applied voltage) via an electrode-bearing embodiment of the invention (see, e.g., FIGS. 20-21, 22A-B) That is to say, in an embodiment of the present invention, a sensation of satiety may alternatively or additionally be induced in the patient via electrical stimulation of sensory nerve tissue that innervates the diaphragm.

Figure 29:
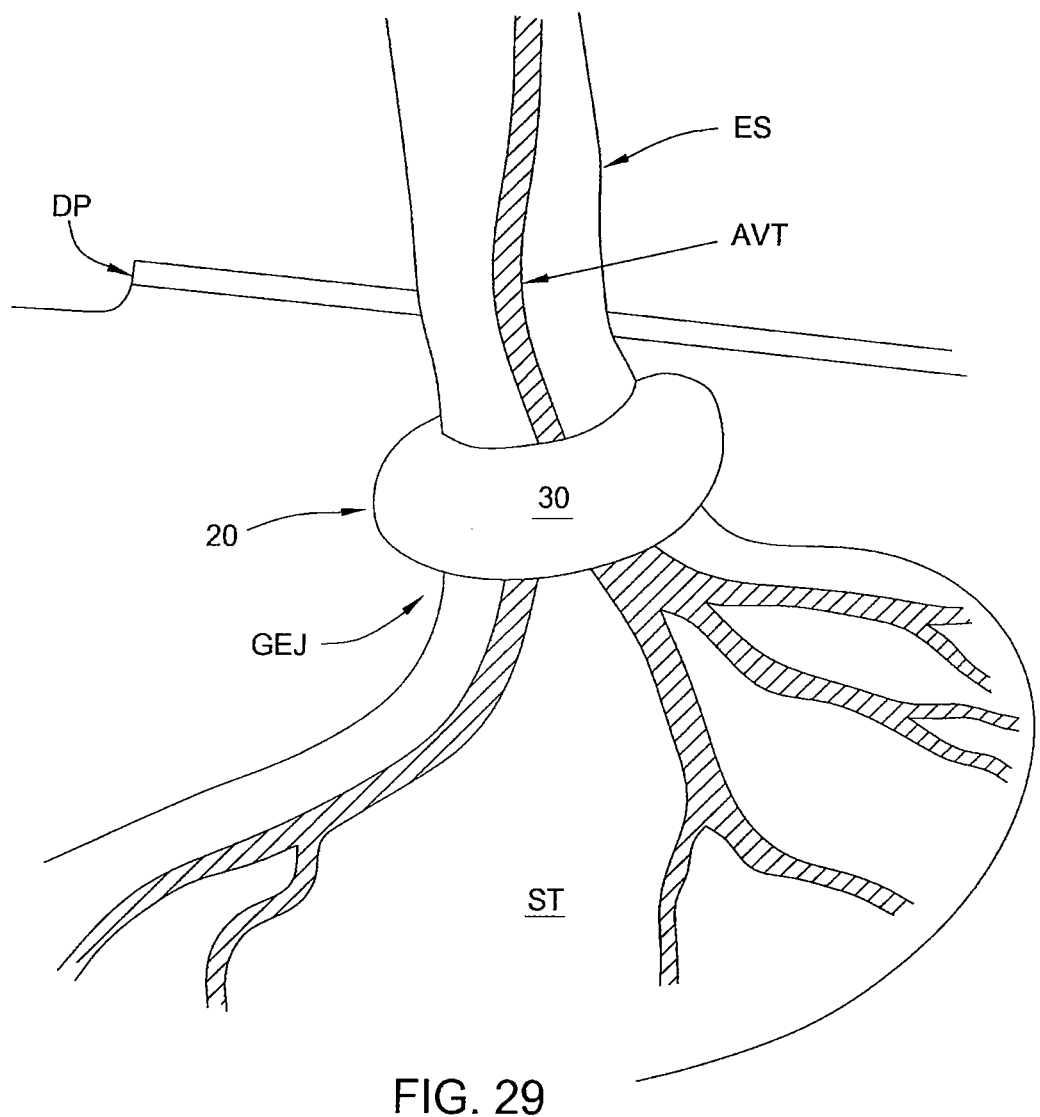
FIG. 29 is a schematic representation showing a device in relation to nerve tissue that innervates the stomach of a patient, according to another embodiment of the invention.

FIG. 29 is a schematic representation showing a device 20 in relation to nerve tissue that innervates the stomach, ST, of a patient, according to an embodiment of the invention. Device 20 includes a curved portion 30 configured for at least partially encircling the esophagus, ES, of the patient. Device 20 and curved portion 30 may each have elements, features, and characteristics as described herein, for example, with reference to FIGS. 1-28.

As shown in FIG. 29, device 20 is disposed around the distal esophagus with the anterior vagal trunk, AVT, disposed internally within curved portion 30. In alternative embodiments, device 20 may be disposed such that one or both of the anterior vagal trunk and the posterior vagal trunk (the latter not shown in FIG. 29) are disposed internally or externally with respect to curved portion 30. Curved portion 30 may be configured for expansion in at least one of a radially inward direction and a radially outward direction. Such expansion may exert a mechanical force on nerve tissue, such as the anterior vagal trunk, sufficient to mechanically neuromodulate the nerve tissue, e.g., the mechanical force applied to the nerve tissue may be sufficient to at least partially block neural transmissions through the nerve tissue.

In the embodiment of FIG. 29, curved portion 30 may be disposed in at least close proximity to the GEJ and/or in at least close proximity to the diaphragm, DP. According to another aspect of the invention, curved portion 30 may be equipped with at least one electrode (the latter not shown in FIG. 29) for electrical neuromodulation of the nerve tissue. Although neuromodulation of nerve tissue that innervates the stomach and the diaphragm is shown separately in FIGS. 28 and 29, respectively, in an embodiment two or more different nerve tissues may be neuromodulated by suitable placement and configuration of a single device 20. As a non-limiting example, a single curved portion 30 may be disposed at the distal esophagus, ES, for neuromodulation of both a first nerve tissue that innervates the stomach and a second nerve tissue that innervates the diaphragm.

Figure 30A:
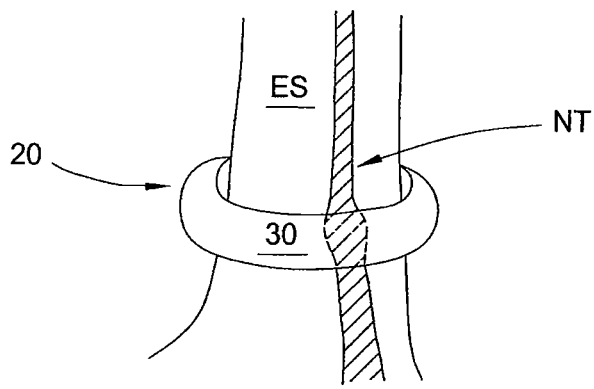
FIG. 30A is a schematic representation of a curved portion of a device disposed at the distal esophagus, with nerve tissue disposed internal to the curved portion, according to another embodiment of the invention.
Figure 30B:
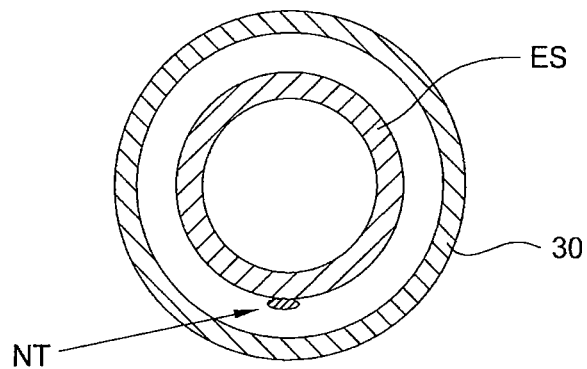
FIG. 30B is a sectional view showing the curved portion of FIG. 30A in relation to the esophagus and nerve tissue, with the curved portion in an unexpanded configuration.

FIG. 30A is a schematic representation of a curved portion 30 of a device 20 disposed around the esophagus, ES, with nerve tissue, NT, disposed internal to curved portion 30, according to another embodiment of the invention. FIG. 30B is a sectional view showing the curved portion 30 of FIG. 30A in relation to the esophagus and nerve tissue, with curved portion 30 in an unexpanded configuration.

Figure 30C:
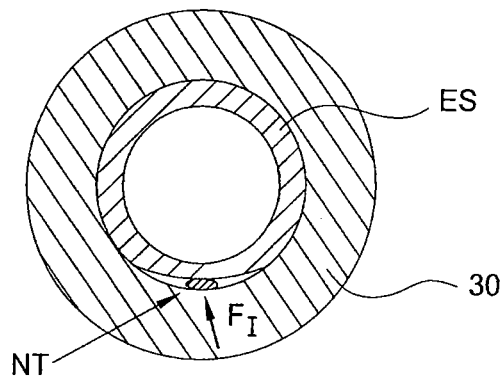
FIG. 30C is a sectional view of the curved portion of FIG. 30A in relation to the esophagus and nerve tissue, showing a mechanical force exerted on the nerve tissue by radially inward expansion of the curved portion, according to an embodiment of the invention.

FIG. 30C is a sectional view of curved portion 30 of FIG. 30A in relation to the esophagus, ES, and nerve tissue, NT, showing radially inward expansion of curved portion 30. Such radially inward expansion of curved portion 30 exerts a mechanical force radially inward, on the nerve tissue. The radially inward mechanical force is represented in FIG. 30C by arrow, $F_I$. Such mechanical force is sufficient to mechanically neuromodulate the nerve tissue. More specifically, mechanical force, $F_I$, is sufficient to at least partially block the transmission of neural impulses via the nerve tissue.

Figure 31A:
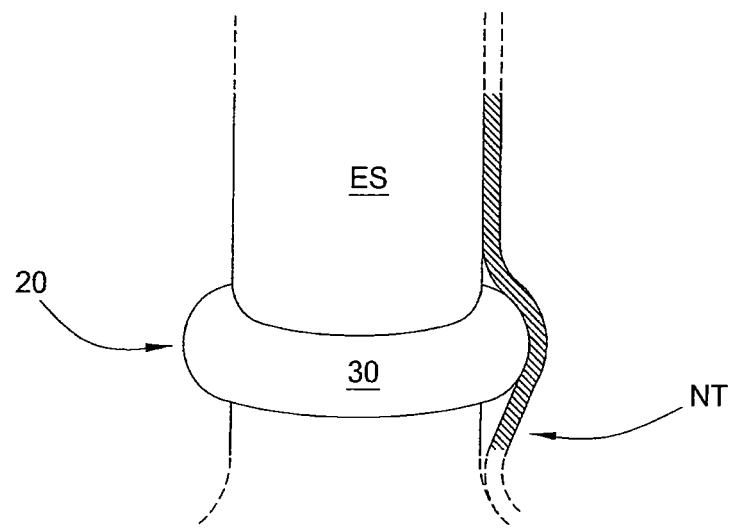
FIG. 31A is a schematic representation showing a curved portion of a device disposed at the distal esophagus, with nerve tissue external to the curved portion, according to another embodiment of the invention.
Figures 31B, 31C:
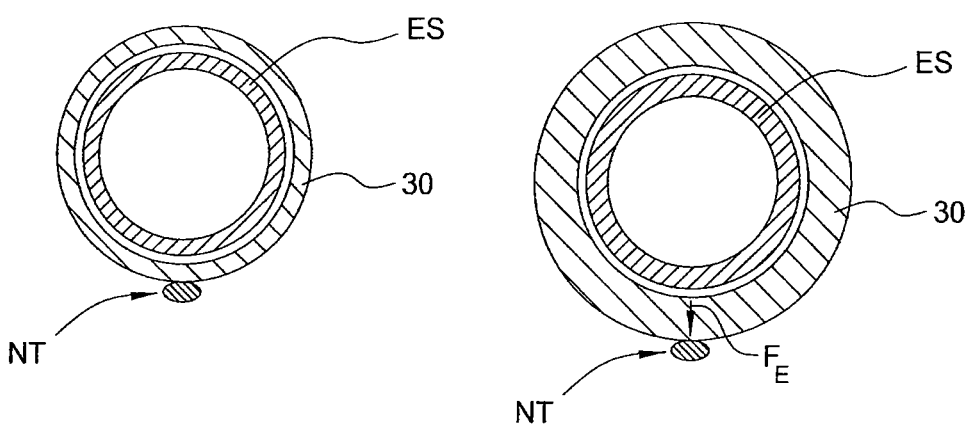
FIG. 31B is a sectional view showing the curved portion of FIG. 31A in relation to the esophagus and nerve tissue, with the curved portion in an unexpanded configuration.
FIG. 31C is a sectional view of the curved portion of FIG. 31A in relation to the esophagus and nerve tissue, showing a mechanical force exerted on the nerve tissue by radially outward expansion of the curved portion, according to another embodiment of the invention.

FIG. 31A is a schematic representation showing a curved portion 30 of a device 20 disposed around the esophagus, ES, with nerve tissue, NT, disposed external to curved portion 30, according to another embodiment of the invention. FIG. 31B is a sectional view showing curved portion 30 of FIG. 31A in relation to the esophagus and nerve tissue, with curved portion 30 in an unexpanded configuration.

FIG. 31C is a sectional view of curved portion 30 of FIG. 31A in relation to the esophagus, ES, and nerve tissue, NT, showing radially outward expansion of curved portion 30. Such radially outward expansion of curved portion 30 exerts a mechanical force radially outward on the nerve tissue. The radially outward mechanical force is represented in FIG. 31C by arrow, $F_E$. Such mechanical force is sufficient to mechanically neuromodulate the nerve tissue; specifically, mechanical force, $F_E$, is sufficient to at least partially block the transmission of neural impulses via the nerve tissue.

Figure 32A:
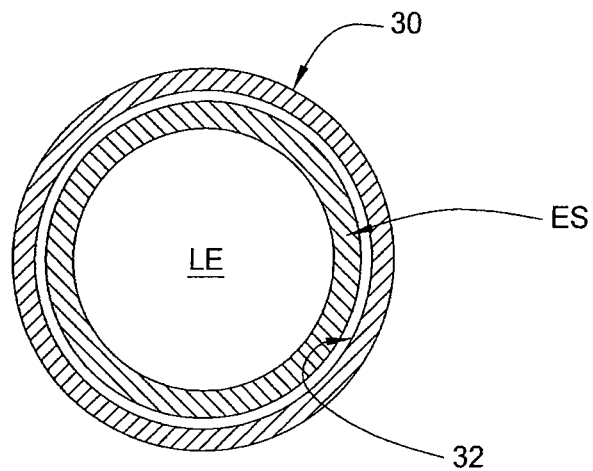
FIG. 32A is a horizontal sectional view schematically representing an unexpanded configuration of a curved portion of a device in relation to the esophagus, according to another embodiment of the invention.
Figure 32B:
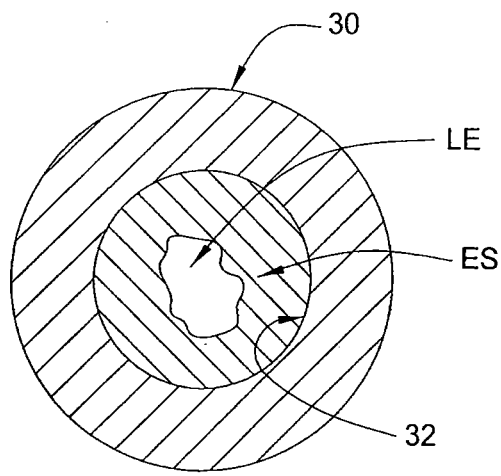
FIG. 32B is a horizontal sectional view schematically representing an expanded configuration of the curved portion of the device in relation to a constricted esophagus, according to the invention.

FIGS. 32A-B each show curved portion 30 in relation to the esophagus, ES, and the lumen, LE, of the esophagus. FIG. 32A is a horizontal sectional view schematically representing an unexpanded configuration of curved portion 30 of a device for treating a patient, according to another aspect of the invention. In an embodiment, the patient may be a GERD patient suffering from reflux of stomach contents into the esophagus. According to another aspect of the invention, the patient may be an obesity patient. Of course, one skilled in the art will realize that obesity patient's frequently also suffer from GERD, and that GERD patient's are frequently obese.

As shown in FIGS. 32A-B, curved portion 30 is disposed extraluminally with respect to the esophagus and completely encircles the esophagus. Curved portion 30 may be substantially annular. In other embodiments of the present invention, curved portion 30 may partially encircle the esophagus. Such partial encirclement of the esophagus by curved portion 30 may nevertheless be sufficient to constrict the lumen, LE, of the esophagus. In an embodiment, curved portion 30 is configured for controlled or adjustable expansion thereof, whereby curved portion 30 may be expanded radially inward. Mechanisms for effecting radially inward adjustment, as well as radially outward adjustment, of a curved portion 30 of the instant invention are described hereinabove (see, e.g., FIGS. 9-10, 11A-D, 19A-H).

According to an aspect of the invention, radially inward expansion of curved portion 30 may occur in the absence, or substantially in the absence, of radially outward expansion of curved portion 30. Curved portion 30 includes a radially inner surface 32. Curved portion 30 may further include various elements and features as disclosed for other embodiments of the invention, e.g., as described herein with respect to FIGS. 1-24.

FIG. 32B is a horizontal sectional view schematically representing an expanded configuration of curved portion 30, wherein radially inward expansion of curved portion 30 causes radially inner surface 32 to exert a mechanical force radially inward on the esophagus, ES, whereby the lumen, LE, of the esophagus may be at least substantially constricted. The degree of constriction of the lumen of the esophagus may be adjusted or controlled by adjusting the amount of radially inward expansion of curved portion 30. In an embodiment, constriction of the lumen of the esophagus may be adjusted to restrict the passage of food through the esophagus and into the stomach of an obesity patient, whereby the patient may reduce their caloric intake and hence lose excess weight.

In another embodiment, constriction of the lumen of the esophagus via curved portion 30 may be adjusted to prevent or inhibit reflux of stomach contents into the esophagus, thereby preventing or treating GERD in the patient. In an embodiment, curved portion 30 for the treatment of obesity and/or GERD according to FIGS. 32A-B may be disposed sub-fascially at the distal part of the esophagus in at least close proximity to the gastro-esophageal junction, and curved portion 30 may be retained in situ around the esophagus externally by the fascia and internally by the muscular layers of the esophagus (see, e.g., FIGS. 24A-B).

Figure 33:
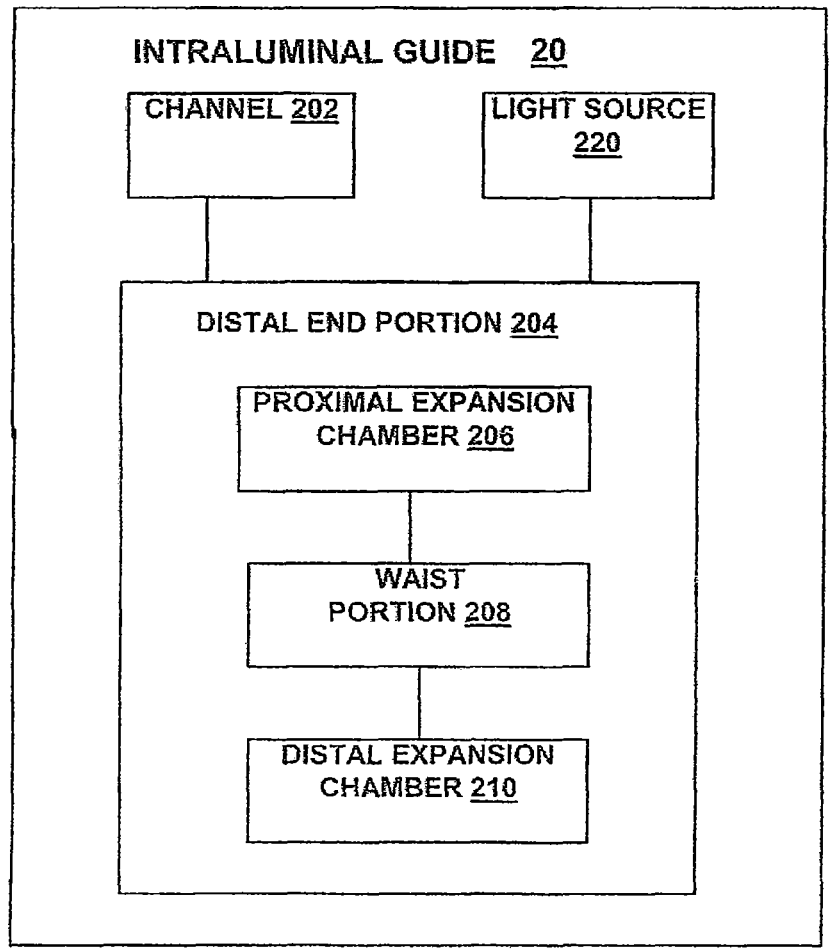
FIG. 33 is a block diagram schematically representing an intraluminal guide for guiding placement of an extraluminal device in a patient, according to another embodiment of the invention.

FIG. 33 is a block diagram schematically representing an intraluminal guide 16 for treating a patient, according to another embodiment of the invention. Intraluminal guide 16 is configured for guiding the placement of an extraluminal device in a patient. The extraluminal device may be a device 20 or a curved portion 30 of device 20 as described herein, e.g., with reference to FIGS. 1-32B. Intraluminal guide 16 includes a channel 202, and an expandable distal end portion 204. Distal end portion 204 includes a proximal expansion chamber 206, a waist portion 208, and a distal expansion chamber 210.

With further reference to FIG. 33, intraluminal guide 16 may be equipped with a light source 220 suitable for illuminating at least distal end portion 204. As an example, light source 220 may be configured for illuminating at least one of proximal expansion chamber 206, waist portion 208, and distal expansion chamber 210. In an embodiment, light source 220 may be configured for extraluminally illuminating at least one tissue or organ, wherein the tissue or organ may be targeted for treatment by the extraluminal device. As a non-limiting example, light source 220 may be configured for illuminating a nerve or nerve tissue disposed external to the esophagus.

FIGS. 34A-C are side views schematically representing unexpanded, partially expanded, and expanded configurations, respectively, of an intraluminal guide 16, according to an embodiment of the invention. As shown in FIGS. 34A-C, intraluminal guide 16 may include a channel 202, an expandable distal end portion 204, a proximal expansion chamber 206, a waist portion 208, and a distal expansion chamber 210, substantially as described with reference to FIG. 33.

With further reference to FIGS. 34A-C, channel 202 extends proximally from proximal expansion chamber 206. Channel 202 may be in fluid communication with distal end portion 204. Channel 202 may be configured for the passage of an inflation medium therethrough for expanding at least one of distal expansion chamber 210 and proximal expansion chamber 206. As an example, distal expansion chamber 210 and proximal expansion chamber 206 may be expanded by passage of a suitable fluid through channel 202. Such fluid may comprise a liquid, a gas, or a mixture thereof. Distal expansion chamber 210 is in communication with proximal expansion chamber 206 via waist portion 208. Each of distal expansion chamber 210 and proximal expansion chamber 206 may be substantially globular or discoid when at least partially expanded. As a non-limiting example, distal expansion chamber 210 may be substantially globular, and proximal expansion chamber 206 may be substantially discoid. Intraluminal guide 16 may further include an internal surface 16a, and light source 220 (not shown in FIGS. 34A-C) may be disposed within internal surface 16a.

FIGS. 35A-B schematically represent unexpanded and expanded configurations, respectively, of intraluminal guide 16 disposed intraluminally in relation to the esophagus, ES, according to one aspect of the invention. With reference to FIG. 35A, the unexpanded conformation of distal end portion 204 is configured for intraluminal passage within the esophagus. For example, distal end portion 204 may be passed via the patient's mouth intraluminally within the esophagus to the distal esophagus.

With reference to FIG. 35B, distal expansion chamber 206 and proximal expansion chamber 210 are configured for intraluminal expansion within the esophagus. In the expanded conformation, intraluminal guide 16 is configured for guiding placement of an extraluminal device, e.g., curved portion 30, around the esophagus of a patient (see, e.g., FIGS. 25 and 36). In an embodiment, when intraluminal guide 16 is expanded at the distal esophagus, curved portion 30 may be advanced around waist portion 208 for placement of curved portion 30 extraluminally around the esophagus. Light source 220 may be configured for illuminating at least waist portion 208 of guide 16.

In an embodiment, light source 220 may be further configured for the illumination of at least one tissue or organ, wherein the tissue or organ illuminated may be disposed external to the lumen, LE, of the esophagus, ES. Illumination from light source 220 may aid the surgeon in locating intraluminal guide 16 and in extraluminal placement of curved portion 30 with respect to the esophagus. In an embodiment, curved portion 30 may be implanted extraluminally with respect to the esophagus while being embedded within esophageal tissue. As a non-limiting example, curved portion 30 may be implanted between a fascial layer and a muscular layer of the esophagus.

Figure 36:
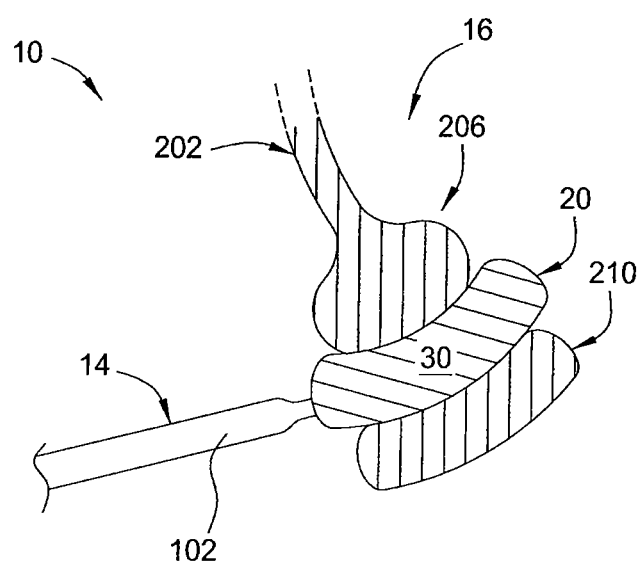
FIG. 36 is a perspective view schematically representing a system including a curved portion of a device in relation to an introducer element and an intraluminal guide, according to another embodiment of the invention.

FIG. 36 is a perspective view schematically representing a system 10 for treating a patient, according to another embodiment of the invention. System 10 may include a curved portion 30 of a device 20, an intraluminal guide 16, and an introducer element 14 having a shaft 102 (see, e.g., FIG. 7A). Only the distal portion of introducer element 14 is shown in FIG. 36. Introducer element 14 may have elements and features as described hereinabove, e.g., as described with reference to FIGS. 7A-C and FIG. 26.

Intraluminal guide 16 is expanded such that waist portion 208 (FIGS. 34C, 35B) serves to guide curved portion 30 along a path defined between proximal expansion chamber 206 and distal expansion chamber 210. Such a path followed by curved portion 30 may be at least substantially annular (see, e.g., FIG. 25). When intraluminal guide 16 is placed and expanded intraluminally within the esophagus, such a path may be further defined as being between the fascial and muscular layers of the esophagus (see, e.g., FIGS. 24A-B). The esophagus is omitted from FIG. 36 for the sake of clarity.

As disclosed hereinabove, device 20 may be in a linear conformation during passage within shaft 102, and may be transformed to a substantially arcuate conformation during advancement around the esophagus (see, e.g., FIGS. 5A-C and 7A-C). Device 20 may be transformed from the linear conformation to the arcuate conformation during advancement around waist portion 208, wherein the arcuate conformation forms curved portion 30. After placement of curved portion 30 via intraluminal guide 16, curved portion 30 may at least partially encircle the distal esophagus of the patient.

Figure 37:
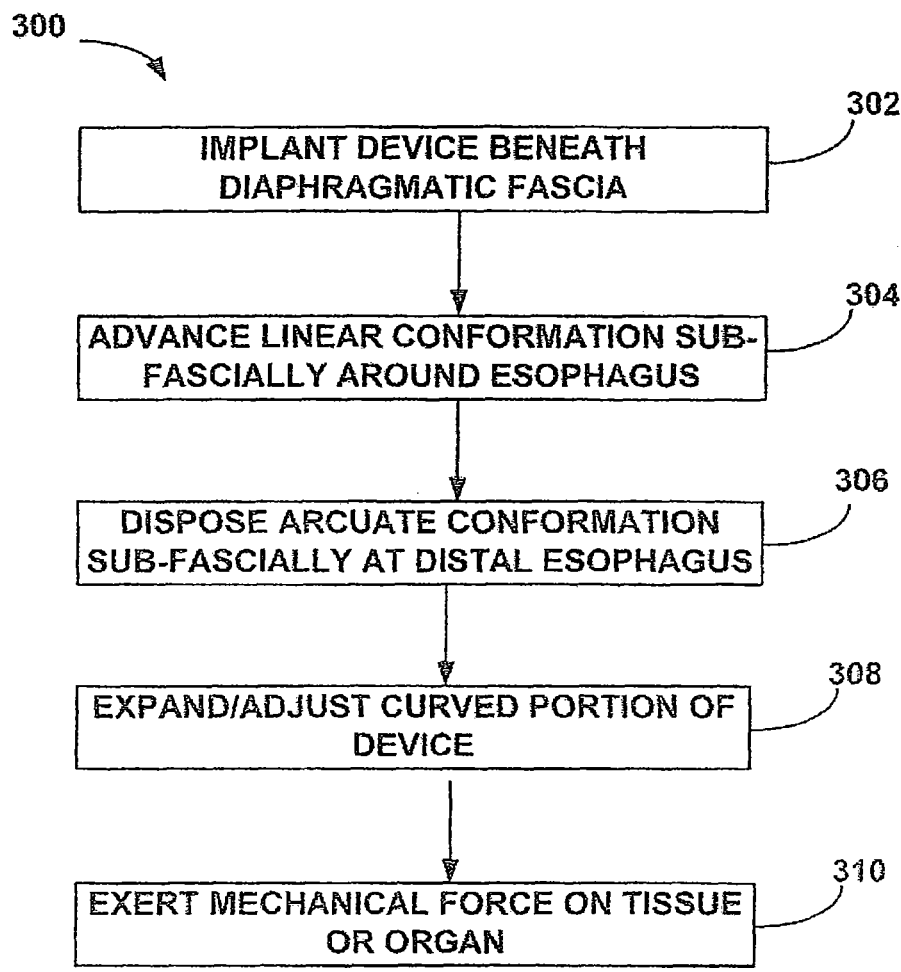
FIG. 37 is a flow diagram schematically representing a series of steps involved in a method for treating a patient, according to another embodiment of the invention.

FIG. 37 is a flow diagram schematically representing a series of steps involved in a method 300 for treating a patient, according to another embodiment of the invention. Step 302 involves implanting a device beneath the diaphragmatic fascia of the patient. As an example, the device may comprise apparatus for treating obesity. In another example, the device may comprise apparatus for treating GERD. The device may be transformable between a linear conformation and an arcuate conformation.

Step 304 involves advancing the linear conformation around the esophagus. The linear conformation may be advanced sub-fascially, i.e., beneath a fascia of the patient, such as the diaphragmatic fascia and/or the esophageal fascia. During, or as a result of, advancement of the device around the esophagus, the device may undergo transformation from the linear conformation to the arcuate conformation. Step 306 involves disposing the arcuate conformation of the device at the distal esophagus, wherein the device may be disposed sub-fascially beneath the diaphragmatic fascia or the esophageal fascia. The device may include a curved portion, for example, as described with reference to FIGS. 2-24.

Step 308 involves expanding or adjusting the curved portion of the device. The curved portion may be expanded or adjusted via various mechanisms (see, e.g., FIGS. 11A-D, 19A-H). The curved portion may be expanded or adjusted in one dimension, or more than one dimension. For example, the curved portion may be expandable radially outward independently of any radially inward expansion; or, the curved portion may be expandable radially inward independently of any radially outward expansion; or, the curved portion may be expandable radially outward and radially inward concurrently and/or independently of each other.

Step 310 involves exerting a mechanical force, via the curved portion, on at least one tissue or organ of the patient. Such a tissue or organ may comprise the esophagus or a nerve tissue. The mechanical force may be sufficient to effectively treat a patient, such as a GERD patient or an obesity patient (see, e.g., FIGS. 38, 45, 46).

Figure 38:
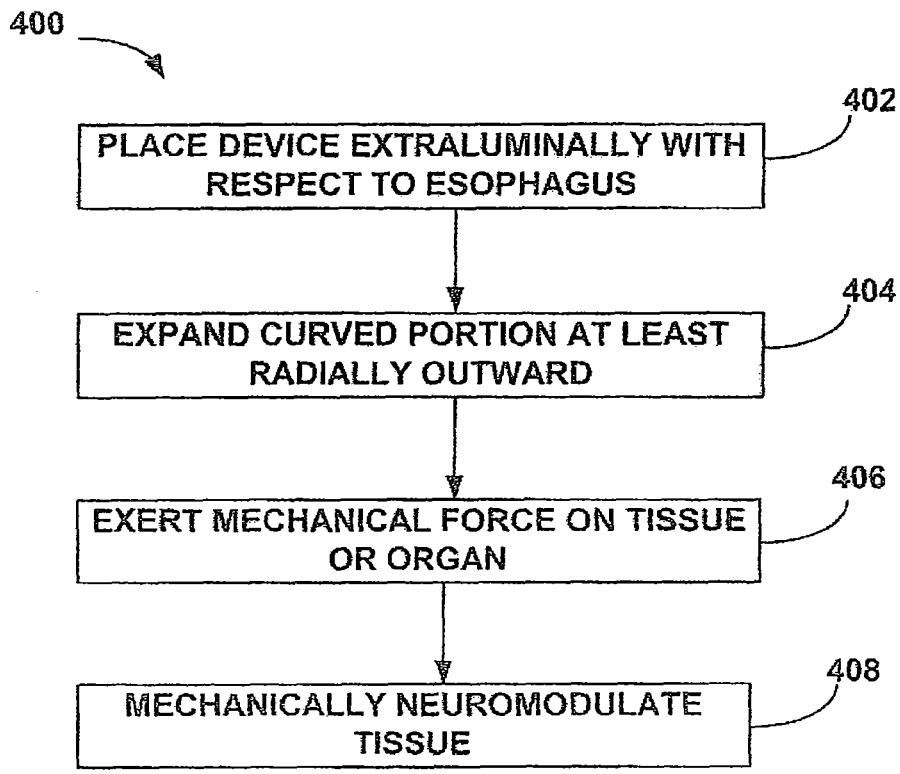
FIG. 38 is a flow diagram schematically representing a series of steps involved in a method for treating a patient, according to another embodiment of the invention.

FIG. 38 is a flow diagram schematically representing a series of steps involved in a method 400 for treating a patient, according to another embodiment of the invention. Step 402 involves placing a device extraluminally with respect to the esophagus of the patient. The device may include a curved portion, for example, as described with reference to FIGS. 2-24. The device may further include various elements and features as disclosed for other embodiments of the invention, e.g., as described herein with respect to FIGS. 1-24. The curved portion may be expandable or adjustable in one or more dimensions, e.g., as described with reference to FIGS. 11A-D, 19A-H.

Step 404 involves expanding the curved portion in at least a radially outward direction or dimension. Step 406 involves exerting a mechanical force on at least one tissue or organ of the patient. As an example, the mechanical force may be exerted by radially outward expansion of the curved portion. The tissue or organ may comprise a tissue targeted by a physician for treatment of the patient. As non-limiting examples, the tissue or organ may comprise nerve tissue or the diaphragm of the patient. The mechanical force may be sufficient to effectively treat the patient. The patient may be an obesity patient or a GERD patient, for example.

Step 408 involves mechanically neuromodulating one or more tissues or organs. As an example, step 408 may comprise at least partially blocking nerve tissue that innervates the GI tract. In an embodiment, step 408 may comprise at least partially blocking (via exertion of the mechanical force) nerve tissue that innervates the stomach, such that the patient experiences a decrease in gastric motility, a decrease in gastric enzyme secretion, or a decrease in gastric acid secretion. In an embodiment, the nerve tissue may comprise at least one vagal trunk (i.e. the anterior and/or posterior vagal trunk) of the vagus nerve.

In another embodiment, step 408 may comprise stimulating nerve tissue that innervates the diaphragm, whereby the patient may experience a sensation of satiety or fullness. Of course, it is to be understood that the invention is not limited to mechanical neuromodulation of nerve tissue that innervates the stomach or the diaphragm. According to the invention, other motor or sensory nerves, nerve tissue, or nerve plexus, including sympathetic and parasympathetic nerve tissue, may be mechanically and/or electrically neuromodulated for the effective treatment of obesity and/or GERD (see, e.g., FIG. 44).

Figure 39:
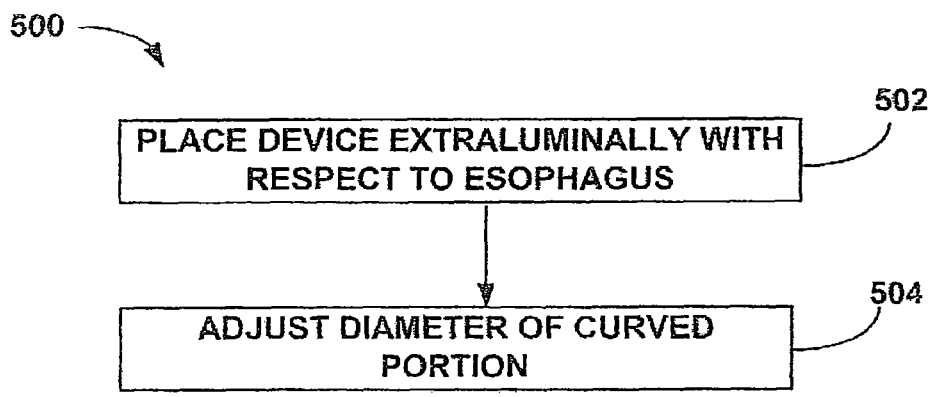
FIG. 39 is a flow diagram schematically representing a series of steps involved in a method for treating a patient, according to another embodiment of the invention.

FIG. 39 is a flow diagram schematically representing a series of steps involved in a method 500 for treating a patient, according to another embodiment of the invention. Step 502 involves placing a device extraluminally with respect to the esophagus of the patient, i.e., the device is disposed external to the lumen of the esophagus. The device may include a curved portion, as well as various additional elements and features disclosed herein for other embodiments of the invention, e.g., with respect to FIGS. 1-24. As an example, step 502 may be performed substantially as described for steps 302-306 of method 300 (FIG. 37).

Step 504 involves adjusting the diameter of the curved portion. In an embodiment, step 504 may comprise decreasing an internal diameter of the curved portion by radially inward expansion of the curved portion (see, e.g., FIGS. 11C-D), or step 504 may comprise increasing an external diameter of the curved portion by radially outward expansion of the curved portion (see, e.g., FIGS. 11B, 11D). In another embodiment, the curved portion may be cannulated, and step 504 may comprise adjusting (controllably increasing or decreasing) the diameter of the curved portion by the controlled passage of a filament within the curved portion.

Adjustment of the diameter of the curved portion according to step 504 may exert a force on at least one tissue or organ sufficient to treat a patient. For example, the exerted mechanical force may mechanically neuromodulate a nerve tissue for the treatment of obesity or GERD, e.g., substantially as described with respect to step 408 of method 400 (FIG. 38). According to another aspect of the invention, the mechanical force may be exerted radially inward on the esophagus such that the lumen of the esophagus is constricted. Constriction of the lumen of the esophagus may effectively treat obesity and/or GERD (see, e.g., FIGS. 32A-B and 45-46).

Figure 40:
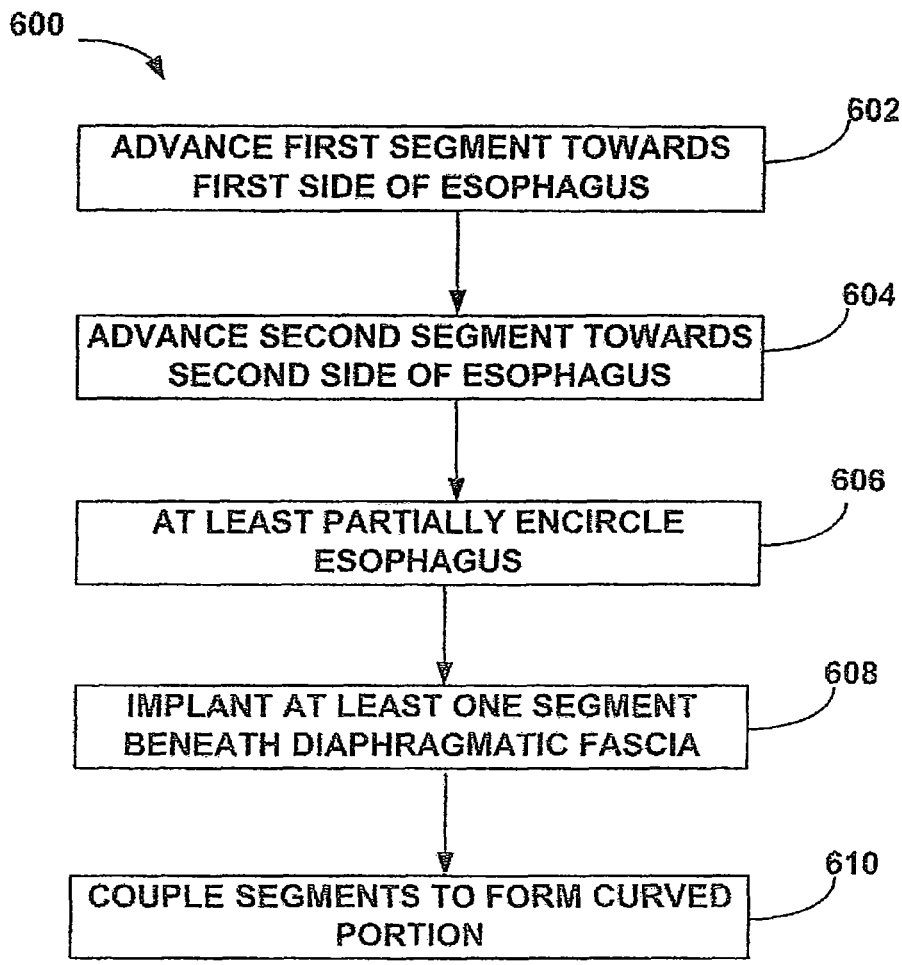
FIG. 40 is a flow diagram schematically representing a series of steps involved in a method for treating a patient, according to another embodiment of the invention.

FIG. 40 is a flow diagram schematically representing a series of steps involved in a method 600 for treating a patient, according to another embodiment of the invention. According to one aspect of the invention, method 600 may be used for placing a curved portion of a device around the esophagus, wherein the curved portion is formed by coupling a plurality of segments. Each segment may be substantially arcuate, or may be transformable to an arcuate conformation. In an embodiment, the segments may be introduced into the patient bilaterally, e.g., from both sides of the patient's thorax or abdomen (see, e.g., FIGS. 27A-B).

Step 602 involves advancing a first segment towards a first side of the esophagus. Step 604 involves advancing a second segment towards a second side of the esophagus. Step 606 involves at least partially encircling the esophagus with the first segment and the second segment. In an embodiment, the curved portion comprises the first segment coupled to the second segment (see, e.g., FIGS. 16A-B). In an embodiment, method 600 may further involve implanting at least one of the first segment and the second segment beneath a fascia, at step 608. The fascia may comprise, for example, the diaphragmatic fascia of the patient. Step 608 may be performed before, or concurrently with, step 606. Step 610 involves coupling the first and second segments to form the curved portion, such that the curved portion at least partially encircles the esophagus.

Figure 41:
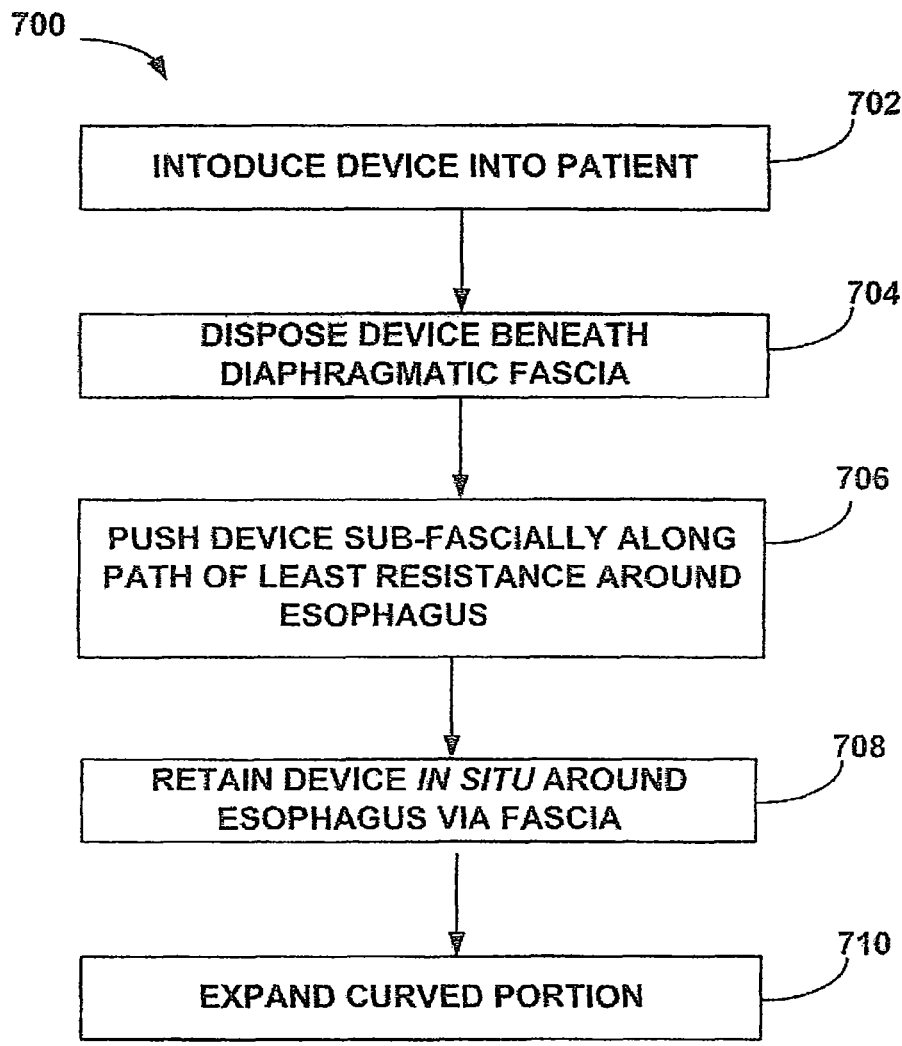
FIG. 41 is a flow diagram schematically representing a series of steps involved in a method for treating a patient, according to another embodiment of the invention.

FIG. 41 is a flow diagram schematically representing a series of steps involved in a method 700 for treating a patient, according to another embodiment of the invention. Step 702 involves introducing a device into the patient. The device may be introduced into the patient via an introducer element, e.g., as described herein with reference to FIGS. 7A-C and FIG. 26. The device may be introduced into the patient to treat a condition such as obesity or GERD. The device may include a curved portion, as well as various additional elements and features as disclosed herein for other embodiments of the invention, e.g., with reference to FIGS. 1-24.

Step 704 involves disposing or implanting the device beneath the diaphragmatic fascia of the patient. The device may be configured for transformation from a linear conformation to an arcuate conformation. The linear conformation of the device may be advanced distally within a shaft of the introducer element, and the device may be disposed beneath the fascia while in the linear conformation.

Step 706 involves pushing the device sub-fascially along a path of least resistance, such that the device is transformed from the linear conformation to the arcuate conformation as the device is advanced, e.g., annularly, around the esophagus. Step 708 involves retaining the device in situ by the fascia.

Step 710 involves expanding the curved portion of the device in at least one dimension sufficient to exert a mechanical force on at least one tissue or organ of the patient. In an alternative embodiment (not shown in FIG. 41), such a mechanical force may be exerted on the tissue or organ by adjustable contraction of the curved portion wherein both an internal diameter and an external diameter of the curved portion are decreased. According to an aspect of method 700, the device may be implanted such that no part of the device, including an expanded configuration of the curved portion, contacts the stomach of the patient.

Figure 42:
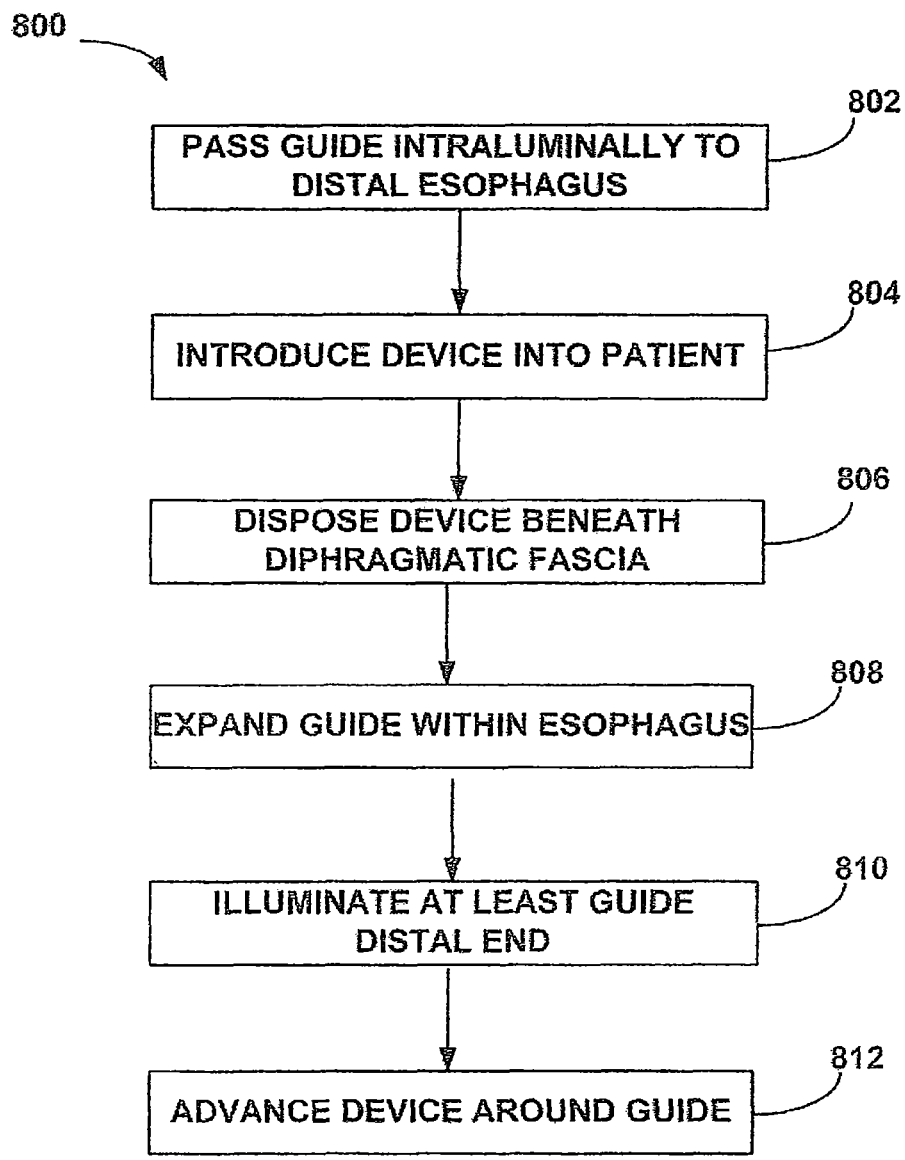
FIG. 42 is a flow diagram schematically representing a series of steps involved in a method for treating a patient, according to another embodiment of the invention.

FIG. 42 is a flow diagram schematically representing a series of steps involved in a method 800 for treating a patient, according to another embodiment of the invention. According to an aspect of the invention, method 800 may be used for placing a curved portion of a device around the esophagus with the aid of an intraluminal guide disposed within the esophagus.

Step 802 involves passing the intraluminal guide intraluminally to the distal esophagus. The intraluminal guide may include an expandable distal end in communication with a proximal channel (see, e.g., FIGS. 34A-C). The intraluminal guide may further include various additional elements and features as disclosed herein, for example, with respect to FIGS. 33, and 34A-C. In step 802, the intraluminal guide may be passed intraluminally in the form of an unexpanded conformation (see, e.g., FIG. 35A) to a location in at least close proximity to the GEJ.

Step 804 involves introducing the device into the patient, e.g., via an introducer element (see, e.g., FIG. 26). The device may be placed extraluminally with respect to the esophagus. In an embodiment, in step 804 the device may be disposed beneath the diaphragmatic fascia of the patient. The device may include a curved portion, as well as various additional elements and features as disclosed herein for other embodiments of the invention, e.g., with respect to FIGS. 1-24. Step 806 involves disposing the device beneath the diaphragmatic fascia. Step 806 may comprise placing the device in at least close proximity to the GEJ. Steps 804 and 806 may otherwise be performed substantially as described for steps 702 and 704, respectively, of method 700 (FIG. 41).

Step 808 involves at least partially expanding at least a portion of the intraluminal guide intraluminally within the esophagus. In an embodiment, step 808 may involve passing a fluid within the channel of the intraluminal guide for inflation of the distal end portion of the intraluminal guide.

The intraluminal guide may include a light source (see, e.g., FIG. 33). Method 800 may include a step 810 of illuminating at least the distal end portion of the intraluminal guide. Step 812 involves advancing the device around the intraluminal guide, such that the device is placed around the esophagus. In an embodiment, step 808 may involve expanding both a distal expansion chamber and a proximal expansion chamber, thereby defining a waist portion disposed at least substantially axially between the distal and proximal expansion chambers (see, e.g., FIGS. 34C and 36). In an embodiment, step 812 may involve advancing the device around the esophagus along an annular path located radially outward from the waist portion. Step 812 may be aided via illumination provided in step 810.

Figure 43:
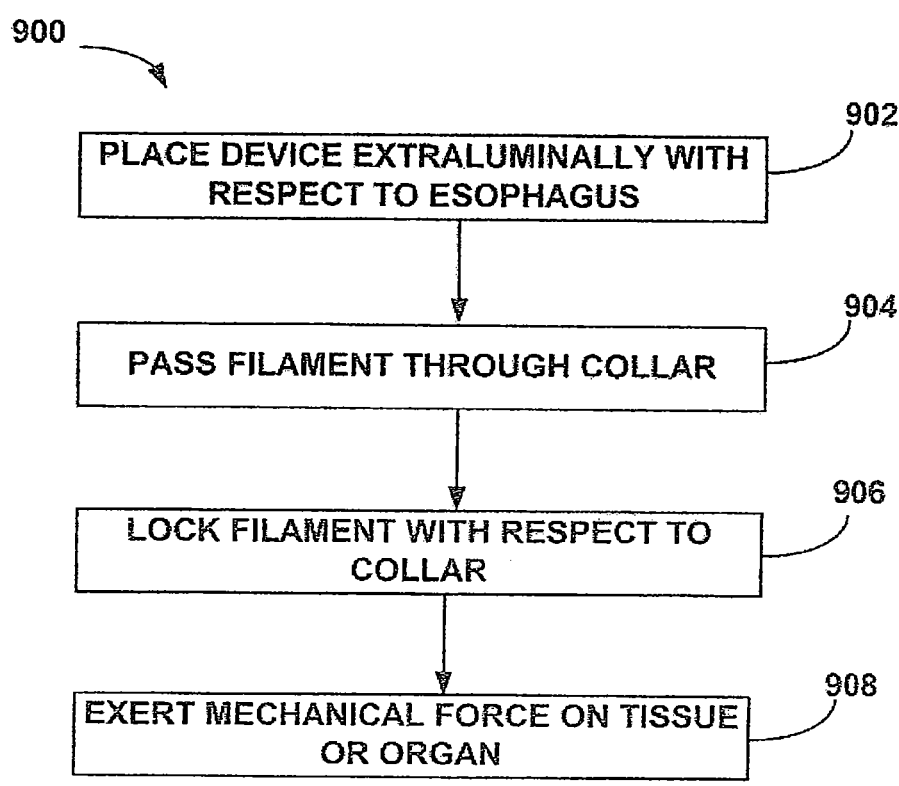
FIG. 43 is a flow diagram schematically representing a series of steps involved in a method for treating a patient, according to another embodiment of the invention.

FIG. 43 is a flow diagram schematically representing a series of steps involved in a method 900 for treating a patient using a cannulated device, according to another embodiment of the invention. Step 902 involves placing the cannulated device extraluminally with respect to the esophagus. In an embodiment, step 902 may comprise embedding the device within esophageal tissue at the distal esophagus. The device may include an adjustable curved portion configured for radially inward or radially outward movement of a curved portion, wherein the internal diameter and external diameter of the curved portion may be adjusted by passing a filament within the curved portion (see, e.g., FIGS. 19A-D and 19F-G).

The cannulated device placed according to step 902 may be configured for exerting a mechanical force on at least one tissue or organ via the radially inward or radially outward movement of the curved portion. The cannulated device may further include a collar configured for slidably accommodating a first strand and a second strand of the filament when the collar is in an unlocked configuration. The diameter of the curved portion may be adjusted by passing at least one of the first and second strands of the filament within the collar. The filament may be locked in relation to the collar, and/or in relation to the curved portion, when the collar is in a locked configuration. The cannulated device may further include various additional elements and features as disclosed herein, for example, with respect to FIGS. 19A-H.

Step 904 involves passing the filament, in a controlled manner, through a bore in the curved portion, whereby the diameter of the curved portion may be adjusted. The diameter of the curved portion may be adjusted, either by increasing or decreasing the diameter of the curved portion. The diameter of the curved portion may be adjusted to a diameter suitable for exerting a mechanical force on a targeted tissue or organ. Step 906 involves locking the collar with respect to the filament, whereby the diameter of the curved portion may remain constant. Step 908 involves exerting a suitable mechanical force, via the curved portion, on the targeted tissue or organ. As an example, when a targeted tissue or organ is disposed internal to the curved portion, a mechanical force may be exerted on the tissue or organ by decreasing the diameter of the curved portion. Conversely, for a tissue or organ disposed external to the curved portion, a mechanical force may be exerted on the tissue or organ by increasing the diameter of the curved portion. The mechanical force may treat the patient by mechanical neuromodulation of a targeted nerve tissue or by mechanical constriction of the esophagus, essentially as described hereinabove with respect to other embodiments and methods of the instant invention.

Figure 44:
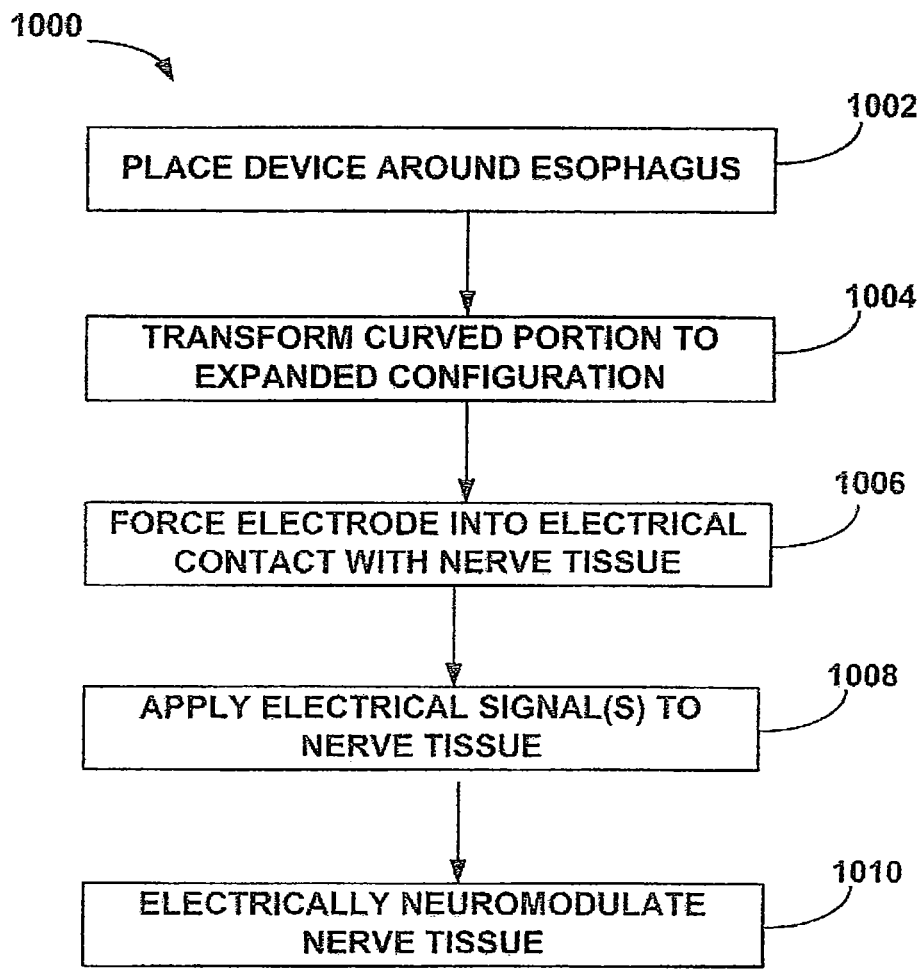
FIG. 44 is a flow diagram schematically representing a series of steps involved in a method for treating a patient, according to another embodiment of the invention.

FIG. 44 is a flow diagram schematically representing a series of steps involved in a method 1000 for treating a patient by electrical neuromodulation, according to another embodiment of the invention. Step 1002 involves placing a device around the esophagus, wherein the device is equipped with at least one electrode configured for applying an electrical signal to a nerve tissue for electrical neuromodulation of the nerve tissue. The device may include an expandable curved portion, and the electrode may be disposed on an external surface of the curved portion.

Step 1004 involves transforming the curved portion from an unexpanded configuration to an expanded configuration. Step 1006 involves forcing the electrode into contact with the nerve tissue to enhance or ensure electrical contact between the electrode and the nerve tissue. The electrode may be forced into contact with the nerve tissue via expansion of the curved portion according to step 1004. Step 1008 involves applying one or more electrical signals to the nerve tissue.

Step 1010 involves electrically neuromodulating the nerve tissue via the applied electrical signals. The nerve tissue may comprise motor nerve tissue or sensory nerve tissue. The nerve tissue may be sympathetic nerve tissue or sympathetic nerve tissue. The nerve tissue may be a nerve fiber or a nerve plexus. The nerve tissue may innervate the diaphragm of the patient or the GI tract of the patient. The nerve tissue may be the anterior vagal trunk or the posterior vagal trunk. In an embodiment, the electrical neuromodulation effected via step 1010 may cause at least partial blocking of the transmission of neural impulses in the nerve tissue. As a non-limiting example, step 1010 may cause at least partial blocking of neural impulses in nerve tissue that innervates the stomach, such that the patient experiences decreased gastric motility, decreased gastric enzyme production, or decreased gastric acid production. In another embodiment, the electrical neuromodulation effected via step 1010 may stimulate the transmission of neural impulses, e.g., in nerve tissue that innervates the diaphragm, such that the patient experiences a sensation of satiety or fullness.

Figure 45:
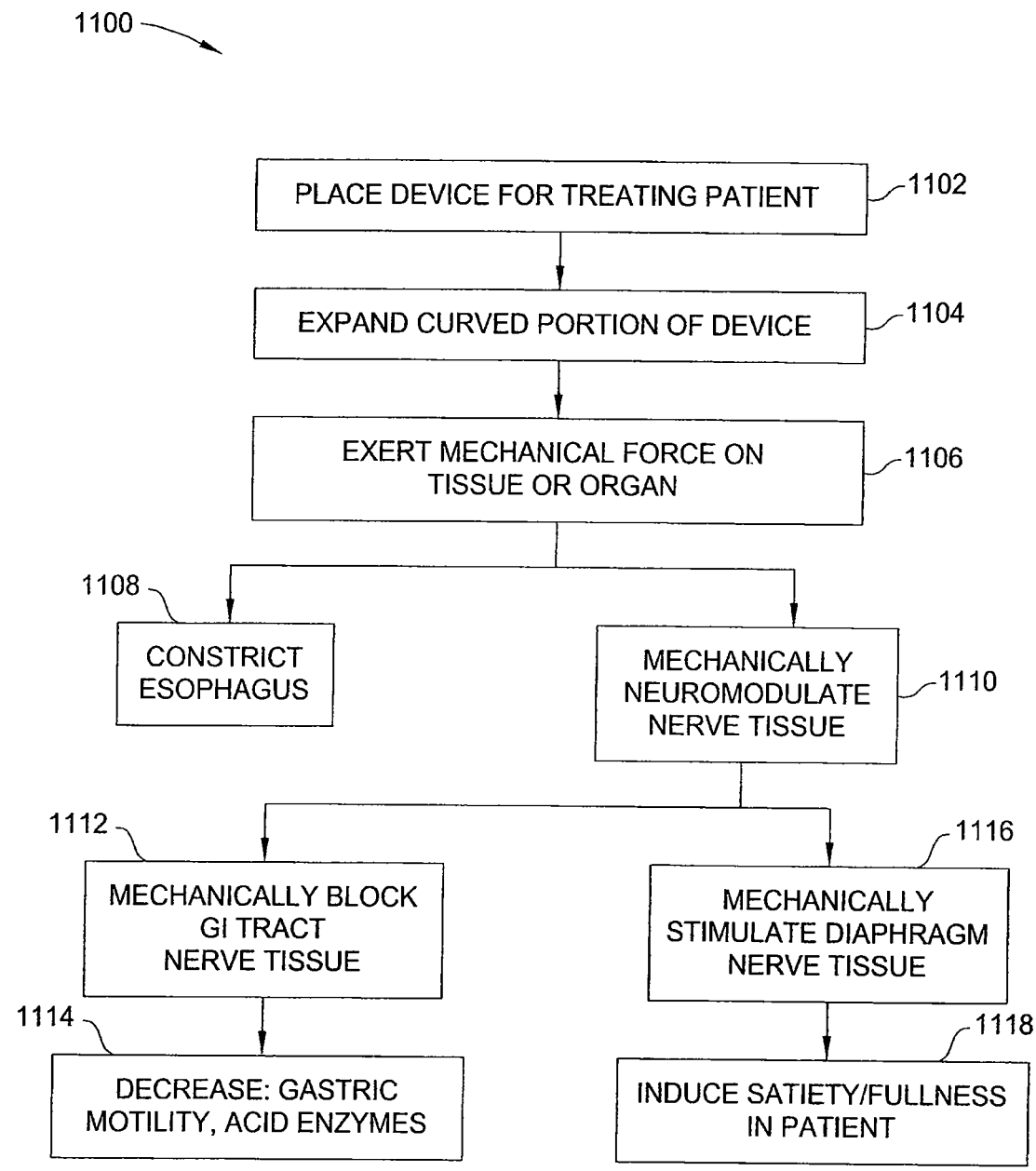
FIG. 45 is a flow diagram schematically representing a series of steps involved in a method for treating a patient, according to another embodiment of the invention.

FIG. 45 is a flow diagram schematically representing a series of steps involved in a method 1100 for treating a patient, according to another embodiment of the invention. Step 1102 involves placing a device with respect to the esophagus of the patient. The device may be disposed extraluminally in step 1102, for example, substantially as described for step 902 of method 900 (FIG. 43). The device may include a curved portion as well as various elements and features as disclosed for other embodiments of the invention, e.g., as described herein with respect to FIGS. 1-24. The curved portion may be expandable or adjustable in one or more dimensions, e.g., as described with reference to step 404 of method 400 (FIG. 37). Step 1104 involves expanding the curved portion in at least one dimension. Step 1106 involves exerting a mechanical force on at least one tissue or organ. The mechanical force may be exerted substantially as described for step 404 of method 400 (FIG. 37).

Step 1108 involves constricting the esophagus of the patient, wherein the esophagus may be constricted via the mechanical force exerted according to step 1106. The esophagus may be constricted sufficiently to inhibit passage of food through the esophagus such that intake of food into the stomach is restricted. In an embodiment, constriction of the lumen of the esophagus via exertion of the mechanical force may prevent or inhibit reflux from the stomach into the esophagus.

Step 1110 involves mechanically neuromodulating one or more tissues or organs. In an embodiment, the neuromodulation of step 1110 may result in mechanical blocking of nerve tissue that innervates the stomach or other portion(s) of the GI tract, according to step 1112, whereby acid and enzyme production by the stomach, as well as gastric motility, may be controlled. At least partial blocking of nerve tissue that innervates the stomach may decrease the gastric motility of the patient, decrease the production of gastric enzymes by the patient, or decrease the production of gastric acid by the patient, according to step 1114. Such decreased gastric activity may effectively decrease the rate of digestion of ingested food by the patient, leading to loss of excess weight by the patient. Such decreased gastric activity may alternatively, or additionally, effectively prevent or inhibit reflux of gastric contents into the esophagus of the patient, thereby treating or preventing GERD.

In an alternative embodiment of the method of FIG. 45, the neuromodulation of step 1110 may result in the nerve tissue being mechanically stimulated, according to step 1116, wherein the nerve tissue innervates the diaphragm of the patient. Stimulating nerve tissue that innervates the diaphragm may induce in the patient a sensation of satiety, or a feeling of having a full stomach. Such an induced sensation may effectively decrease the caloric intake of an obesity patient, leading to loss of excess weight by the patient.

Figure 46:
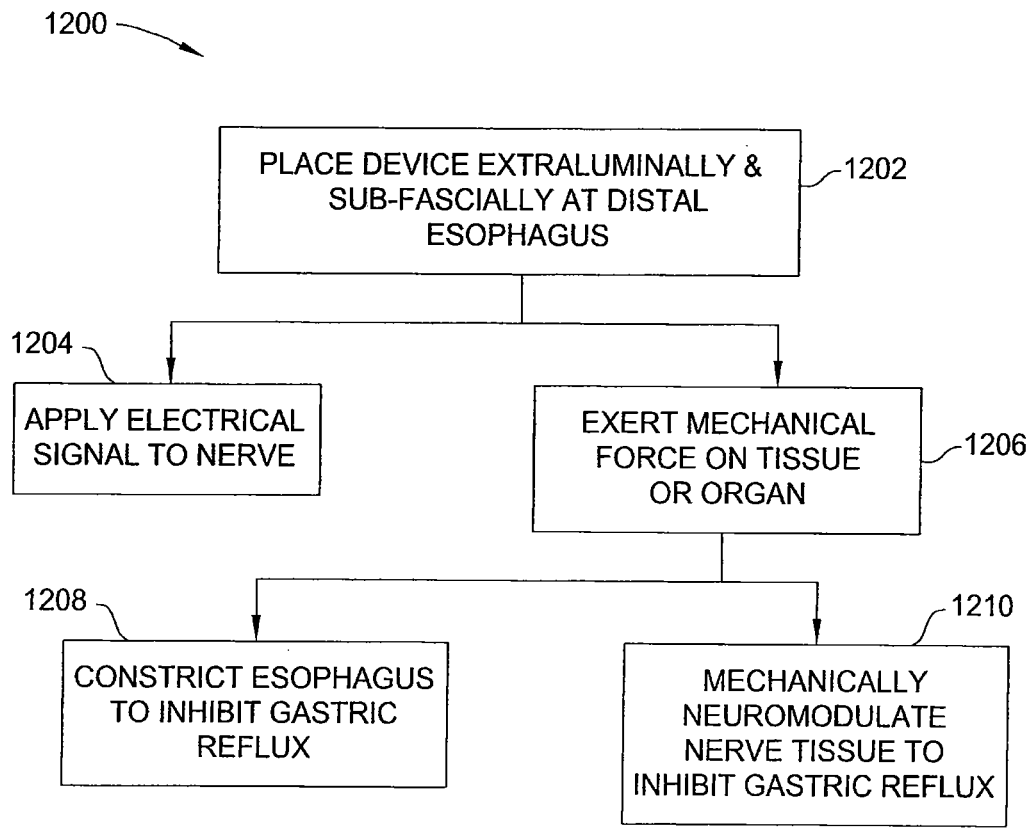
FIG. 46 is a flow diagram schematically representing a series of steps involved in a method for treating a patient, according to another embodiment of the invention.

FIG. 46 is a flow diagram schematically representing a series of steps involved in a method 1200 for treating a GERD patient, according to another embodiment of the invention. Step 1202 involves placing a device extraluminally and subfascially at the distal esophagus of the patient. In an embodiment which includes step 1204, the device may include a curved portion having at least one electrode disposed on an external surface of the curved portion. As an example, the electrode(s) may be disposed on at least one of a radially outer surface and a radially inner surface of the curved portion. The electrode(s) maybe adapted for electrical neuromodulation of a targeted nerve tissue. Step 1204 involves applying an electrical signal to the nerve tissue sufficient to treat the patient via electrical neuromodulation. The electrical neuromodulation and treatment of the patient in step 1204 may be accomplished, for example, substantially as described for the treatment of GERD with reference to method 1100 (FIG. 45). For example, electrical neuromodulation in step 1204 may inhibit gastric motility and decrease the volume of gastric enzymes and gastric acid produced by the stomach of the GERD patient.

With further reference to FIG. 46, in an embodiment which includes step 1206, the device may include a curved portion configured for controlled expansion thereof or adjustment of a diameter thereof. The controlled expansion, or adjustment of a diameter, of the curved portion is sufficient to exert a mechanical force on at least one tissue or organ targeted for treatment by the device. Step 1206 involves exerting a mechanical force on the at least one tissue or organ.

In an embodiment which includes step 1208, the device is disposed at the distal esophagus of the patient (according to step 1202) and the device may at least partially encircle the esophagus. In step 1208 the mechanical force may be exerted radially inward on the esophagus and may be sufficient to constrict the esophagus. Such constriction of the esophagus may be adjusted, e.g., by controlling the degree of radially inward expansion or by adjusting the internal diameter of the device, to inhibit gastric reflux in the GERD patient.

With still further reference to FIG. 46, in another embodiment which includes step 1210, the tissue targeted for treatment by the device may comprise nerve tissue. The mechanical force exerted as a result of the controlled expansion, or adjustment of a diameter, of the curved portion is sufficient to mechanically neuromodulate the nerve tissue targeted for treatment by the device. Step 1210 involves mechanically neuromodulating the nerve tissue. The nerve tissue may innervate the stomach. Mechanical neuromodulation in step 1210 may at least partially block the transmission of neural impulses to the stomach sufficient to inhibit gastric motility and decrease the volume of gastric enzymes and gastric acid produced by the stomach of the GERD patient, thereby effectively treating GERD in the patient.

Figure 47:
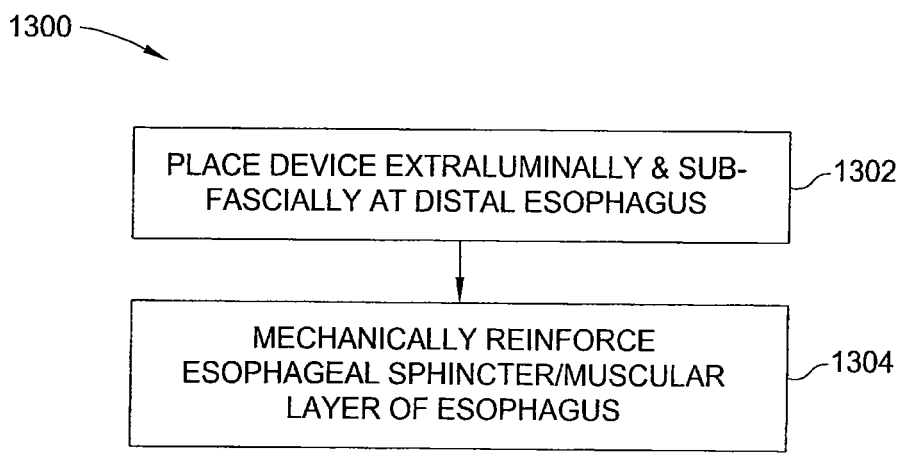
FIG. 47 is a flow diagram schematically representing a series of steps involved in a method for treating a patient, according to another embodiment of the invention.

FIG. 47 is a flow diagram schematically representing a series of steps involved in a method 1300 for treating a patient, according to another embodiment of the invention. Step 1302 involves placing a device extraluminally and subfascially at the distal esophagus. As an example, the device may be placed in step 1302 as described hereinabove with respect to other embodiments of the invention, e.g., with respect to method 300 (FIG. 37). In an embodiment, step 1302 may involve placing the device such that the device at least partially encircles the esophagus. Step 1302 may further involve placing the device in contact with at least one muscular layer of the esophagus. The device may include various elements and features as disclosed for other embodiments of the invention, e.g., as described herein with respect to FIGS. 1-46. Step 1304 may involve mechanically reinforcing the muscular layers of the esophagus, or mechanically reinforcing the lower esophageal sphincter of the patient, thereby tightening the lower esophageal sphincter. Such mechanical reinforcement at the distal esophagus and tightening of the lower esophageal sphincter decreases or prevents gastric reflux and effectively treats GERD.

Although the invention has been described predominantly with respect to the treatment of patients for obesity, and to a lesser extent GERD, various embodiments and aspects of the invention may also find applications for the treatment of other conditions as well as for the treatment of non-human animals.

In addition, it is to be understood that various elements, features, and characteristics of the different embodiments of the present invention may be combined in various combinations not inconsistent with the description hereinabove and the claims hereinbelow, and that such combinations are within the scope of the invention.

It is to be further understood that the foregoing relates to various exemplary embodiments of the invention, and that numerous modifications may be made thereto without departing from the spirit and scope of the invention as defined according to the following claims.

In one embodiment, a method for treating a patient includes a) placing a device extraluminally with respect to the esophagus such that said device at least partially encircles the esophagus of the patient, wherein said device includes a curved portion configured for radially outward expansion thereof and said radially outward expansion is independent of any radially inward expansion of said curved portion; and b) expanding said curved portion in at least one dimension, such that a surface of said curved portion exerts a mechanical force on at least one tissue or organ of the patient. In one or more of the embodiments disclosed herein, the method includes said placing step comprises advancing a linear conformation of said device sub-fascially around the esophagus and beneath the diaphragmatic fascia of the patient, whereby said linear conformation is transformed to an arcuate conformation. In one or more of the embodiments disclosed herein, the method includes said placing step comprises placing said device within esophageal tissue, whereby said device is retained in an arcuate conformation extraluminally around the esophagus at a location in at least close proximity to the gastro-esophageal junction. In one or more of the embodiments disclosed herein, the method includes said placing step comprises placing said device within esophageal tissue between an outer muscular layer of the esophagus and a fascial layer of the esophagus. In one or more of the embodiments disclosed herein, the method includes said placing step comprises placing said device at the gastro-esophageal junction, the esophageal-diaphragmatic junction, or the gastro-diaphragmatic junction of the patient. In one or more of the embodiments disclosed herein, wherein said expanding step comprises expanding said curved portion radially outward or radially inward, the tissue comprises nerve tissue, and said mechanical force comprises a first mechanical force sufficient to mechanically neuromodulate the nerve tissue. In one or more of the embodiments disclosed herein, the method further comprises c) via said first mechanical force, mechanically neuromodulating the nerve tissue, wherein said neuromodulating comprises at least partially blocking transmission of neural impulses in the nerve tissue, wherein the nerve tissue innervates the stomach or gastro-intestinal tract of the patient, and said neuromodulating inhibits at least one of i) gastric motility, ii) gastric acid production, and iii) gastric enzyme production in the patient. In one or more of the embodiments disclosed herein, said mechanically neuromodulating step comprises: via said first mechanical force, mechanically stimulating transmission of neural impulses in the nerve tissue, wherein the nerve tissue innervates the diaphragm of the patient, and said stimulating induces a feeling of fullness in the patient. In one or more of the embodiments disclosed herein, wherein said curved portion is configured for radially inward expansion thereof, and said radially inward expansion is independent of said radially outward expansion of said curved portion.

In another embodiment, a method for treating a patient includes a) advancing a linear conformation of a device sub-fascially around the esophagus of the patient, whereby said linear conformation is transformed to an arcuate conformation; and b) disposing said arcuate conformation beneath the diaphragmatic fascia at the distal esophagus. In one or more of the embodiments disclosed herein, said advancing step comprises advancing said device along a path of least resistance such that said arcuate conformation at least partially encircles the esophagus. In one or more of the embodiments disclosed herein, the method further comprises c) prior to step a), implanting said device beneath the diaphragmatic fascia of the patient, and wherein said advancing comprises pushing said linear conformation sub-fascially around the esophagus. In one or more of the embodiments disclosed herein, said advancing comprises pushing said linear conformation such that a distal end of said device follows a path of least resistance beneath the diaphragmatic fascia and around the esophagus, whereby said arcuate conformation at least partially encircles the esophagus. In one or more of the embodiments disclosed herein, said device is disposed within esophageal tissue such that said device is retained in contact with a muscular layer of the esophagus. In one or more of the embodiments disclosed herein, wherein said arcuate conformation forms a curved portion of said device, said curved portion is expandable in at least one dimension, and the method further comprises d) expanding said curved portion to an extent sufficient to exert a mechanical force on at least one tissue or organ of the patient. In one or more of the embodiments disclosed herein, wherein said tissue comprises nerve tissue, said mechanical force is sufficient to mechanically neuromodulate said nerve tissue, and said nerve tissue innervates the gastro-intestinal tract or the diaphragm. In one or more of the embodiments disclosed herein, wherein said organ comprises the esophagus, and said mechanical force is sufficient to constrict the lumen of the esophagus.

In another embodiment, a method for treating a patient includes a) placing a device around the esophagus such that said device at least partially encircles the esophagus of the patient, wherein said device includes a curved portion comprising a radially outer surface and a radially inner surface, said device is configured for radially outward expansion of said radially outer surface, said device is further configured for radially inward expansion of said radially inner surface, and said radially outward expansion is independent of said radially inward expansion; b) expanding said device by at least one of said radially outward expansion and said radially inward expansion sufficient to exert a mechanical force on at least one nerve tissue of the patient; and c) via said mechanical force, mechanically neuromodulating the nerve tissue. In one or more of the embodiments disclosed herein, said device is configured for said radially outward expansion concurrently with said radially inward expansion. In one or more of the embodiments disclosed herein, wherein said mechanically neuromodulating comprises at least partially blocking transmission of neural impulses in the nerve tissue, the nerve tissue innervates the stomach of the patient, and said mechanically neuromodulating controls at least one of i) gastric motility, ii) gastric acid production, and iii) gastric enzyme production in the patient. In one or more of the embodiments disclosed herein, wherein said mechanically neuromodulating comprises mechanically stimulating neural impulses in the nerve tissue, the nerve tissue comprises sensory nerve tissue, the nerve tissue innervates the diaphragm or the gastro-intestinal tract of the patient, and said mechanically stimulating induces a feeling of satiety in the patient.

In another embodiment, a method for treating a patient includes a) placing a device around the esophagus such that said device at least partially encircles the esophagus; and b) via said device, mechanically neuromodulating at least one nerve tissue of the patient. In one or more of the embodiments disclosed herein, step b) comprises c) via said device, exerting a mechanical force on the nerve tissue. In one or more of the embodiments disclosed herein, said device includes a radially outer surface defining an external diameter of said device and a radially inner surface defining an internal diameter of said device, and step c) comprises exerting said mechanical force via adjustment of at least one of said external diameter and said internal diameter. In one or more of the embodiments disclosed herein, the nerve tissue is disposed outside said external diameter of said device, and step c) comprises exerting said mechanical force via increasing said external diameter. In one or more of the embodiments disclosed herein, the nerve tissue is disposed within said internal diameter of said device, and step c) comprises exerting said mechanical force via decreasing said internal diameter. In one or more of the embodiments disclosed herein, said device includes a cannulated curved portion having a bore therethrough, a filament disposed within said bore, and a collar configured for slidably accommodating a first strand and a second strand of said filament, and said device is configured for adjusting said internal diameter and said external diameter by passage of at least one of said first strand and said second strand within said collar; and wherein step c) comprises passing at least one of said first strand and said second strand within said collar, whereby said internal diameter and said external diameter are adjusted. In one or more of the embodiments disclosed herein, step c) comprises d) via said mechanical force, at least partially blocking transmission of neural impulses in the nerve tissue. In one or more of the embodiments disclosed herein, the nerve tissue innervates the stomach, and step d) decreases at least one of: i) gastric motility, ii) gastric acid production, and iii) gastric enzyme production. In one or more of the embodiments disclosed herein, step c) comprises e) via said mechanical force, mechanically stimulating the nerve tissue. In one or more of the embodiments disclosed herein, step e) results in a sensation of satiety in the patient. In one or more of the embodiments disclosed herein, the method further comprises f) via said device, exerting a mechanical force radially inward on the esophagus, wherein said mechanical force is sufficient to constrict the esophagus and control the passage of food through the esophagus. In one or more of the embodiments disclosed herein, the method further comprises g) via said device, exerting a mechanical force radially inward on the esophagus, wherein said mechanical force is sufficient to constrict the esophagus and inhibit the reflux of acid from the stomach. In one or more of the embodiments disclosed herein, step a) comprises h) implanting said device beneath the diaphragmatic fascia of the patient. In one or more of the embodiments disclosed herein, step a) further comprises i) after step h), advancing said device beneath the diaphragmatic fascia to the esophagus, and embedding said device extraluminally beneath the parietal fascia and within esophageal tissue of the patient.

In another embodiment, a method for treating a patient includes a) placing a device at the distal esophagus of the patient; b) via said device, mechanically blocking a first nerve tissue, wherein the first nerve tissue is blocked via exertion of a mechanical force by said device on the first nerve tissue, wherein the first nerve tissue innervates the stomach, and said blocking decreases at least one of: i) gastric motility, ii) gastric acid production, and iii) gastric enzyme production; and c) via said device, mechanically stimulating a second nerve tissue, wherein said stimulating induces a sensation of satiety in the patient. In one or more of the embodiments disclosed herein, step a) comprises disposing said device such that said device at least partially encircles the esophagus, and the method further includes d) expanding said device radially inward such that said device constricts the lumen of the esophagus whereby passage of food into the stomach is controlled. In one or more of the embodiments disclosed herein, said device constricts the lumen of the esophagus at a location in at least close proximity to the diaphragm of the patient. In one or more of the embodiments disclosed herein, step a) comprises disposing said device beneath the diaphragmatic fascia of the patient such that said device is retained sub-fascially by the diaphragmatic fascia.

In another embodiment, a method for treating a patient includes a) advancing a first segment of a device from a first side of the patient's body towards a first side of the patient's esophagus; b) advancing a second segment of said device from a second side of the patient's body towards a second side of the patient's esophagus; c) at least partially encircling the esophagus with at least one of said first segment and said second segment; and d) coupling said first and second segments. In one or more of the embodiments disclosed herein, the method further includes e) prior to step d), implanting at least one of said first segment and said second segment beneath the diaphragmatic fascia of the patient. In one or more of the embodiments disclosed herein, step c) comprises implanting at least one of said first segment and said second segment at the diaphragm of the patient. In one or more of the embodiments disclosed herein, step c) comprises implanting at least one of said first segment and said second segment above or below the diaphragm of the patient. In one or more of the embodiments disclosed herein, said device is retained in position, sub-fascially around the esophagus, by the patient's diaphragmatic fascia. In one or more of the embodiments disclosed herein, at least one of said first and second segments is arcuate, U-shaped, C-shaped, or semi-circular. In one or more of the embodiments disclosed herein, said device includes an expandable curved portion, and the method further includes f) expanding said curved portion to an expanded configuration; g) via step f), exerting a mechanical force on at least one nerve tissue; and h) via said mechanical force, mechanically neuromodulating the nerve tissue. In one or more of the embodiments disclosed herein, said device includes an expandable curved portion, said curved portion includes a radially inner surface, and the method further includes i) expanding said curved portion to an expanded configuration such that said radially inner surface is urged radially inward; j) via step i), exerting a mechanical force radially inward on the esophagus; and k) via said mechanical force, constricting the lumen of the esophagus.

In another embodiment, a method for treating a patient includes a) placing a device around the esophagus of the patient such that said device at least partially encircles the esophagus, wherein said device includes: a curved portion configured for transformation between an expanded configuration and an unexpanded configuration, and at least one electrode disposed on said curved portion; and b) via said electrode, applying an electrical signal to at least one nerve tissue, wherein said electrical signal is sufficient to electrically neuromodulate the nerve tissue. In one or more of the embodiments disclosed herein, said electrode is disposed on an external surface of said curved portion, and the method further comprises c) prior to step b), transforming said curved portion from said unexpanded configuration to said expanded configuration, and d) via step c), forcing said electrode into electrical contact with the nerve tissue. In one or more of the embodiments disclosed herein, the nerve tissue innervates the stomach, and step b) comprises: via said electrical signal, at least partially blocking transmission of neural impulses in the nerve tissue. In one or more of the embodiments disclosed herein, said blocking the nerve tissue inhibits gastric motility. In one or more of the embodiments disclosed herein, said blocking the nerve tissue inhibits at least one of gastric acid secretion and gastric enzyme secretion. In one or more of the embodiments disclosed herein, the nerve tissue innervates the diaphragm, the nerve tissue comprises sensory nerve tissue, and step b) comprises: via said electrical signal, stimulating the nerve tissue. In one or more of the embodiments disclosed herein, said stimulating the nerve tissue induces a sensation of satiety in the patient.

In another embodiment, a method for treating obesity in a patient includes a) disposing a device beneath the diaphragmatic fascia of the patient; b) advancing said device sub-fascially towards the distal esophagus such that said device at least partially encircles the esophagus; and c) retaining said device in situ around the esophagus via a fascial layer of the patient. In one or more of the embodiments disclosed herein, the method includes d) via said device, mechanically blocking at least a first nerve tissue, wherein said blocking inhibits at least one of gastric motility and gastric secretion. In one or more of the embodiments disclosed herein, the method includes e) via said device, mechanically stimulating at least a second nerve tissue, wherein stimulating said second nerve tissue induces a sensation of satiety in the patient. In one or more of the embodiments disclosed herein, the method includes f) via said device, constricting the esophagus. In one or more of the embodiments disclosed herein, said device is embedded within esophageal tissue of the patient, whereby said device is retained extraluminally around the esophagus.

In another embodiment, a method for treating a patient includes a) introducing a device into the thorax or abdomen of the patient; b) implanting said device beneath the diaphragmatic fascia of the patient; and c) while said device is disposed beneath the diaphragmatic fascia, placing said device around the distal end of the esophagus. In one or more of the embodiments disclosed herein, step a) comprises introducing said device into the thorax, and step b) comprises implanting said device beneath the diaphragmatic fascia at a location in at least close proximity to the esophagus. In one or more of the embodiments disclosed herein, step c) comprises pushing said device sub-fascially along a path of least resistance such that said device at least partially encircles the esophagus.

In another embodiment, a method for treating gastro-esophageal reflux disease in a patient includes a) implanting a device beneath the diaphragmatic fascia of the patient; b) disposing said device sub-fascially at the distal end of the esophagus; and c) disposing said device extraluminally around the esophagus, wherein said device inhibits reflux from the stomach into the esophagus. In one or more of the embodiments disclosed herein, the method includes d) via said device, neuromodulating at least one nerve tissue, wherein the nerve tissue innervates the stomach. In one or more of the embodiments disclosed herein, said neuromodulating comprises at least partially blocking transmission of neural impulses by the nerve tissue. In one or more of the embodiments disclosed herein, the nerve tissue comprises a vagal trunk. In one or more of the embodiments disclosed herein, said device includes a substantially annular curved portion, and step d) comprises e) adjusting at least one of an internal diameter and an external diameter of said curved portion; f) via step e), exerting a mechanical force on the nerve tissue, and g) via step f), at least partially blocking transmission of neural impulses by the nerve tissue. In one or more of the embodiments disclosed herein, said device includes a curved portion and at least one electrode disposed on said curved portion, and step d) comprises h) adjusting at least one of an internal diameter and an external diameter of said curved portion; i) via said electrode, applying an electrical signal to the nerve tissue, and j) via said electrical signal, electrically neuromodulating the nerve tissue, wherein said electrically neuromodulating at least partially blocks transmission of neural impulses by the nerve tissue. In one or more of the embodiments disclosed herein, the nerve tissue comprises sympathetic nerve tissue or parasympathetic nerve tissue. In one or more of the embodiments disclosed herein, the method includes k) via said device, constricting the esophagus, wherein said constricting inhibits said reflux from the stomach. In one or more of the embodiments disclosed herein, the method includes l) via said device, mechanically reinforcing the lower gastro-esophageal sphincter of the patient whereby the lower gastro-esophageal sphincter is tightened, and wherein said reinforcing inhibits said reflux from the stomach. In one or more of the embodiments disclosed herein, the method includes m) via said device, mechanically reinforcing the muscular layer of the esophagus of the patient whereby said reinforcing inhibits said reflux from the stomach.

In another embodiment, a method for treating a patient includes a) placing a device extraluminally with respect to the esophagus such that said device at least partially encircles the esophagus of the patient, wherein said device includes a curved portion configured for exerting a mechanical force, on at least one tissue or organ, via adjustment of a diameter of said curved portion, said curved portion is cannulated to allow passage of a filament therethrough, said device further includes a collar configured for slidably accommodating a first strand and a second strand of said filament, and said device is configured for adjusting said diameter of said curved portion by passage of at least one of said first strand and said second strand of said filament within said collar; and b) via said passage of said filament, adjusting said diameter of said curved portion. In one or more of the embodiments disclosed herein, step a) comprises embedding said device within esophageal tissue at the distal esophagus. In one or more of the embodiments disclosed herein, step a) comprises disposing said device sub-fascially. In one or more of the embodiments disclosed herein, the method includes c) after step b), locking said collar with respect to movement of said filament relative to said collar. In one or more of the embodiments disclosed herein, said curved portion includes a radially outer surface, step b) comprises increasing an external diameter of said curved portion, said mechanical force is exerted via said radially outer surface, and said mechanical force is sufficient to mechanically neuromodulate at least one nerve tissue. In one or more of the embodiments disclosed herein, said nerve tissue innervates the gastro-intestinal tract of the patient, and said mechanical force is sufficient to at least partially block transmission of neural impulses in the nerve tissue, wherein gastric motility or gastric secretion is controlled. In one or more of the embodiments disclosed herein, the nerve tissue innervates the diaphragm of the patient, and said mechanical force is sufficient to stimulate transmission of neural impulses in the nerve tissue, wherein a sensation of fullness in induced in the patient. In one or more of the embodiments disclosed herein, said curved portion includes a radially inner surface, step b) comprises decreasing an internal diameter of said curved portion, said mechanical force is exerted via said radially inner surface, and said mechanical force is sufficient to mechanically neuromodulate at least one nerve tissue. In one or more of the embodiments disclosed herein, the nerve tissue innervates the gastro-intestinal tract of the patient, and said mechanical force is sufficient to at least partially block transmission of neural impulses in the nerve tissue, wherein gastric motility or gastric secretion is decreased. In one or more of the embodiments disclosed herein, said curved portion includes a radially inner surface, step b) comprises decreasing an internal diameter of said curved portion, said mechanical force is exerted via said radially inner surface, and said mechanical force is sufficient to mechanically constrict the lumen of the esophagus and to control the passage of food through the lumen of the esophagus.

In another embodiment, a method for treating a patient includes a) passing an intraluminal guide intraluminally within the esophagus to the distal esophagus of the patient, wherein said intraluminal guide includes an expandable distal end portion having a waist portion; b) introducing an extraluminal constriction device into the thorax or abdomen and to a location in at least close proximity to the gastro-esophageal junction; c) at least partially expanding said distal end portion intraluminally within the esophagus; and d) advancing said device extraluminally with respect to the esophagus and around said waist portion such that said device at least partially encircles the distal esophagus. In one or more of the embodiments disclosed herein, said intraluminal guide has an unexpanded configuration, and wherein step a) comprises passing said unexpanded configuration of said intraluminal guide intraluminally to the distal esophagus. In one or more of the embodiments disclosed herein, said intraluminal guide includes a distal expansion chamber and a proximal expansion chamber, and wherein said waist portion is disposed between said distal expansion chamber and said proximal expansion chamber, and step c) comprises expanding at least one of said distal expansion chamber and said proximal expansion chamber. In one or more of the embodiments disclosed herein, step a) comprises disposing said waist portion in at least close proximity to the gastro-esophageal junction of the patient. In one or more of the embodiments disclosed herein, step d) comprises advancing said device along a substantially annular path located radially outward from said waist portion. In one or more of the embodiments disclosed herein, the method includes e) before step d), disposing said device beneath the diaphragmatic fascia of the patient. In one or more of the embodiments disclosed herein, said device is placed around the distal end of the esophagus of the patient while said device is disposed beneath the diaphragmatic fascia. In one or more of the embodiments disclosed herein, step d) comprises pushing said device sub-fascially along a path of least resistance such that said device at least partially encircles the lumen of the esophagus. In one or more of the embodiments disclosed herein, step d) comprises embedding said device sub-fascially and extraluminally within esophageal tissue such that said constriction device at least partially encircles the lumen of the esophagus. In one or more of the embodiments disclosed herein, said intraluminal guide further includes a light source, and the method further comprises, prior to or during step d): f) via said light source, illuminating at least a portion of said distal end portion of said intraluminal guide.

In another embodiment, a device includes at least one curved portion, wherein said device is configured for radially outward expansion of said curved portion independently of radially inward expansion of said curved portion, and said curved portion is configured for at least partially encircling the esophagus of a patient. In one or more of the embodiments disclosed herein, said device is configured for transformation from a linear conformation to an arcuate conformation, and said arcuate conformation forms said curved portion. In one or more of the embodiments disclosed herein, said device is configured for transformation from said linear conformation to said arcuate conformation via sub-fascial passage around the esophagus. In one or more of the embodiments disclosed herein, said curved portion is at least substantially annular. In one or more of the embodiments disclosed herein, said curved portion is at least substantially C-shaped, O-shaped, or U-shaped. In one or more of the embodiments disclosed herein, said curved portion comprises a plurality of interconnectable segments. In one or more of the embodiments disclosed herein, further comprising at least one electrode disposed on said curved portion. In one or more of the embodiments disclosed herein, said curved portion comprises a radially outer surface, said radially outward expansion urges said radially outer surface radially outward, and said radially outward expansion is sufficient to exert a first mechanical force, via said radially outer surface, on at least one tissue or organ of the patient's body. In one or more of the embodiments disclosed herein, said radially outward expansion is adjustable for adjusting said first mechanical force. In one or more of the embodiments disclosed herein, the tissue comprises at least one nerve tissue, and said first mechanical force is sufficient to mechanically neuromodulate the nerve tissue. In one or more of the embodiments disclosed herein, said first mechanical force is sufficient to mechanically block transmission of neural impulses in the nerve tissue. In one or more of the embodiments disclosed herein, the nerve tissue innervates the stomach or gastro-intestinal tract, and the nerve tissue is involved in at least one of: i) gastric motility, ii) gastric secretion of acid, and iii) gastric secretion of enzymes. In one or more of the embodiments disclosed herein, the nerve tissue comprises at least one sensory nerve or sensory nerve fiber, the nerve tissue innervates the diaphragm of the patient, and said first mechanical force is sufficient to mechanically stimulate transmission of neural impulses in the nerve tissue and to induce a feeling of satiety in the patient. In one or more of the embodiments disclosed herein, said first mechanical force is sufficient to mimic fullness in the patient. In one or more of the embodiments disclosed herein, the nerve tissue comprises parasympathetic nerve tissue or sympathetic nerve tissue. In one or more of the embodiments disclosed herein, said curved portion comprises a radially inner surface, said device is configured for said radially inward expansion of said radially inner surface, said radially inward expansion urges said radially inner surface radially inward, and said radially inward expansion is sufficient to exert a second mechanical force, via said radially inner surface, on at least one tissue or organ of the patient's body. In one or more of the embodiments disclosed herein, said radially inward expansion is adjustable for adjusting said second mechanical force. In one or more of the embodiments disclosed herein, the tissue comprises nerve tissue, and said second mechanical force is sufficient to mechanically neuromodulate the nerve tissue. In one or more of the embodiments disclosed herein, said second mechanical force is sufficient to mechanically block transmission of neural impulses in the nerve tissue. In one or more of the embodiments disclosed herein, the nerve tissue innervates the stomach, and the nerve tissue is involved in at least one of: i) gastric motility, ii) gastric secretion of acid, and iii) gastric secretion of enzymes. In one or more of the embodiments disclosed herein, the nerve tissue comprises a vagal trunk. In one or more of the embodiments disclosed herein, the nerve tissue comprises parasympathetic nerve tissue or sympathetic nerve tissue. In one or more of the embodiments disclosed herein, said at least one tissue or organ comprises the esophagus, and said second mechanical force is sufficient to constrict the esophagus and to control food intake into the stomach of the patient.

In another embodiment, a device for implantation within a patient via an introducer element, said device having a substantially linear conformation, said device configured for adopting said linear conformation when said device is disposed within a shaft of said introducer element, said device further configured for adopting a substantially arcuate conformation when said device is implanted in the patient, said device including an expandable curved portion formed from said arcuate conformation, said curved portion configured for encircling the esophagus of the patient, said curved portion having an internal diameter and an external diameter, said curved portion configured for adjusting said external diameter independently of adjustment of said internal diameter, said curved portion includes first and second independently expandable elements, said first expandable element configured for adjusting said internal diameter independently of said external diameter, and said second expandable element configured for adjusting said external diameter independently of said internal diameter. In one or more of the embodiments disclosed herein, said curved portion includes an extensible radially inner surface defining said internal diameter, and an extensible radially outer surface defining said external diameter, and wherein said radially inner surface is extended radially inward when said first expandable element is expanded, and said radially outer surface is extended radially outward when said second expandable element is expanded. In one or more of the embodiments disclosed herein, the device includes a barrier disposed between said first and second expandable elements, wherein said barrier is at least substantially non-extensible when at least one of said first and second expandable elements are expanded.

In another embodiment, an apparatus includes a device including at least one curved portion, said curved portion including a radially outer surface, and a radially inner surface, wherein said curved portion is configured for at least partially encircling the esophagus of a patient, said device is configured for radially outward expansion of said radially outer surface, said device is further configured for radially inward expansion of said radially inner surface, and said radially outward expansion is independent of said radially inward expansion. In one or more of the embodiments disclosed herein, said radially outer surface defines an external diameter of said curved portion, said radially inner surface defines an internal diameter of said curved portion, said radially outward expansion increases said external diameter, and said radially outward expansion does not substantially increase or decrease said internal diameter. In one or more of the embodiments disclosed herein, said radially outer surface defines an external diameter of said curved portion, said radially inner surface defines an internal diameter of said curved portion, and said radially inward expansion decreases said internal diameter, and said radially inward expansion does not substantially increase or decrease said external diameter. In one or more of the embodiments disclosed herein, said device comprises a first expandable element; and a second expandable element, wherein said device is configured for expansion or contraction of said second expandable element independently of expansion or contraction of said first expandable element, and said device is further configured for expansion or contraction of said first expandable element independently of expansion or contraction of said second expandable element. In one or more of the embodiments disclosed herein, the apparatus includes a barrier disposed between said first and second expandable elements, wherein said barrier is at least substantially non-extensible when said first and second expandable elements are expanded. In one or more of the embodiments disclosed herein, said first expandable element and said second expandable element are at least substantially concentric. In one or more of the embodiments disclosed herein, the apparatus includes a first conduit in fluid communication with said first expandable element; and a second conduit in fluid communication with said second expandable element. In one or more of the embodiments disclosed herein, said first expandable element comprises a first inflatable member, said second expandable element comprises a second inflatable member, said first inflatable member is inflatable via passage of an inflation medium through said first conduit, and said second inflatable member is inflatable via passage of said inflation medium through said second conduit. In one or more of the embodiments disclosed herein, said inflation medium comprises a fluid, a gel, a gas, or a liquid. In one or more of the embodiments disclosed herein, the apparatus includes a reservoir in separate fluid communication with said first expandable element and with said second expandable element, said reservoir storing a quantity of said inflation medium. In one or more of the embodiments disclosed herein, the apparatus includes a first injection port in fluid communication with said first inflatable member; and a second injection port in fluid communication with said second inflatable member. In one or more of the embodiments disclosed herein, expansion of said second expandable element effects said radially outward expansion of said curved portion, said radially outward expansion urges said radially outer surface radially outward, expansion of said first expandable element effects said radially inward expansion of said curved portion, and said radially inward expansion urges said radially inner surface radially inward. In one or more of the embodiments disclosed herein, said device is configured for independent expansion or contraction of said first expandable element and said second expandable element. In one or more of the embodiments disclosed herein, said device is configured for concurrent expansion or contraction of said first expandable element and said second expandable element. In one or more of the embodiments disclosed herein, said device is transformable from a linear conformation to an arcuate conformation via sub-fascial advancement of said device around the esophagus.

In another embodiment, a device for treating a patient includes at least one curved portion, wherein said curved portion comprises a plurality of inter-connectable segments, said curved portion is at least substantially C-shaped, O-shaped, or U-shaped, and said curved portion is configured for at least partially encircling the esophagus of the patient. In one or more of the embodiments disclosed herein, each of said inter-connectable segments comprises an arcuate segment, and said curved portion comprise two of said arcuate segments. In one or more of the embodiments disclosed herein, said curved portion comprises an annulus formed by interconnection of said arcuate segments. In one or more of the embodiments disclosed herein, the device includes at least one electrode disposed on said curved portion. In one or more of the embodiments disclosed herein, said curved portion includes a radially outer surface, said curved portion is configured for radially outward expansion of said radially outer surface, said radially outer surface defines an external diameter of said curved portion, said radially outward expansion increases said external diameter, and said radially outward expansion is sufficient to exert a first mechanical force against at least one tissue or organ of the patient. In one or more of the embodiments disclosed herein, the tissue comprises at least one nerve tissue, and said first mechanical force is sufficient to mechanically stimulate or mechanically block said nerve tissue. In one or more of the embodiments disclosed herein, said device is configured for said radially outward expansion independently of radially inward expansion of said curved portion. In one or more of the embodiments disclosed herein, said device is configured for said radially outward expansion in the absence of said radially inward expansion of said curved portion. In one or more of the embodiments disclosed herein, said curved portion includes a radially inner surface, said curved portion is configured for radially inward expansion of said radially inner surface, said radially inner surface defines an internal diameter of said curved portion, said radially inward expansion decreases said internal diameter, and said radially inward expansion is sufficient to exert a second mechanical force against at least at least one tissue or organ of the patient. In one or more of the embodiments disclosed herein, the tissue comprises at least one nerve tissue, and said second mechanical force is sufficient to mechanically block said nerve tissue. In one or more of the embodiments disclosed herein, said radially inner surface is configured for constricting the esophagus, and said second mechanical force is sufficient to constrict the esophagus such that passage of food through the esophagus is controlled via said radially inward expansion. In one or more of the embodiments disclosed herein, said device is configured for said radially inward expansion independently of radially outward expansion of said curved portion. In one or more of the embodiments disclosed herein, said device is configured for said radially inward expansion in the absence of said radially outward expansion of said curved portion.

In another embodiment, an apparatus for treating a patient, said apparatus includes a device including at least one curved portion, wherein said curved portion includes at least one expandable element for expanding said curved portion in at least one dimension; and at least one electrode disposed on said curved portion, wherein said device is configured for making electrical contact with a targeted nerve tissue of the patient. In one or more of the embodiments disclosed herein, expansion of said curved portion urges said electrode into said electrical contact with the nerve tissue. In one or more of the embodiments disclosed herein, said device is configured for at least partially encircling the esophagus of the patient. In one or more of the embodiments disclosed herein, said electrode is configured for applying an electrical signal to the nerve tissue, and said electrical signal is sufficient to electrically neuromodulate the nerve tissue. In one or more of the embodiments disclosed herein, said device is configured for applying an electrical signal to the nerve tissue via said electrode, and said electrode is configured for electrically stimulating or electrically blocking the nerve tissue. In one or more of the embodiments disclosed herein, said expansion of said curved portion comprises radially outward expansion of a radially outer surface of said curved portion. In one or more of the embodiments disclosed herein, said expansion of said curved portion comprises radially inward expansion of a radially inner surface of said curved portion. In one or more of the embodiments disclosed herein, said radially outward expansion is independent of radially inward expansion of said curved portion. In one or more of the embodiments disclosed herein, said curved portion includes an external surface, and said electrode is disposed on said external surface. In one or more of the embodiments disclosed herein, said device is configured for transformation from a linear conformation to an arcuate conformation, said arcuate conformation forms said curved portion, and said device is configured for transforming said linear conformation to said arcuate conformation via sub-fascial passage around the esophagus of the patient. In one or more of the embodiments disclosed herein, said curved portion comprises a plurality of inter-connectable arcuate segments.

In another embodiment, a device includes at least one curved portion, wherein said device is transformable from a linear conformation to an arcuate conformation, said device is configured for at least partially encircling the esophagus of a patient, said device is configured for transforming said linear conformation to said arcuate conformation by pushing said device sub-fascially around the esophagus, and said arcuate conformation forms said curved portion. In one or more of the embodiments disclosed herein, said linear conformation comprises a distal end and a proximal end, said device is configured for coupling said distal end to said proximal end to form said curved portion, and said device is further configured for radially outward expansion of said curved portion. In one or more of the embodiments disclosed herein, said device is further configured for radially inward expansion of said curved portion, and said radially outward expansion is independent of said radially inward expansion. In one or more of the embodiments disclosed herein, said curved portion includes a first expandable element; and a second expandable element, wherein said device is configured for expansion or contraction of said second expandable element independently of expansion or contraction of said first expandable element. In one or more of the embodiments disclosed herein, said curved portion is at least substantially C-shaped, U-shaped, or O-shaped.

In another embodiment, an apparatus for treating an obesity patient, includes a surgically implantable device including a curved portion, said curved portion including a first end and a second end, a radially outer surface defining an external diameter, and a radially inner surface defining an internal diameter, wherein said curved portion is cannulated to provide a bore therethrough; a filament disposed within said bore; and a collar configured for slidably accommodating a first strand and a second strand of said filament, wherein said device is configured for adjusting said internal diameter and said external diameter of said curved portion by passage of at least one of said first strand and said second strand within said collar, and wherein said curved portion configured for placement around the esophagus of the patient. In one or more of the embodiments disclosed herein, said curved portion is configured for sub-fascial and extraluminal placement around the distal esophagus of the patient, and said internal diameter is adjustable such that said radially inner surface constricts the distal esophagus. In one or more of the embodiments disclosed herein, said filament extends distally from said collar to said second end of said curved portion, said filament further extending through said bore from said second end of said curved portion to said first end of said curved portion, and said filament still further extending proximally from said first end of said curved portion to said collar. In one or more of the embodiments disclosed herein, said filament still further extends from said first end of said curved portion proximally through said collar and proximally beyond said collar. In one or more of the embodiments disclosed herein, axial movement of said filament with respect to said collar controls said external diameter and said internal diameter of said curved portion. In one or more of the embodiments disclosed herein, axial movement of said collar with respect to said filament controls said external diameter and said internal diameter of said curved portion. In one or more of the embodiments disclosed herein, said collar is adapted for locking said filament with respect to said collar such that axial movement of said filament with respect to said collar is prevented when said collar is in a locked configuration. In one or more of the embodiments disclosed herein, said collar is adapted for reversibly locking and unlocking said filament. In one or more of the embodiments disclosed herein, said filament comprises a guide wire. In one or more of the embodiments disclosed herein, said filament includes at least one marker configured for visualization, during a surgical procedure, of a relative location of said filament with respect to at least one of said curved portion and said collar. In one or more of the embodiments disclosed herein, said marker comprises at least one gradation or at least one alphanumeric character. In one or more of the embodiments disclosed herein, said filament is marked with at least one color.

In another embodiment, an intraluminal guide for treating a patient, said intraluminal guide having a distal end portion including a distal expansion chamber, a proximal expansion chamber, and a waist portion, said waist portion disposed between said distal expansion chamber and said proximal expansion chamber; and a channel, in fluid communication with said distal end portion, for expanding said distal expansion chamber and said proximal expansion chamber, wherein said channel extends proximally from said proximal expansion chamber, wherein an unexpanded configuration of said distal end portion is configured for intraluminal passage within the esophagus of the patient, and said distal expansion chamber and said proximal expansion chamber are configured for intraluminal expansion within the esophagus. In one or more of the embodiments disclosed herein, said distal expansion chamber is in fluid communication with said proximal expansion chamber via said waist portion. In one or more of the embodiments disclosed herein, at least one of said distal expansion chamber and said proximal expansion chamber is substantially globular. In one or more of the embodiments disclosed herein, at least one of said distal expansion chamber and said proximal expansion chamber is substantially discoid. In one or more of the embodiments disclosed herein, said intraluminal guide is configured for guiding placement of an extraluminal device around the esophagus of a patient. In one or more of the embodiments disclosed herein, said waist portion is adapted for guiding placement of an extraluminal device around the distal esophagus of the patient, and said waist portion is configured for locating said device extraluminally between said distal expansion chamber and said proximal expansion chamber. In one or more of the embodiments disclosed herein, the guide includes a light source for illuminating at least one of said distal expansion chamber, said waist portion, and said proximal expansion chamber. In one or more of the embodiments disclosed herein, said light source is disposed within an internal surface of said intraluminal guide. In one or more of the embodiments disclosed herein, said light source is further configured for extraluminal illumination of at least one tissue or organ. In one or more of the embodiments disclosed herein, said distal end portion is configured for guiding a linear configuration of said extraluminal device around said waist portion and between said distal expansion chamber and said proximal expansion chamber, and said linear configuration is transformed to an arcuate configuration of said extraluminal device by advancement of said extraluminal device around said waist portion.

In another embodiment, a system for treating a patient including an introducer element including a shaft, said shaft having a proximal end and a distal end, wherein said introducer element is adapted for insertion of said distal end into the thorax or abdomen of the patient; and a device for implantation within the patient, said device adapted for passage within said shaft, said device configured for adopting a substantially linear conformation when said device is disposed within said shaft, and said device further configured for adopting a substantially arcuate conformation when said device is implanted in the patient, said device including an expandable curved portion formed from said arcuate conformation, said curved portion is configured for at least partially encircling the esophagus of the patient, said curved portion having an internal diameter and an external diameter, and said device is configured for adjusting said external diameter independently of adjustment of said internal diameter. In one or more of the embodiments disclosed herein, further comprising an intraluminal guide configured for guiding placement of said device with respect to the esophagus of the patient. In one or more of the embodiments disclosed herein, said intraluminal guide comprises a distal end portion including a distal expansion chamber, a proximal expansion chamber, and a waist portion disposed between said distal expansion chamber and said proximal expansion chamber; and a channel in fluid communication with said distal end portion for expanding said distal expansion chamber and said proximal expansion chamber, said channel extending proximally from said proximal expansion chamber, wherein an unexpanded configuration of said distal end portion is configured for intraluminal passage within the esophagus, and said distal expansion chamber and said proximal expansion chamber are configured for intraluminal expansion within the esophagus. In one or more of the embodiments disclosed herein, said curved portion includes two independently expandable elements configured for independent adjustment of said external diameter and said internal diameter. In one or more of the embodiments disclosed herein, said shaft is sized for insertion through an incision in the patient of 12 mm or less.

In another embodiment, a system for treating a patient includes an introducer element including a shaft, said shaft having a proximal end and a distal end, wherein said introducer element is adapted for insertion of said distal end into the thorax or abdomen of the patient; an implantable device for implantation within the patient, said device adapted for passage within said shaft, said device configured for adopting a substantially linear conformation when said device is disposed within said shaft, and said device further configured for adopting a substantially arcuate conformation when said device is implanted in the patient, said device including an expandable curved portion formed from said arcuate conformation, and said curved portion is configured for at least partially encircling the esophagus of the patient; and an intraluminal guide including an expandable distal end portion wherein an unexpanded configuration of said distal end portion is configured for intraluminal passage to the distal esophagus of the patient, and said distal end portion is configured for intraluminal expansion within the esophagus and for guiding placement of said device around the esophagus of the patient. In one or more of the embodiments disclosed herein, said distal end portion includes a distal expansion chamber, a proximal expansion chamber, and a waist portion disposed between said distal expansion chamber and said proximal expansion chamber, and said intraluminal guide is configured for guiding advancement of said device around said waist portion such that said curved portion at least partially encircles the distal esophagus of the patient.

What is claimed is:

1. A method for treating a patient, comprising:
    a) placing a device extraluminally with respect to the esophagus such that said device at least partially encircles the esophagus of the patient by advancing a linear conformation of said device sub-fascially around the esophagus and beneath the diaphragmatic fascia of the patient, whereby said linear conformation is transformed to an arcuate conformation, wherein:
        said device includes a curved portion having an outer inflatable element having a first conduit for inflation and configured for radially outward expansion relative to the esophagus, an inner inflatable element having a second conduit for inflation and configured for radially inward expansion relative to the esophagus, and
        said radially outward expansion is independent of any radially inward expansion of said curved portion;
    b) securing the device around the esophagus with the first and second conduit; and
    c) expanding said curved portion in at least one dimension, such that a surface of said curved portion exerts a mechanical force on at least one tissue or organ of the patient.

2. The method of claim 1, wherein said placing step comprises placing said device within esophageal tissue, whereby said device is retained in an arcuate conformation extraluminally around the esophagus at a location in at least close proximity to the gastro-esophageal junction.

3. The method of claim 1, wherein said placing step comprises placing said device within esophageal tissue between an outer muscular layer of the esophagus and a fascial layer of the esophagus.

4. The method of claim 1, wherein said placing step comprises placing said device at the gastro-esophageal junction, the esophageal-diaphragmatic junction, or the gastro-diaphragmatic junction of the patient.

5. The method of claim 1, wherein:
said expanding step comprises expanding said curved portion radially outward or radially inward,
the tissue comprises nerve tissue, and
said mechanical force comprises a first mechanical force sufficient to mechanically neuromodulate the nerve tissue.

6. The method of claim 5, further comprising:
c) via said first mechanical force, mechanically neuromodulating the nerve tissue, wherein said neuromodulating comprises at least partially blocking transmission of neural impulses in the nerve tissue, wherein:
the nerve tissue innervates the stomach or gastro-intestinal tract of the patient, and
said neuromodulating inhibits at least one of i) gastric motility, ii) gastric acid production, and iii) gastric enzyme production in the patient.

7. The method of claim 6, wherein said mechanically neuromodulating step comprises: via said first mechanical force, mechanically stimulating transmission of neural impulses in the nerve tissue, wherein:
the nerve tissue innervates the diaphragm of the patient, and
said stimulating induces a feeling of fullness in the patient.

8. The method of claim 1, wherein a barrier is disposed between the inner and outer inflatable elements, and said barrier is substantially non-extensible when at least one of the inflatable elements is expanded.

9. A method for treating a patient, comprising:
a) placing a device extraluminally with respect to the esophagus such that the device at least partially encircles the esophagus of the patient by advancing a linear conformation of the device sub-fascially around the esophagus and beneath the diaphragmatic fascia of the patient, whereby the linear conformation is transformed to an arcuate conformation, wherein the device includes:
a curved portion having an outer inflatable element having a first conduit for inflation and configured for radially outward expansion relative to the esophagus and an inner inflatable element having a second conduit for inflation and configured for radially inward expansion relative to the esophagus, and
a barrier disposed between the inner and outer inflatable elements, and the barrier is substantially non-extensible when at least one of the inflatable elements is expanded;
b) securing the device around the esophagus with the first and second conduit; and
c) expanding the curved portion in at least one dimension, such that a surface of the curved portion exerts a mechanical force on at least one tissue or organ of the patient.

10. The method of claim 9, wherein expansion of the outer inflatable element is independent of the inner inflatable element.

11. The method of claim 10, wherein:
the expanding step comprises expanding the curved portion radially outward or radially inward,
the tissue comprises nerve tissue, and
the mechanical force comprises a first mechanical force sufficient to mechanically neuromodulate the nerve tissue.

12. The method of claim 11, further comprising:
c) via the first mechanical force, mechanically neuromodulating the nerve tissue to at least partially block transmission of neural impulses in the nerve tissue,
wherein the nerve tissue innervates the stomach or gastro-intestinal tract of the patient, and
the neuromodulating inhibits at least one of i) gastric motility, ii) gastric acid production, and iii) gastric enzyme production in the patient.

13. The method of claim 12, wherein the mechanically neuromodulating step comprises: via the first mechanical force, mechanically stimulating transmission of neural impulses in the nerve tissue, wherein:
the nerve tissue innervates the diaphragm of the patient, and
the stimulating induces a feeling of fullness in the patient.

* * * * *